(12) United States Patent
Lim et al.

(10) Patent No.: US 10,224,491 B2
(45) Date of Patent: Mar. 5, 2019

(54) AMINE-BASED COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Jino Lim, Yongin (KR); Youngkook Kim, Yongin (KR); Jongwoo Kim, Yongin (KR); Hyungseok Jang, Yongin (KR); Seokhwan Hwang, Yongin (KR)

(73) Assignee: SAMSUNG DISPLAY CO., LTD., Yongin, Gyeonggi-do (KR)

( * ) Notice: Subject to any disclaimer, the term of this patent is extended or adjusted under 35 U.S.C. 154(b) by 282 days.

(21) Appl. No.: 14/727,266

(22) Filed: Jun. 1, 2015

(65) Prior Publication Data

US 2016/0190464 A1 Jun. 30, 2016

(30) Foreign Application Priority Data

Dec. 24, 2014 (KR) ........................ 10-2014-0188647

(51) Int. Cl.
*H01L 51/00* (2006.01)
*C07D 307/91* (2006.01)
(Continued)

(52) U.S. Cl.
CPC ........ *H01L 51/0073* (2013.01); *C07D 307/91* (2013.01); *C07D 401/14* (2013.01);
(Continued)

(58) Field of Classification Search
CPC ............. H01L 51/0073; H01L 51/0074; H01L 51/0071; H01L 51/0059; H01L 51/006;
(Continued)

(56) References Cited

U.S. PATENT DOCUMENTS 6,465,115 B2 10/2002 Shi et al.
6,596,415 B2 7/2003 Shi et al.
(Continued)

FOREIGN PATENT DOCUMENTS

KR 10-2011-0011647 A 2/2011
KR 10-2012-0066076 A 6/2012
(Continued)

*Primary Examiner* — Ruiyun Zhang
(74) *Attorney, Agent, or Firm* — Lee & Morse, P.C.

(57) ABSTRACT

An amine-based compound and an organic light-emitting device, the amine-based compound being represented by the following Formula 1:

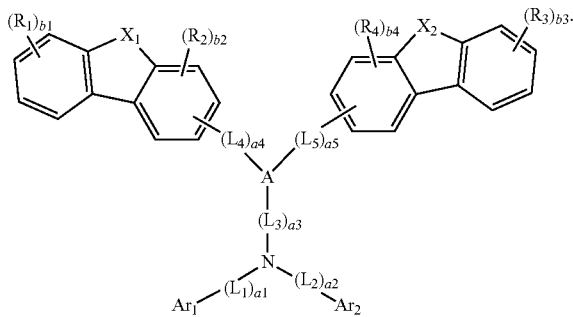

14 Claims, 1 Drawing Sheet

(51) Int. Cl.
*C07D 401/14* (2006.01)
*H01L 51/50* (2006.01)

(52) U.S. Cl.
CPC ........ H01L 51/006 (2013.01); H01L 51/0059 (2013.01); *H01L 51/0081* (2013.01); *H01L 51/5056* (2013.01)

(58) Field of Classification Search
CPC ............ H01L 51/5056; H01L 51/5012; C07D 307/91; C07D 401/14; C07D 333/76; Y10S 428/917; C09B 57/008; C09K 11/06; C09K 2211/1088; C09K 2211/1011
USPC .......... 428/690, 917; 313/504, 506; 549/460
See application file for complete search history.

(56) References Cited

U.S. PATENT DOCUMENTS

| | | |
|---|---|---|
| 2010/0001636 A1 | 1/2010 | Yabunouchi |
| 2012/0248426 A1 | 10/2012 | Kato |
| 2014/0183517 A1 | 7/2014 | Huh et al. |
| 2016/0163994 A1* | 6/2016 | Park ....................... C09K 11/06 257/40 |

FOREIGN PATENT DOCUMENTS

| | | | | |
|---|---|---|---|---|
| KR | 10-2013-0028673 A | | 3/2013 | |
| KR | 10-2013-0105192 A | | 9/2013 | |
| KR | 20140087882 A | * | 7/2014 | ............. C09K 11/06 |

* cited by examiner

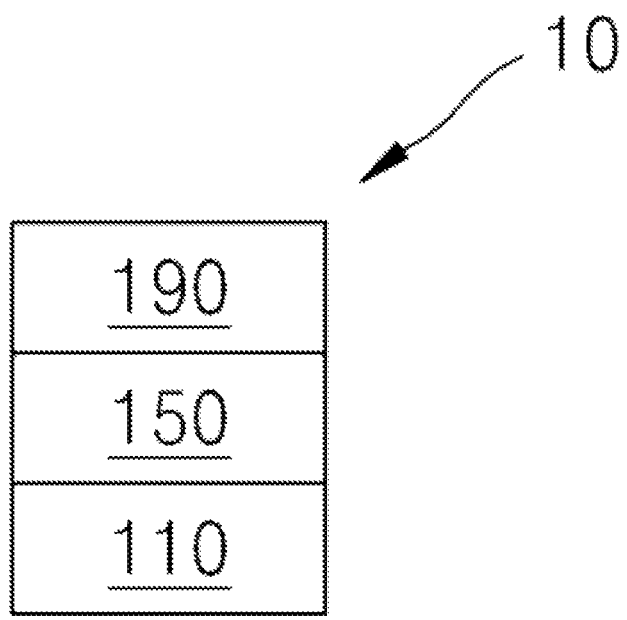

AMINE-BASED COMPOUND AND ORGANIC LIGHT-EMITTING DEVICE INCLUDING THE SAME

CROSS-REFERENCE TO RELATED APPLICATION

Korean Patent Application No. 10-2014-0188647, filed on Dec. 24, 2014, in the Korean Intellectual Property Office, and entitled: "Amine-Based Compound and Organic Light-Emitting Device Including the Same," is incorporated by reference herein in its entirety.

BACKGROUND

1. Field

Embodiments relate to an amine-based compound and an organic light-emitting device including the same.

2. Description of the Related Art

Organic light emitting devices are self-emission devices that have wide viewing angles, high contrast ratios, short response times, and excellent brightness, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, may be recombined in the emission layer to produce excitons. These excitons change from an excited state to a ground state, thereby generating light.

SUMMARY

Embodiments are directed to an amine-based compound and an organic light-emitting device including the same.

According to one or more exemplary embodiments, an aspect provides an amine-based compound represented by Formula 1 below:

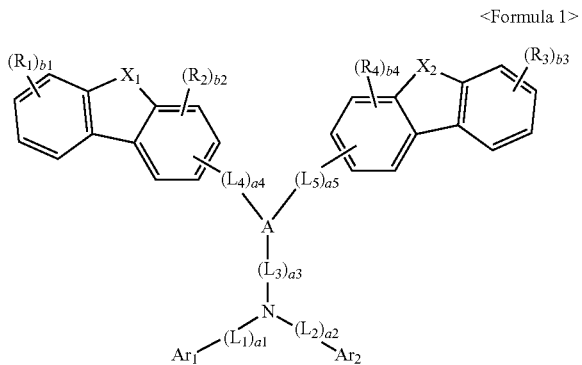

<Formula 1>

$X_1$ to $X_2$ are each independently be O or S;

A is a substituted or unsubstituted $C_6$-$C_{20}$ aromatic ring;

$L_1$ to $L_5$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a5 are each independently selected from 0, 1, 2 and 3, and when a1 is 2 or more, a plurality of $L_1$ are identical or different, when a2 is two or more, a plurality of $L_2$ are identical or different, when a3 is two or more, a plurality of $L_3$ are identical or different, when a4 is two or more, a plurality of $L_4$ are identical or different, and when a5 is two or more, a plurality of $L_5$ are identical or different;

$Ar_1$ and $Ar_2$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group;

$R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthiogroup, a substituted or unsubstituted $C_1$-$C_{60}$ heteroaryl group, a substituted or unsubstituted monovalent non-aromatic condensed polycyclic group, a substituted or unsubstituted monovalent non-aromatic heterocondensed polycyclic group, —Si($Q_1$)($Q_2$)($Q_3$), and —B($Q_4$)($Q_5$);

b1 and b3 are each independently selected from 1, 2, 3 and 4, and b2 and b4 may be each independently selected from 1, 2 and 3, and when b1 is two or more, a plurality of $R_1$ are identical or different, when b2 is two or more, a plurality of $R_2$ are identical or different, when b3 is two or more, a plurality of $R_3$ are identical or different, and when b4 is two or more, a plurality of $R_4$ are identical or different;

at least one substituent of the substituted $C_6$-$C_{20}$ aromatic ring, substituted $C_3$-$C_{20}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), and —B($Q_{14}$)($Q_{15}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —Si($Q_{21}$)($Q_{22}$)($Q_{23}$), and —B($Q_{24}$)($Q_{25}$); and —Si($Q_{31}$)($Q_{32}$)($Q_{33}$) and —B($Q_{34}$)($Q_{35}$), wherein $Q_1$ to $Q_5$, $Q_{11}$ to $Q_{15}$, $Q_{21}$ to $Q_{25}$, and $Q_{31}$ to $Q_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more exemplary embodiments, another aspect provides an organic light-emitting device that includes: a first electrode; a second electrode facing the first electrode; and an organic layer that is disposed between the first electrode and the second electrode and includes an emission layer, wherein the organic layer includes at least one of the amine-based compound described above.

BRIEF DESCRIPTION OF THE DRAWING

Features will be apparent to those of skill in the art by describing in detail exemplary embodiments with reference to the attached drawing in which:

FIG. 1 illustrates a schematic view of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

An amine-containing (e.g., tertiary amine) or amine-based compound according to an embodiment may be represented by Formula 1 below.

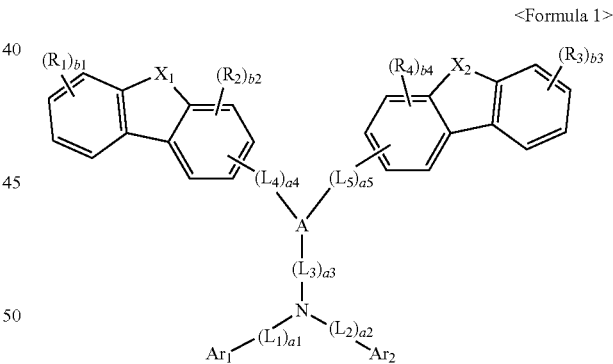

<Formula 1>

In Formula 1, $X_1$ and $X_2$ may each independently be, e.g., O or S.

For example, $X_1$ and $X_2$ may be identical or different.

In Formula 1, A may be or may include, e.g., a substituted or unsubstituted $C_6$-$C_{20}$ aromatic ring.

In an implementation, A may be selected from or may include, e.g., a substituted or unsubstituted benzene, a substituted or unsubstituted naphthalene, a substituted or unsubstituted anthracene, a substituted or unsubstituted pyrene, a substituted or unsubstituted phenanthrene, a substituted or unsubstituted chrysene, and a substituted or unsubstituted triphenylene.

In an implementation, A may be, e.g., a group represented by one of the following Formulae 2-1 to 2-19.

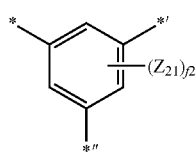
Formula 2-1
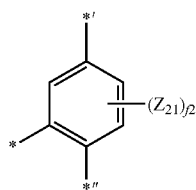
Formula 2-2
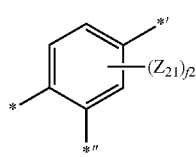
Formula 2-3
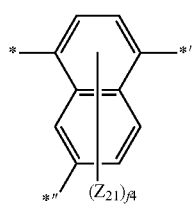
Formula 2-4
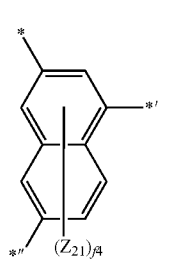
Formula 2-5
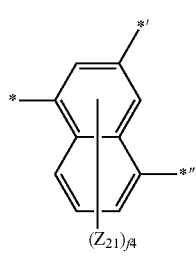
Formula 2-6
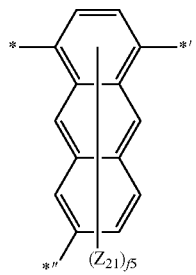
Formula 2-7
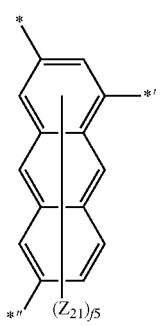
Formula 2-8
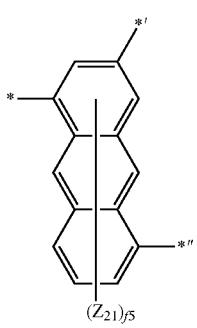
Formula 2-9
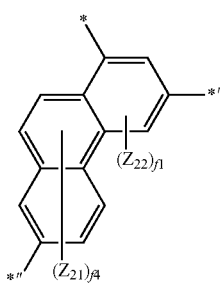
Formula 2-10
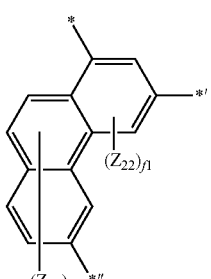
Formula 2-11
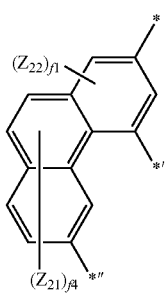
Formula 2-12

Formula 2-13

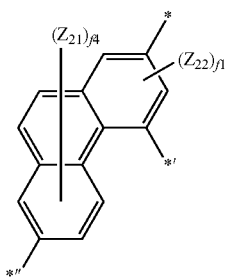

Formula 2-14

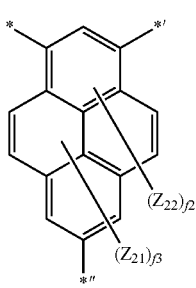

Formula 2-15

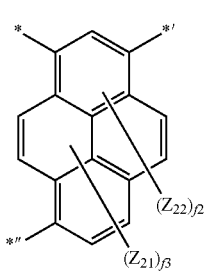

Formula 2-16

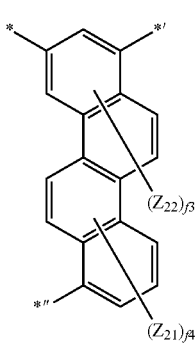

Formula 2-17

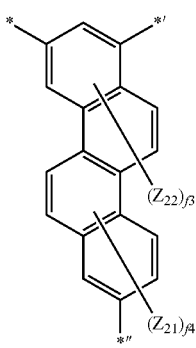

Formula 2-18

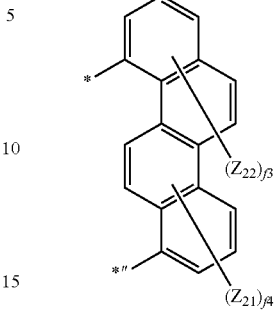

Formula 2-19

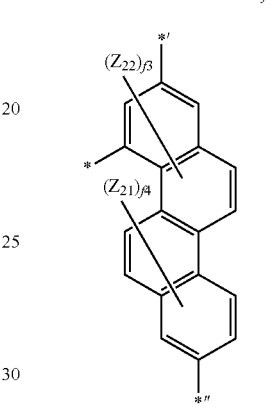

In Formulae 2-1 to 2-19, $Z_{21}$ to $Z_{22}$ may each independently be selected from, e.g., a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In an implementation, f1 may be 1 or 2, f2 may be an integer of 1 to 3, f3 may be an integer of 1 to 4, f4 may be an integer of 1 to 5, and f5 may be an integer of 1 to 7.

Each of * and *' indicates a binding site to a neighboring atom, and *'' indicates a binding site to $L_3$ in -$(L_3)_{a3}$- or N. Additional descriptions of $L_3$ and a3 will be provided below.

$L_1$ and $L_5$ in Formula 1 may each independently be selected from or include, e.g., a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In an implementation, $L_1$ to $L_5$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, a isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, ovalenylene group, a pyrrolylene group, a thiophenylene group, a furanylene group, an imidazolylene group, a pyrazolylene group, a thiazolylene group, an isothiazolylene group, an oxazolylene group, a isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In an implementation, $L_1$ to $L_5$ in Formula 1 may be a group represented by one of the following Formulae 3-1 to 3-33.

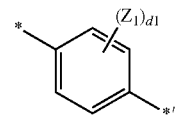

Formula 3-1

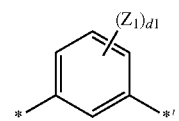

Formula 3-2

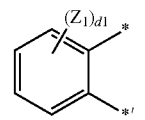

Formula 3-3

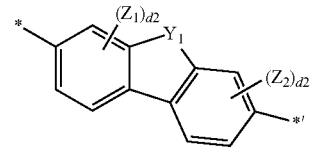

Formula 3-4

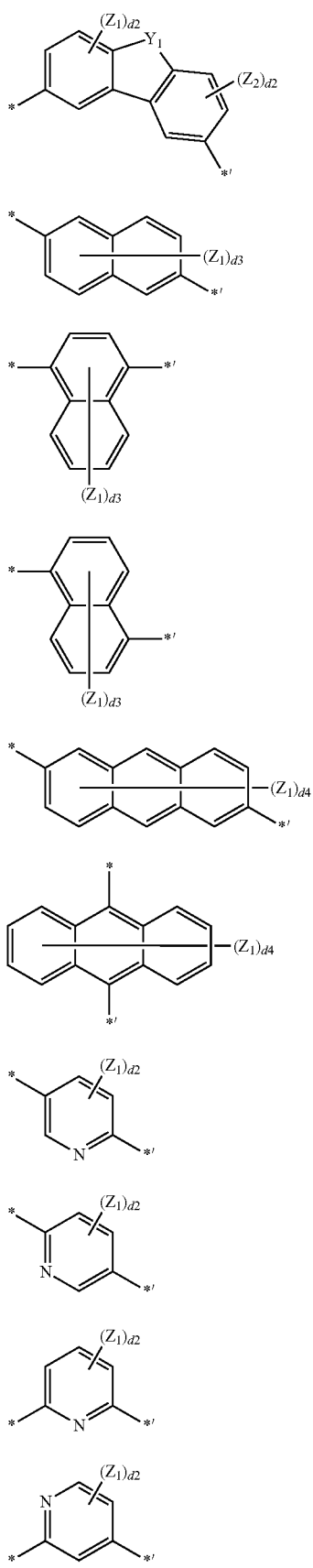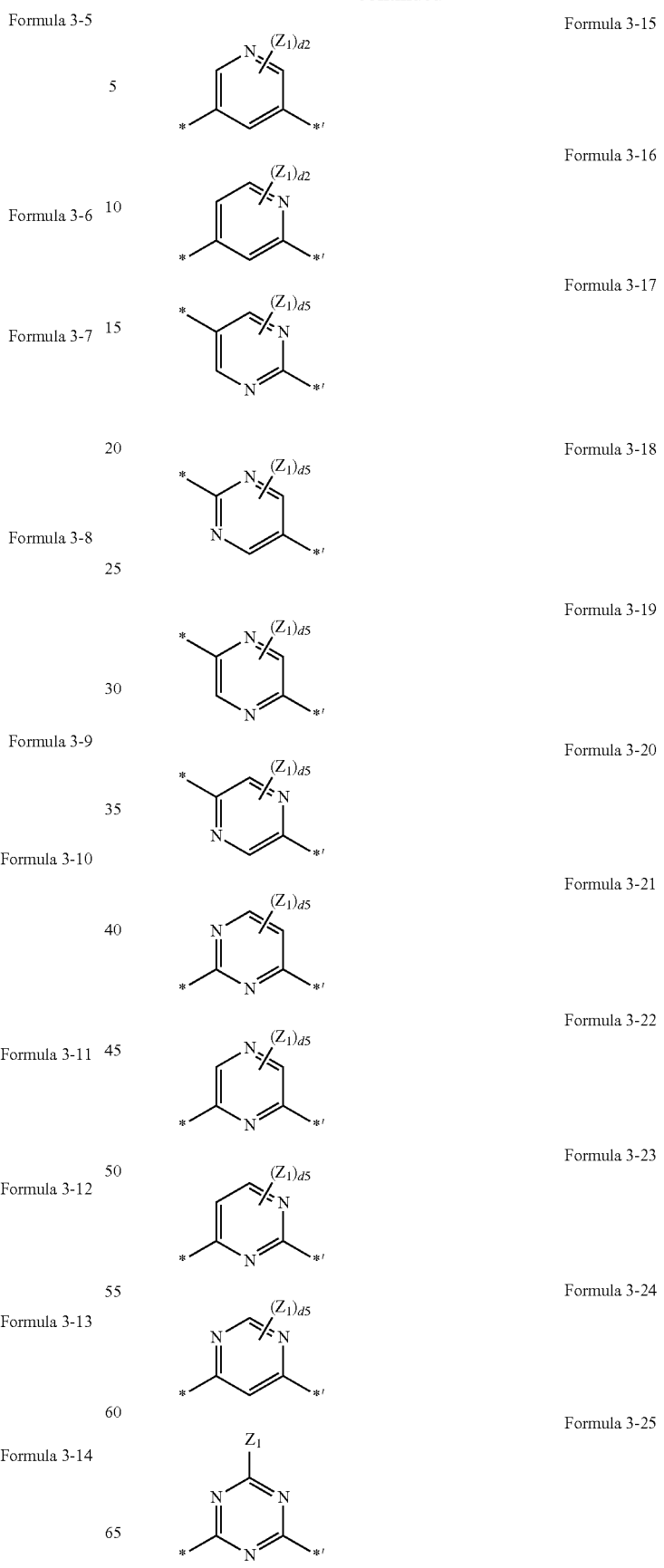

-continued

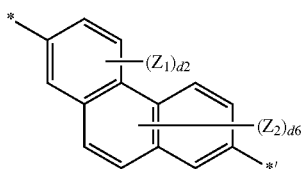
Formula 3-26

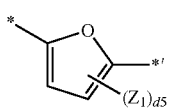
Formula 3-27

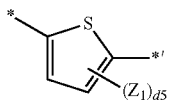
Formula 3-28

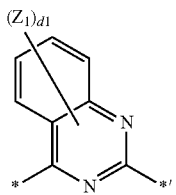
Formula 3-29

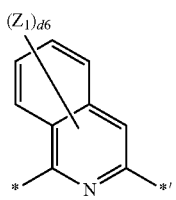
Formula 3-30

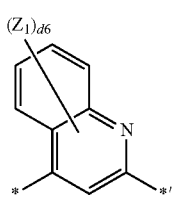
Formula 3-31

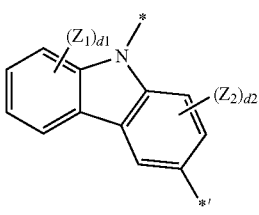
Formula 3-32

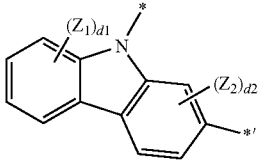
Formula 3-33

In Formulae 3-1 to 3-33, $Y_1$ may be O, S, $C(Z_3)(Z_4)$, $N(Z_5)$, or $Si(Z_6)(Z_7)$.

$Z_1$ to $Z_7$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzo-fluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

d1 may be an integer of 1 to 4, d2 may be an integer of 1 to 3, d3 may be an integer of 1 to 6, d4 may be an integer of 1 to 8, d5 may be 1 or 2, and d6 may be an integer of 1 to 5, and each of * and *' indicates a binding site to a neighboring atom.

a1, a2, a3, a4, and a5 in Formula 1 each indicate the number of $L_1$, $L_2$, $L_3$, $L_4$ and $L_5$ respectively, and may each independently be selected from 0, 1, 2 and 3. For example, a1, a2, a4 and a5 may each independently be 0 or 1, and a3 may be 0, 1 or 2. When a1, a2, a3, a4 or a5 is 0, *-$(L_1)a_1$-*', *-$(L_2)a_2$-*', *-$(L_3)a_3$-*', *-$(L_4)a_4$-*' or *-$(L_5)a_5$-*' is a single bond, and when a1, a2, a3, a4 or a5 is 2 or more, a plurality of $L_1$, $L_2$, $L_3$, $L_4$ or $L_5$ may be identical or different.

*-$(L_1)a_1$-*', *-$(L_2)a_2$-*', *-$(L_3)a_3$-*', *-$(L_4)a_4$-*' and *-$(L_5)a_5$-*' in Formula 1 may each independently be a single bond or a group represented by one of the following Formulae 4-1 to 4-26.

Formula 4-1

Formula 4-2

Formula 4-3

Formula 4-4

Formula 4-5

Formula 4-6

Formula 4-7

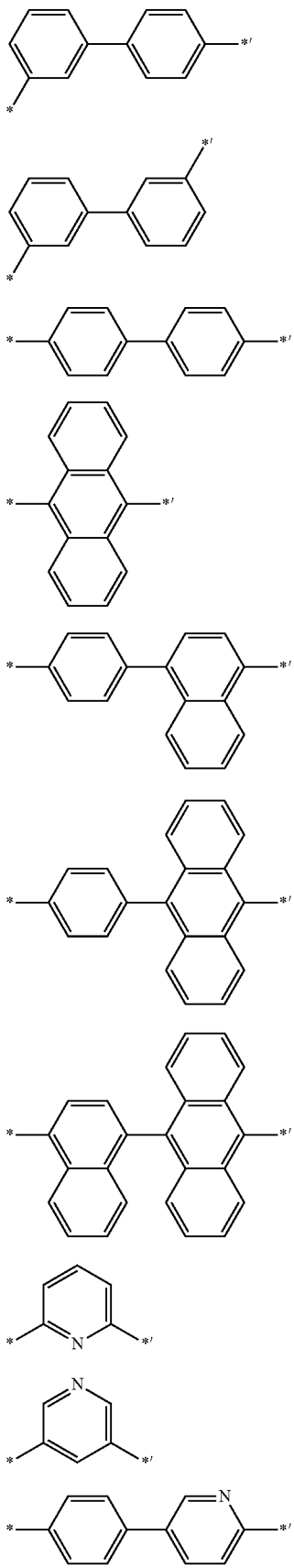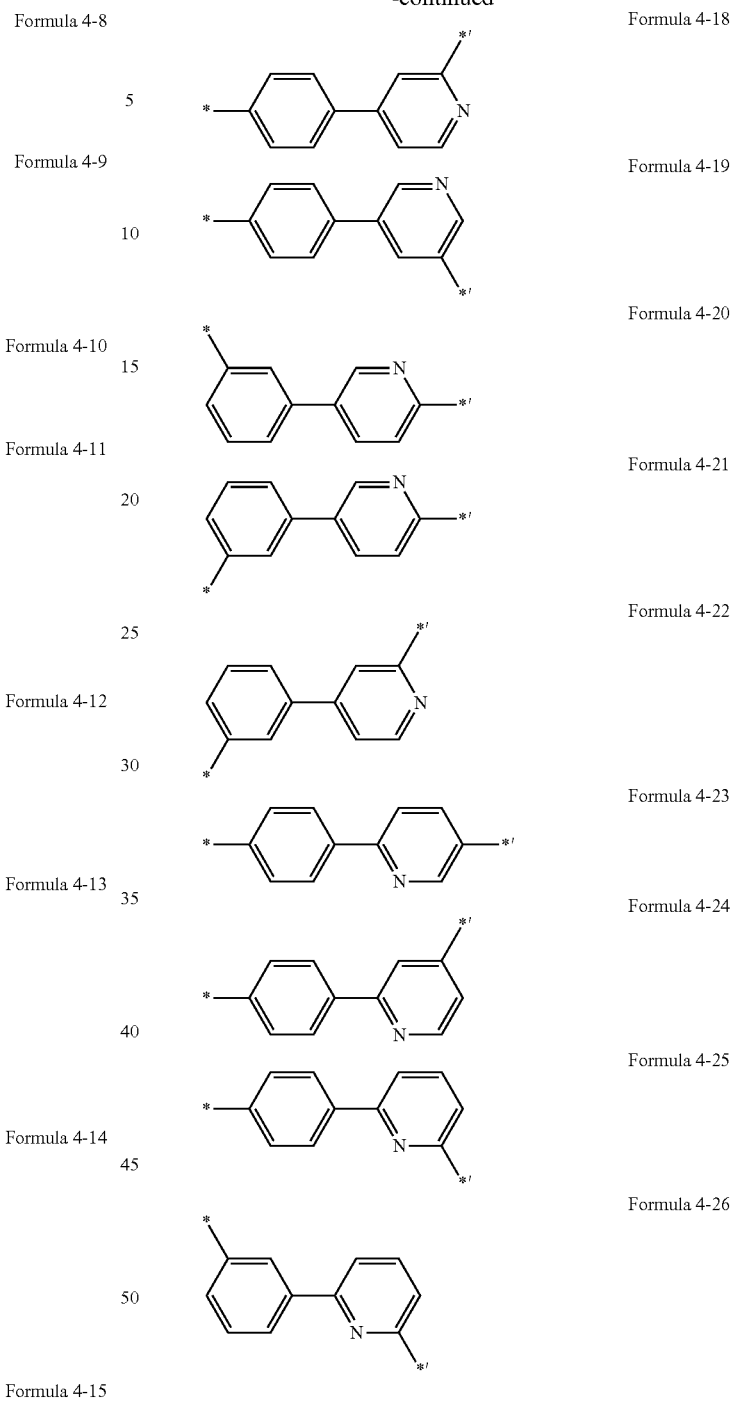

Each of * and *' in Formulae 4-1 to 4-26 indicates a binding site to a neighboring atom.

$Ar_1$ and $Ar_2$ in Formula 1 may each independently be selected from or include, e.g., a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group.

In an implementation, $Ar_1$ and $Ar_2$ may each independently be selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group and a dibenzocarbazolyl group, a thiadiazolyl group, an imidazopyridinyl group, an imidazopyrimidinyl group, and —Si($Q_{31}$)($Q_{32}$)($Q_{33}$);

wherein $Q_{31}$ to $Q_{33}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In an implementation, $Ar_1$ and $Ar_2$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group and a dibenzocarbazolyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group, a dibenzocarbazolyl group, and —Si($Q_{31}$)($Q_{32}$)($Q_{33}$), wherein $Q_{31}$ to $Q_{33}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In an implementation, $Ar_1$ and $Ar_2$ may each independently be a group represented by one of the following Formulae 5-1 to 5-14.

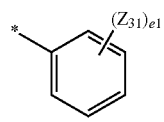

Formula 5-1

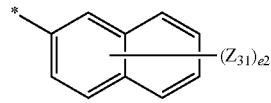

Formula 5-2

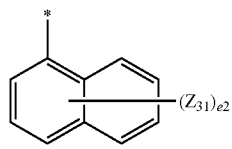

Formula 5-3

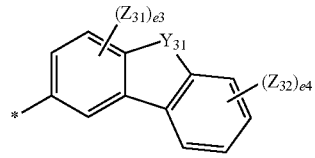

Formula 5-4

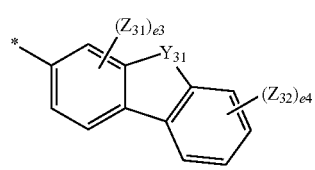

Formula 5-5

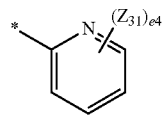

Formula 5-6

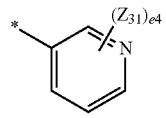

Formula 5-7

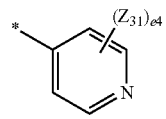

Formula 5-8

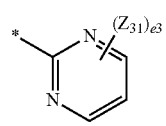

Formula 5-9

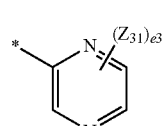

Formula 5-10

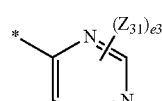

Formula 5-11

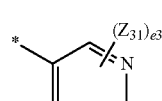

Formula 5-12

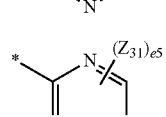

Formula 5-13

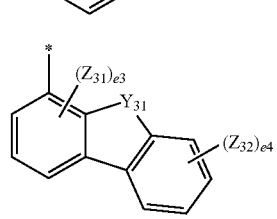

Formula 5-14

In Formulae 5-1 to 5-14, $Y_{31}$ may be C($Z_{33}$)($Z_{34}$) or N($Z_{35}$).

$Z_{31}$ to $Z_{35}$ may each independently be selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group, and a dibenzocarbazolyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group and a naphthyl group; and —Si($Q_{31}$)($Q_{32}$)($Q_{33}$), wherein $Q_{31}$ to $Q_{33}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$ to $C_{20}$ alkyl group, a $C_1$ to $C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

e1 may be an integer of 1 to 5; e2 may be an integer of 1 to 7; e3 may be an integer of 1 to 3; e4 may be an integer of 1 to 4; e5 may be an integer of 1 or 2; and * indicates a binding site to a neighboring atom.

In an implementation, $Ar_1$ and $Ar_2$ may each independently be a group represented by one of the following Formulae 6-1 to 6-21.

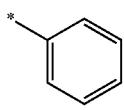

Formula 6-1

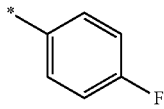

Formula 6-2

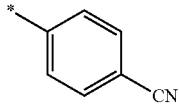

Formula 6-3

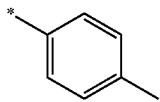

Formula 6-4

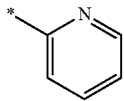

Formula 6-5

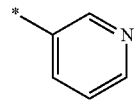

Formula 6-6

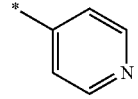

Formula 6-7

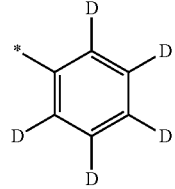

Formula 6-8

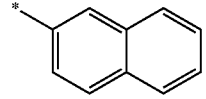

Formula 6-9

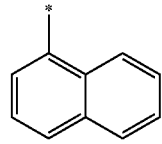

Formula 6-10

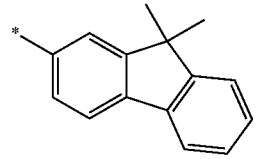

Formula 6-11

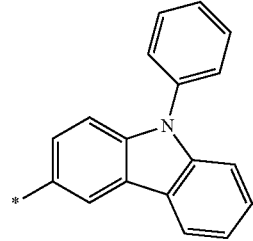

Formula 6-12

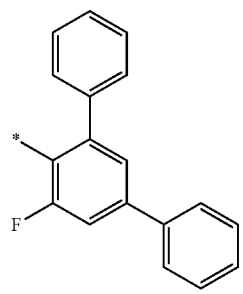

Formula 6-13

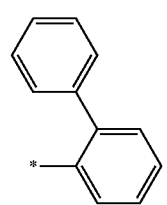

Formula 6-14

-continued

Formula 6-15
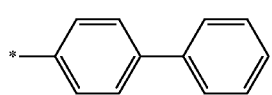

Formula 6-16
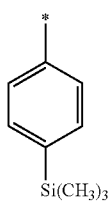

Formula 6-17
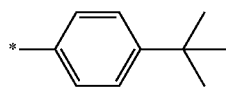

Formula 6-18
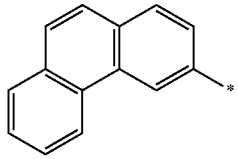

Formula 6-19
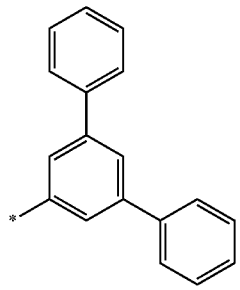

Formula 6-20
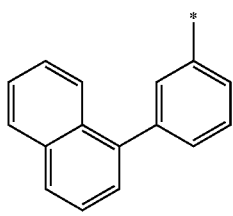

Formula 6-21
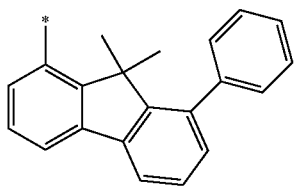

* in Formulae 6-1 to 6-21 indicates a binding site to a neighboring atom.

$R_1$ to $R_4$ in Formula 1 may each independently be selected from or include, e.g., a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthiogroup, a substituted or unsubstituted $C_1$-$C_{60}$ heteroaryl group, a substituted or unsubstituted monovalent non-aromatic condensed polycyclic group, a substituted or unsubstituted monovalent non-aromatic heterocondensed polycyclic group, —Si($Q_1$)($Q_2$)($Q_3$), and —B($Q_4$)($Q_5$).

In an implementation, $R_1$ to $R_4$ may each independently be selected from or include, e.g., a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$).

In an implementation, $R_1$ to $R_4$ may each independently be selected from or include, e.g., a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, and a substituted or unsubstituted $C_1$-$C_{20}$ alkoxy group.

b1, b2, b3, and b4 in Formula 1 each indicate the number of $R_1$, $R_2$, $R_3$, and $R_4$ respectively. b1 and b3 may each independently be selected from 1, 2, 3 and 4, and b2 and b4 may each independently be selected from 1, 2 and 3. When b1, b2, b3, or b4 is 2 or more, a plurality of $R_1$, $R_2$, $R_3$, or $R_4$ may be identical or different.

In an implementation, the amine-based compound represented by Formula 1 may be represented by one of the following Formulae 1A to 1F.

<Formula 1A>

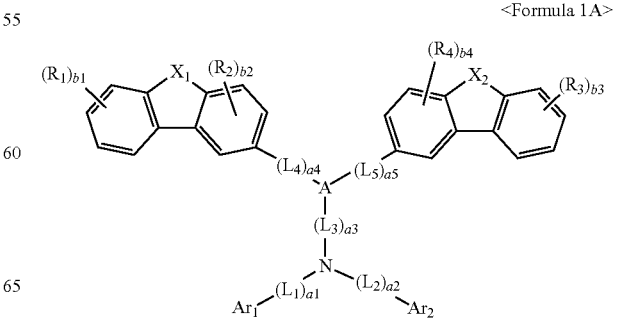

<Formula 1B>

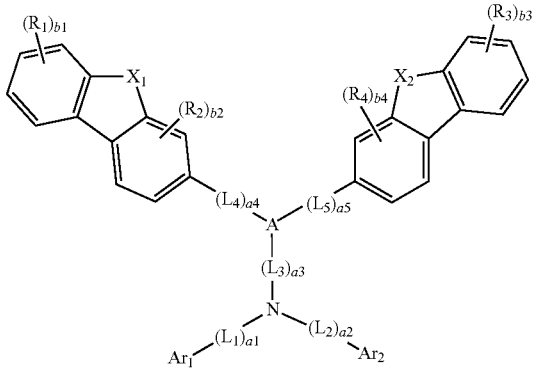

<Formula 1C>

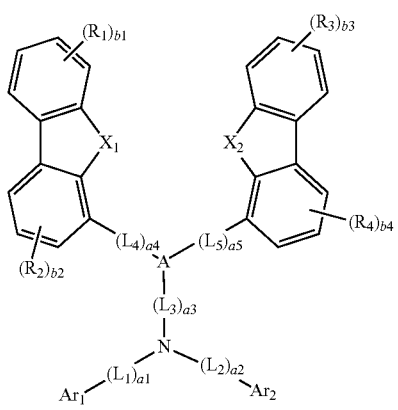

<Formula 1D>

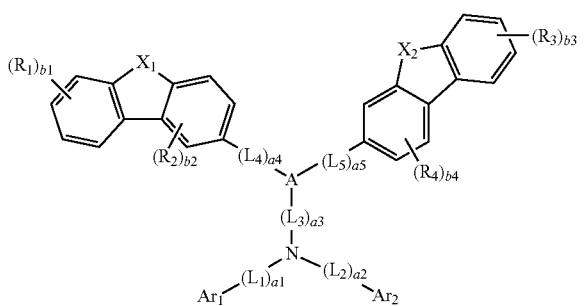

<Formula 1E>

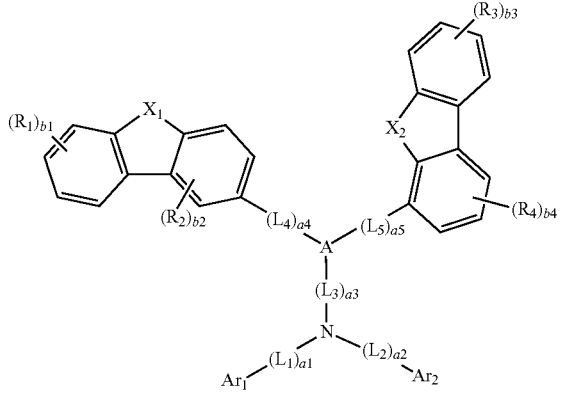

<Formula 1F>

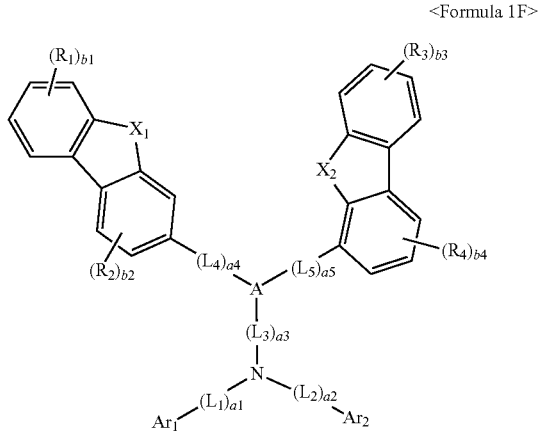

$X_1$, $X_2$, A, $L_1$ to $L_5$, a1 to a5, $Ar_1$, $Ar_2$, $R_1$ to $R_4$ and b1 to b4 of Formulae 1A to 1F may be defined the same as $X_1$, $X_2$, A, $L_1$ to $L_5$, a1 to a5, $Ar_1$, $Ar_2$, $R_1$ to $R_4$ and b1 to b4 of Formula 1.

In an implementation, the amine-based compound represented by Formula 1 may be represented by one of Formulae 1A to 1C.

In an implementation, the amine-based compound represented by Formula 1 may be represented by one of the following Formulae 1A(1) to 1A(3), 1B(1) to 1B(3), 1C(1) to 1C(3), 1D(1) to 1D(3), 1E(1) to 1E(3) and 1F(1) to 1F(3).

<Formula 1A(1)>

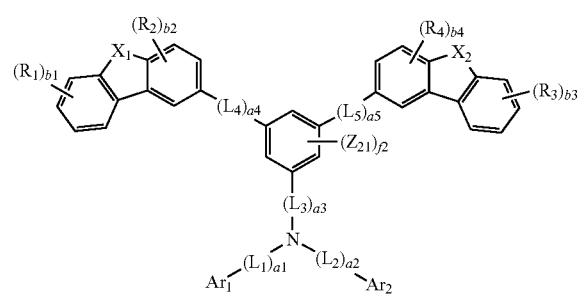

<Formula 1A(2)>

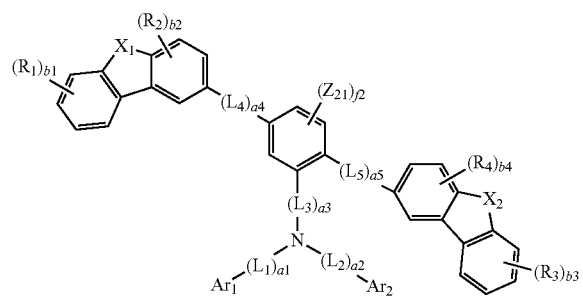

<Formula 1A(3)>
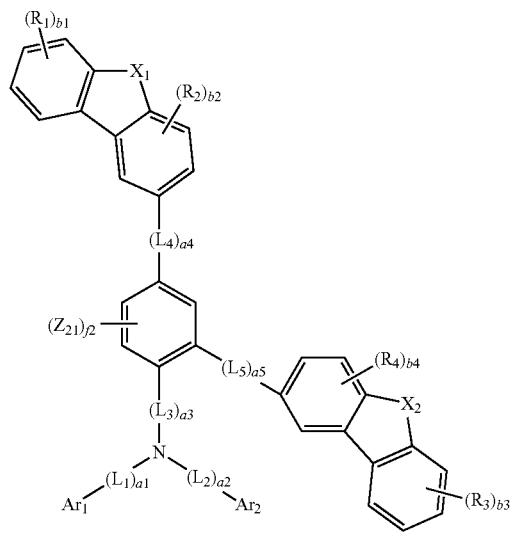
<Formula 1B(1)>
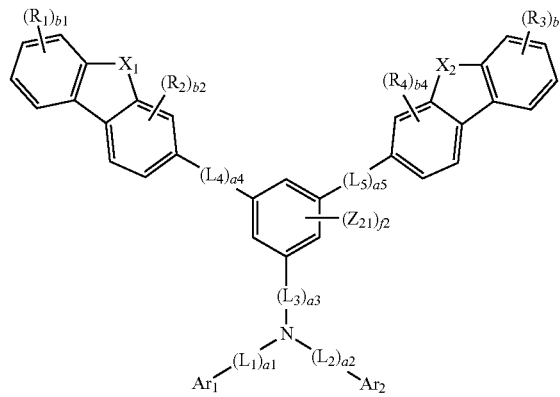
<Formula 1B(2)>
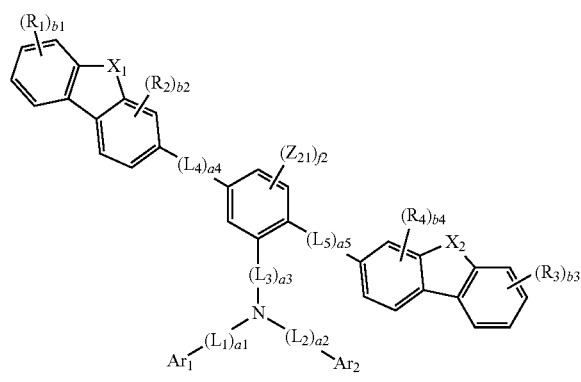
<Formula 1B(3)>
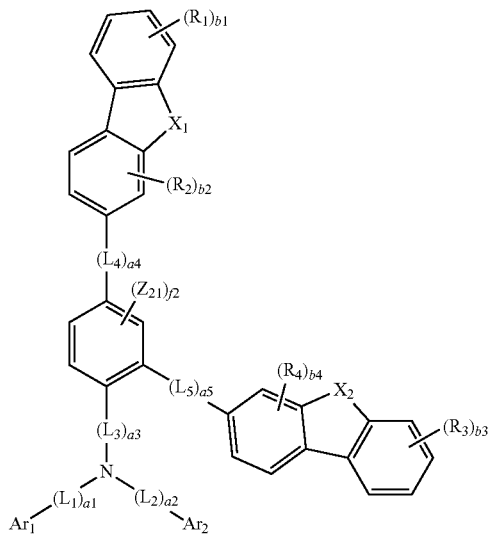
<Formula 1C(1)>
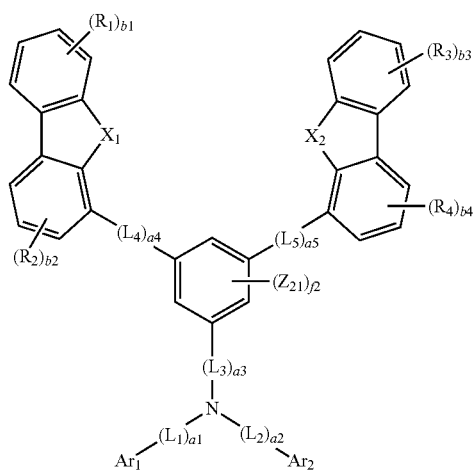
<Formula 1C(2)>
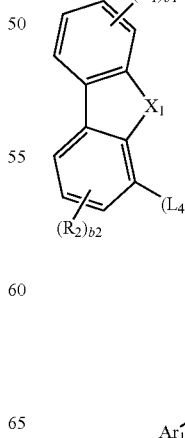

<Formula 1C(3)>
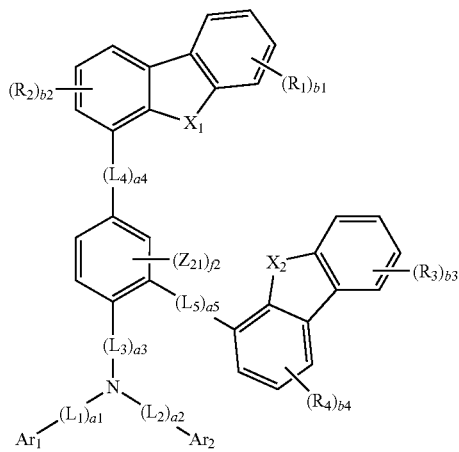
<Formula 1D(3)>
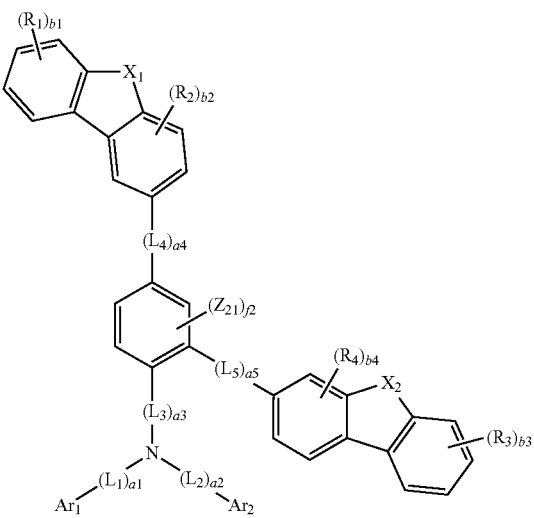
<Formula 1D(1)>
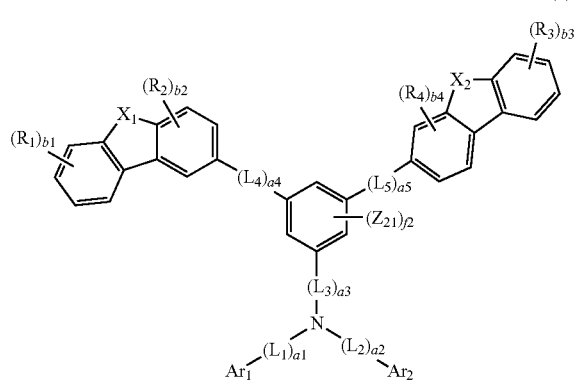
<Formula 1E(1)>
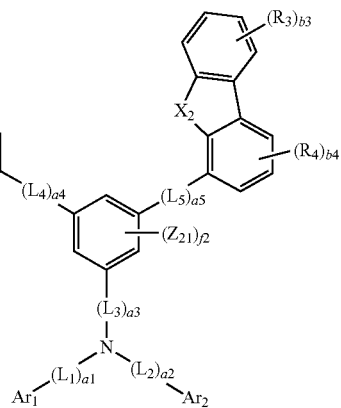
<Formula 1D(2)>
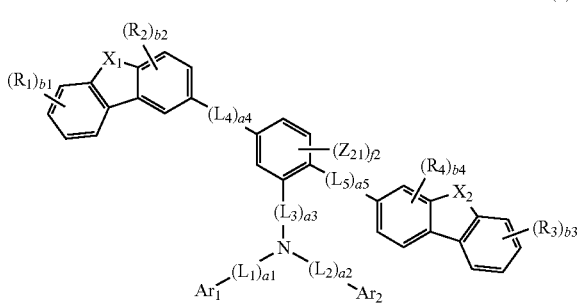
<Formula 1E(2)>
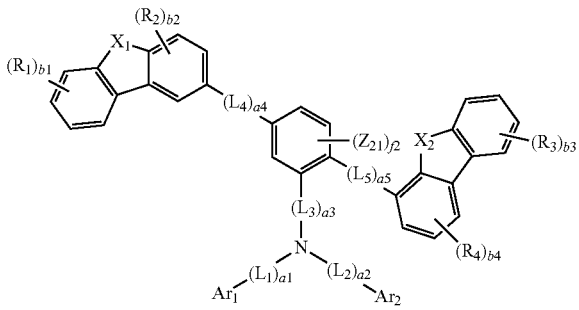

<Formula 1E(3)>

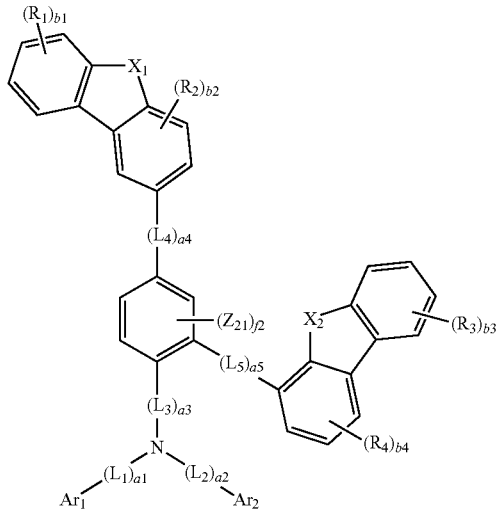

<Formula 1F(1)>

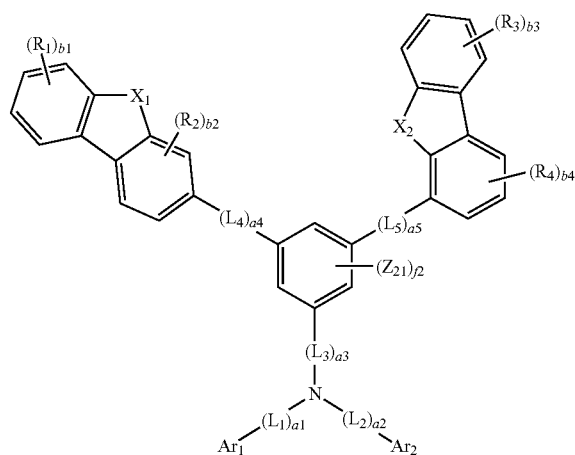

<Formula 1F(2)>

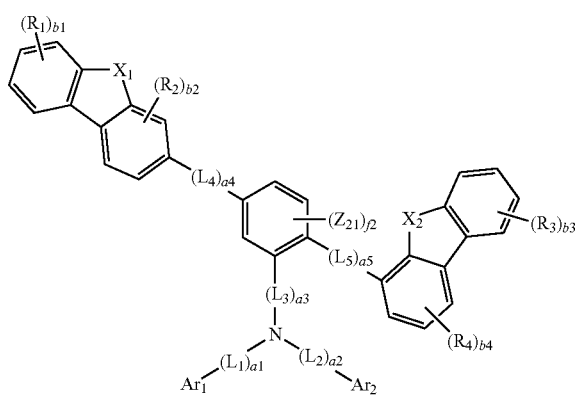

<Formula 1F(3)>

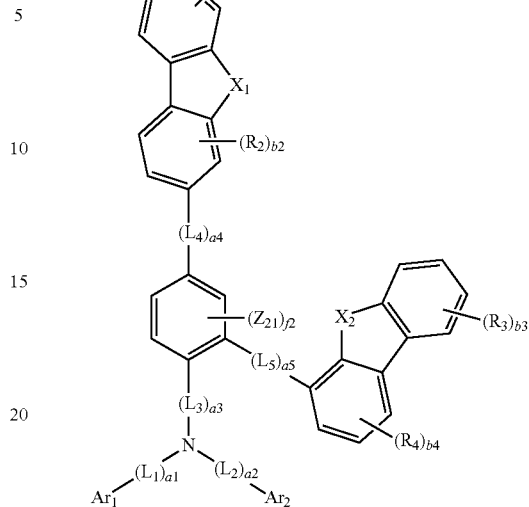

$X_1$, $X_2$, $L_1$ to $L_5$, a1 to a5, $Ar_1$, $Ar_2$, $R_1$ to $R_4$ and b1 to b4 of Formulae 1A(1) to 1A(3), 1B(1) to 1B(3), 1C(1) to 1C(3), 1D(1) to 1D(3), 1E(1) to 1E(3) and 1F(1) to 1F(3) may be defined the same as $X_1$, $X_2$, $L_1$ to $L_5$, a1 to a5, $Ar_1$, $Ar_2$, $R_1$ to $R_4$ and b1 to b4 of Formula 1. $Z_{21}$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group; and f2 may be an integer of 1 to 3.

In an implementation, $L_1$ to $L_5$ in Formulae 1A(1) to 1A(3), 1B(1) to 1B(3), 1C(1) to 1C(3), 1D(1) to 1D(3), 1E(1) to 1E(3) and 1F(1) to 1F(3) may each independently be a group represented by one of Formulae 4-1 to 4-26, above; a1, a2, a4 and a5 may each independently be 0 or 1, and a3 may be 0, 1 or 2.

In an implementation, in Formulae 1A(1) to 1A(3), 1B(1) to 1B(3), 1C(1) to 1C(3), 1D(1) to 1D(3), 1E(1) to 1E(3) and 1F(1) to 1F(3), a1, a2, a4 and a5 may each independently be be 0 or 1, and a3 may be 0, 1 or 2;

$Ar_1$ and $Ar_2$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, dibenzofluorenyl group, a phenanthrenyl group, an anthracenyl group, a pyrenyl group, a chrysenyl group and —Si($Q_{31}$)($Q_{32}$)($Q_{33}$);

wherein $Q_{31}$ to $Q_{33}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group and a chrysenyl group.

In an implementation, the amine-based compound represented by Formula 1 may be one of the following Compounds 1 to 144.

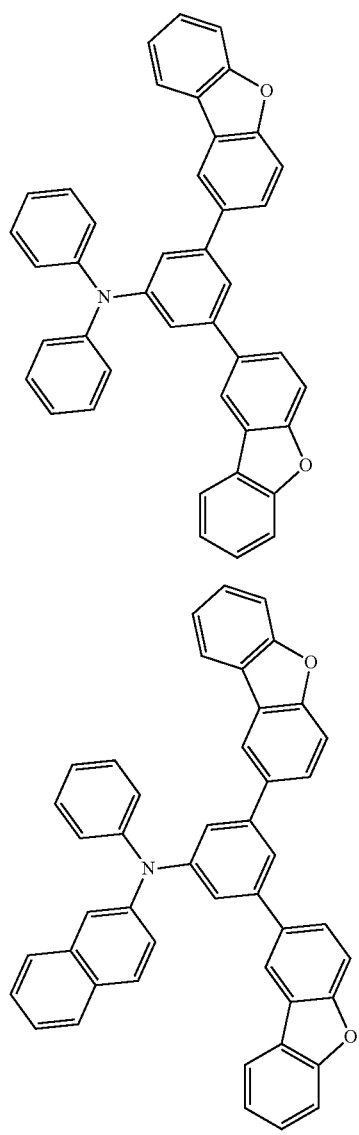

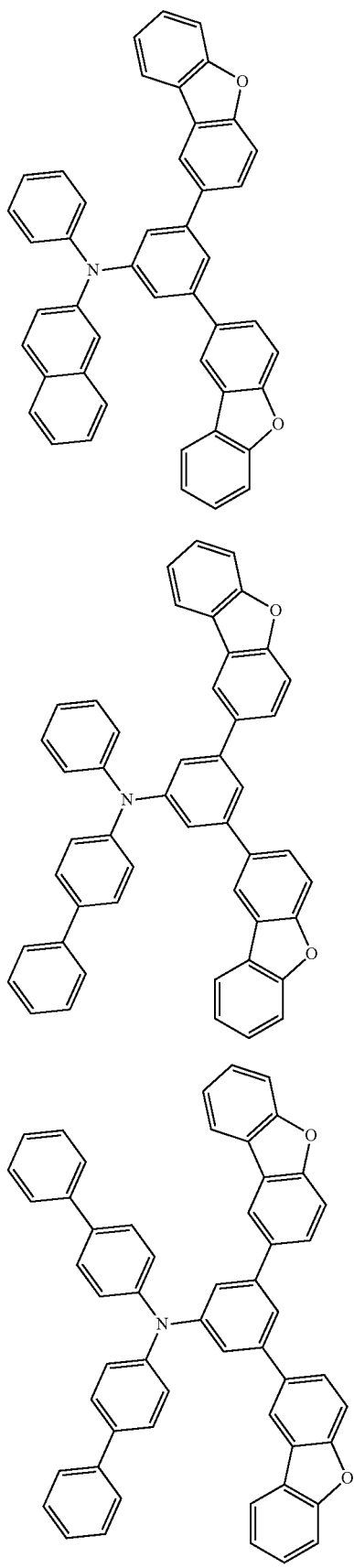

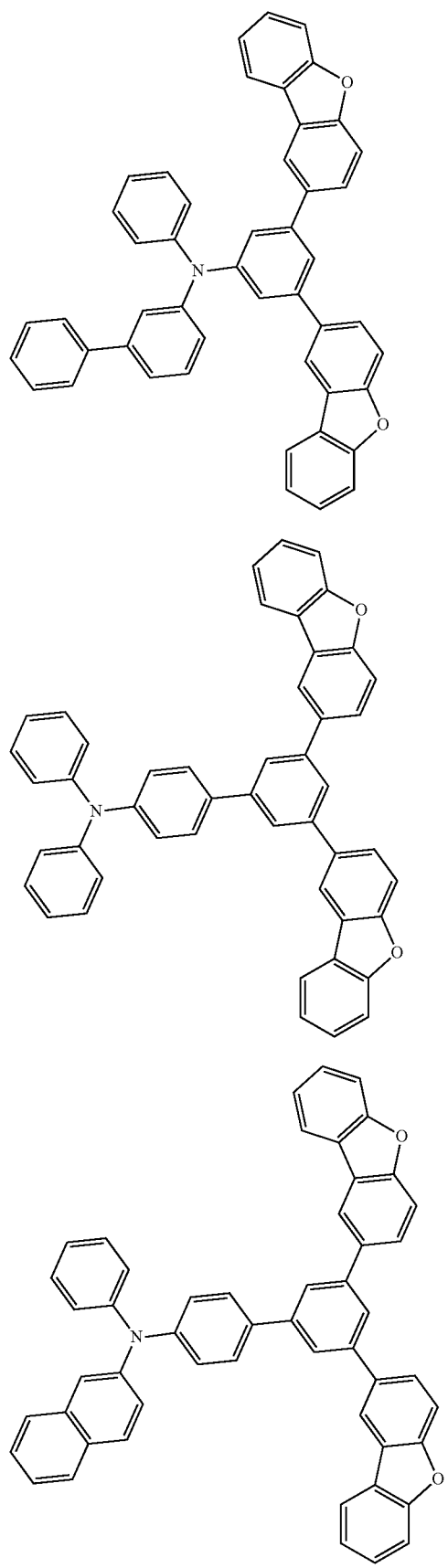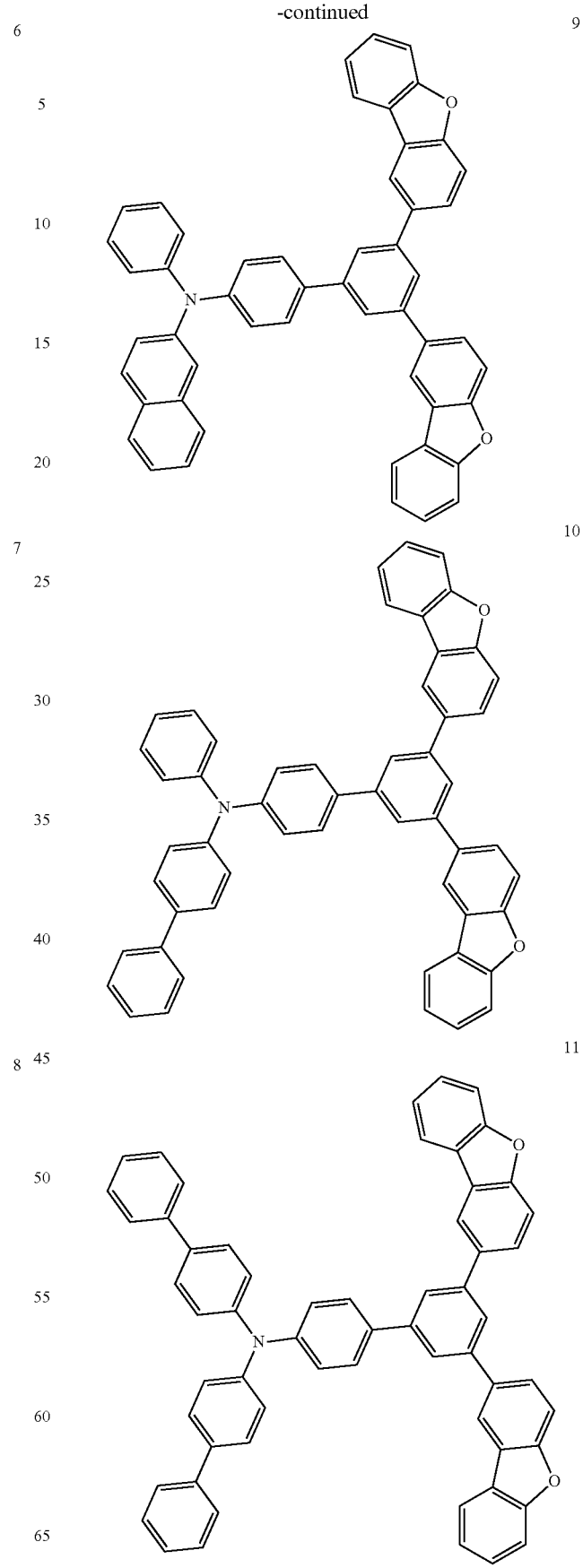

12
-continued
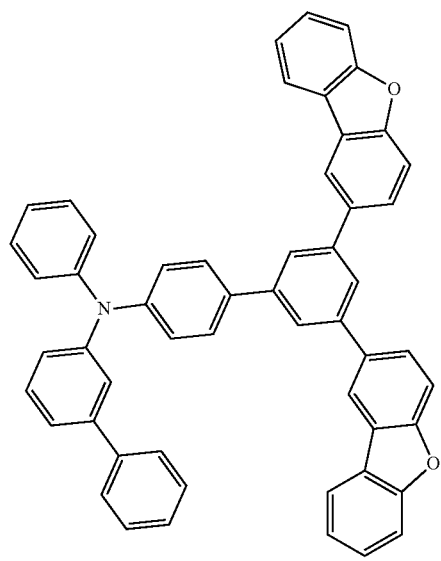
13
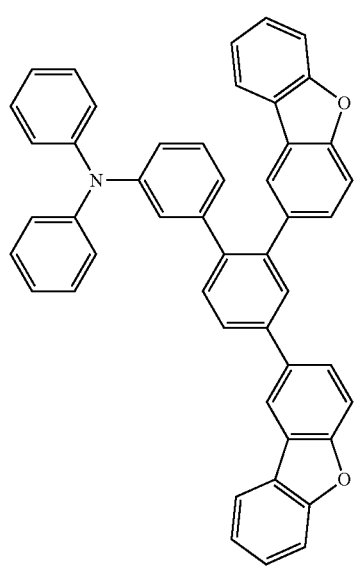
14
-continued
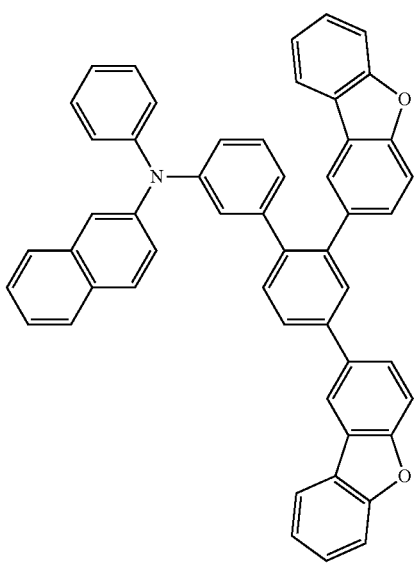
15
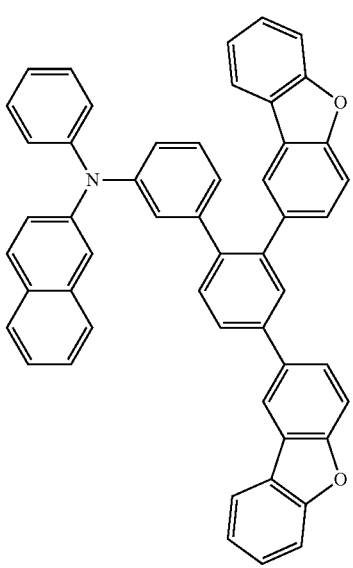

16
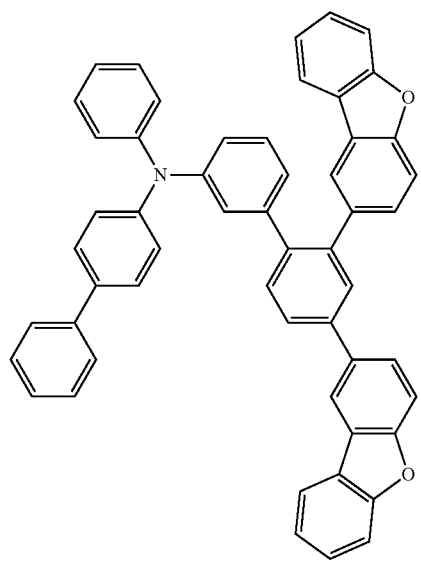
17
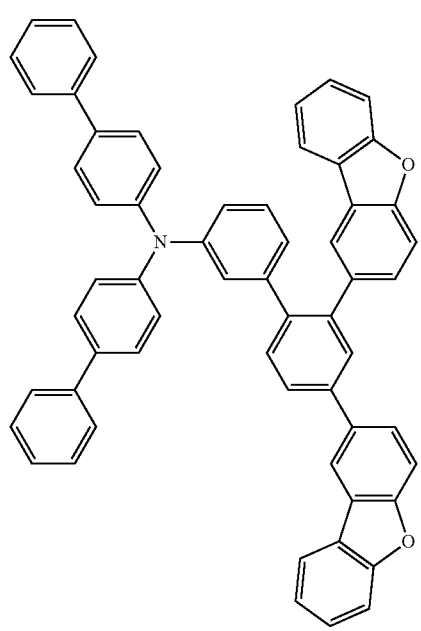
18
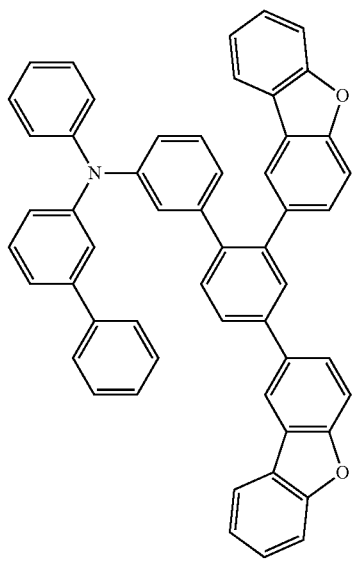
19
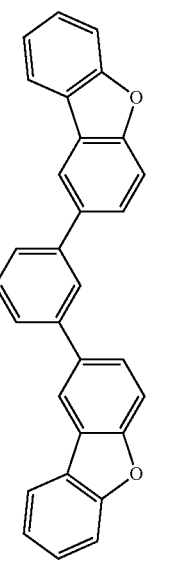

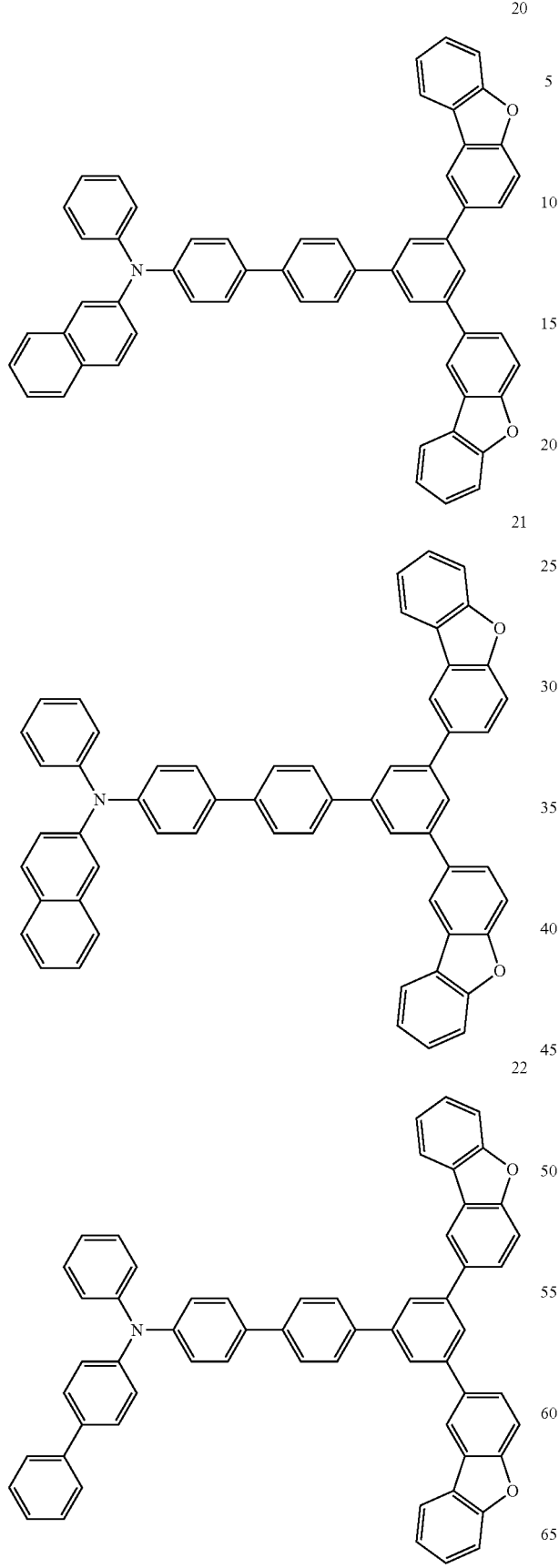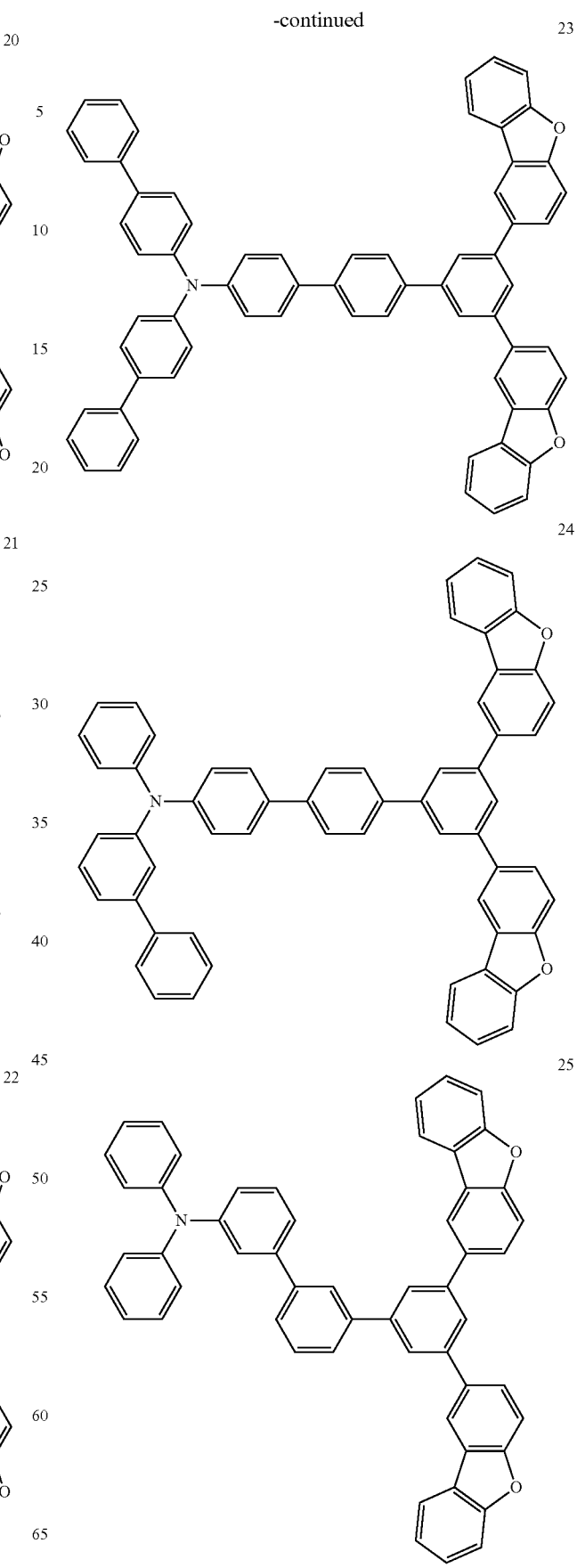

26
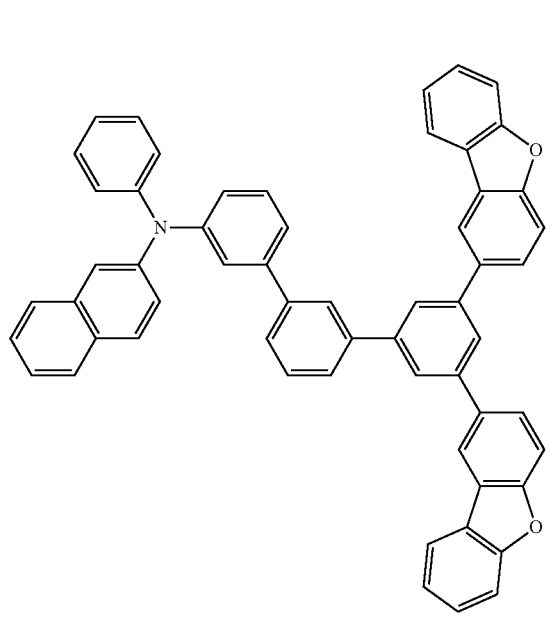
27
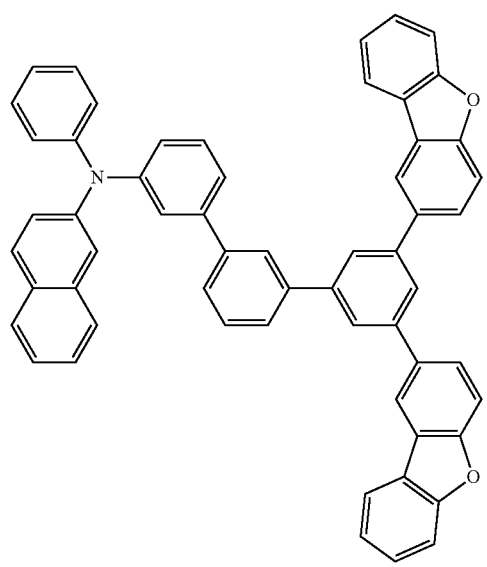
28
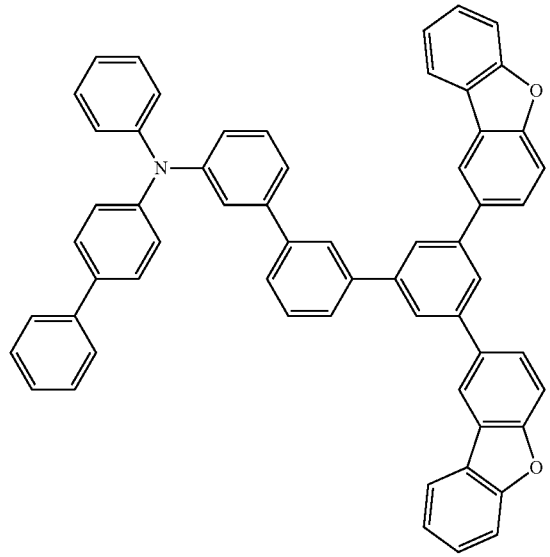
29
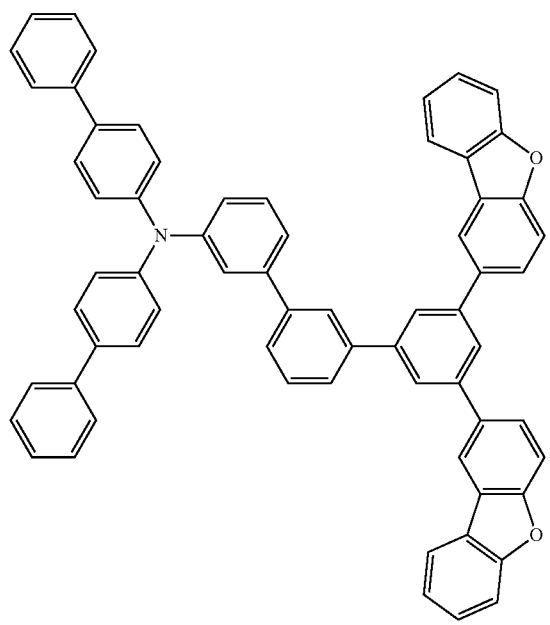

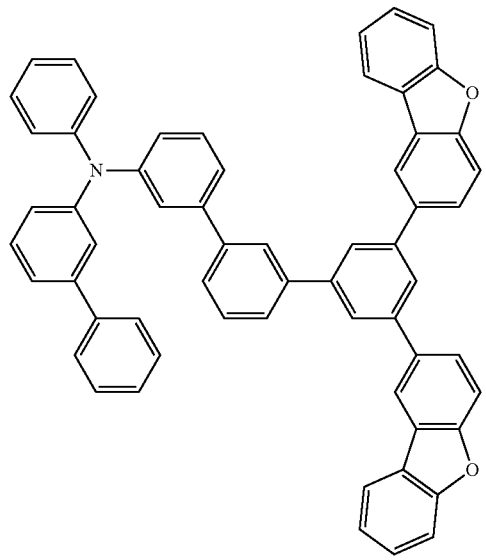
30
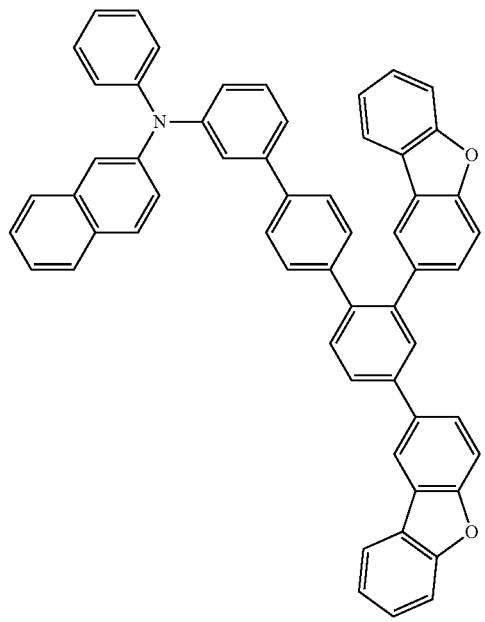
32
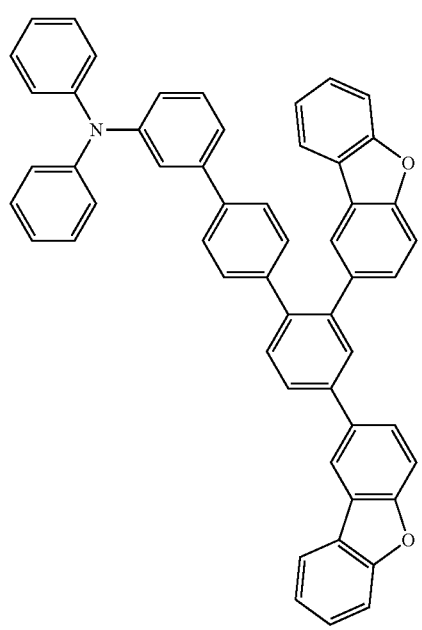
31
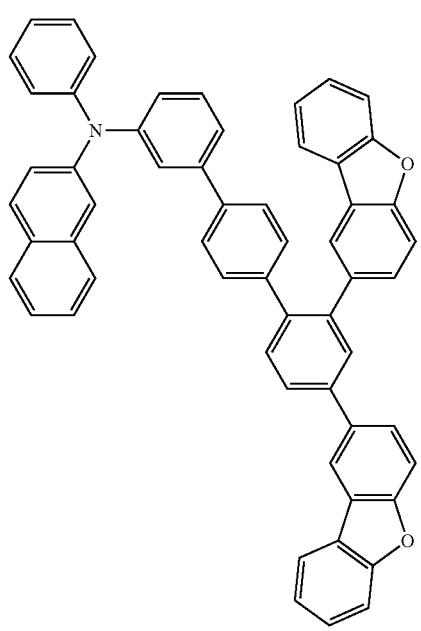
33

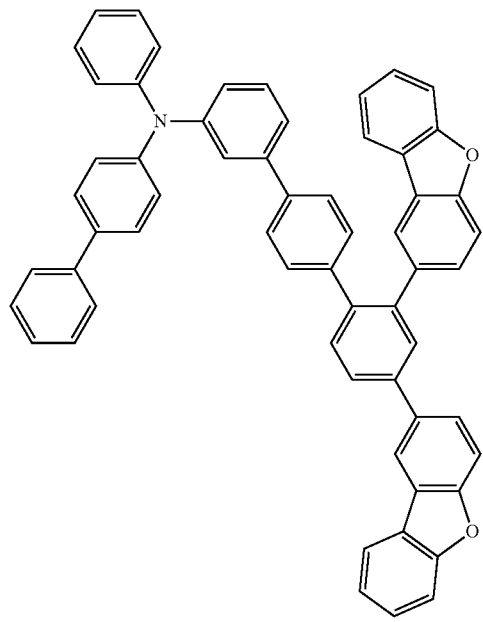
34
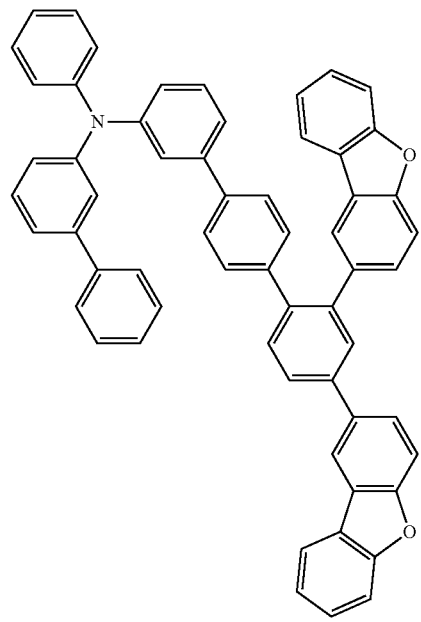
36
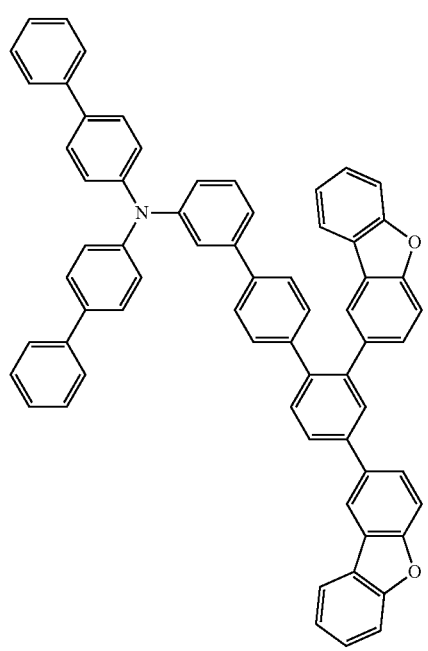
35
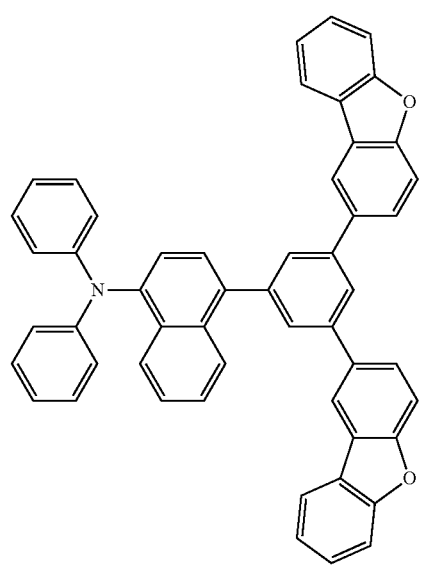
37

38
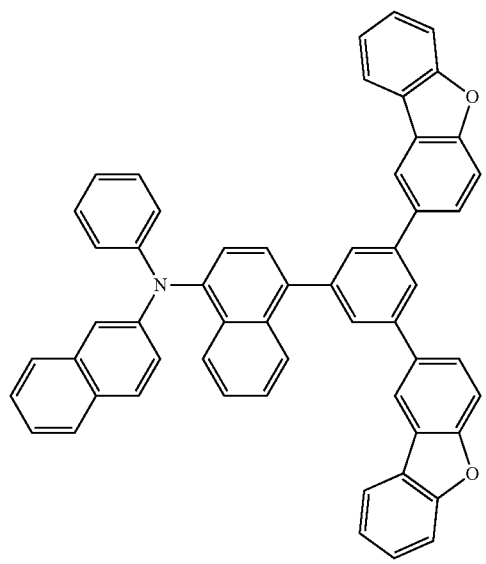
39
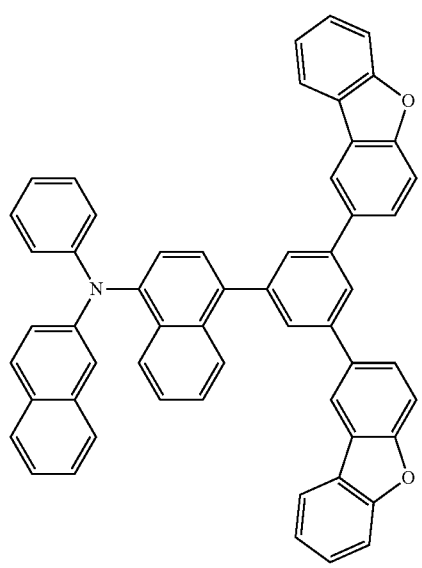
40
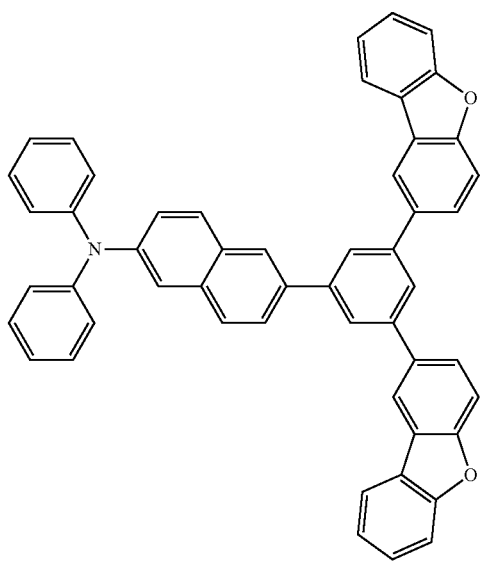
41
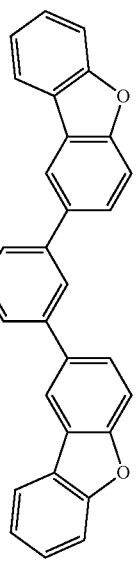

42
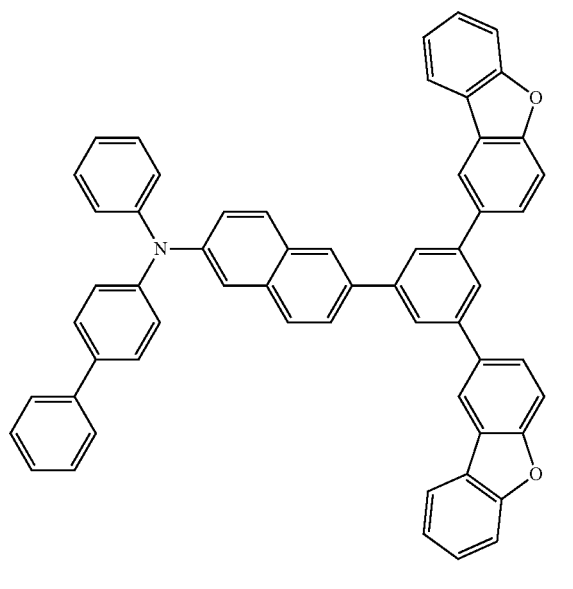
43
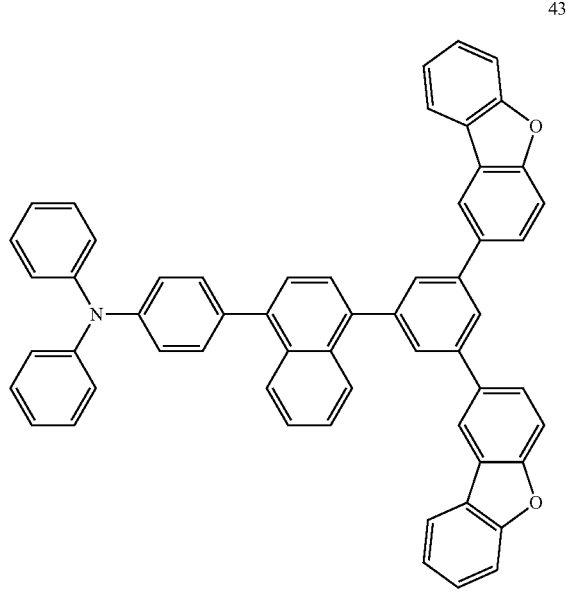
44
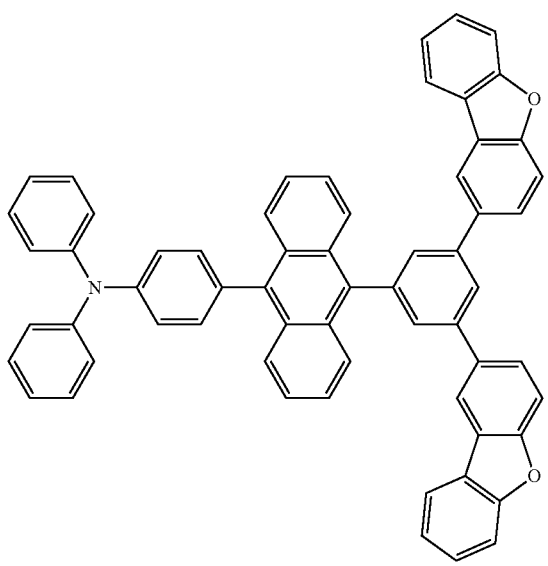
45
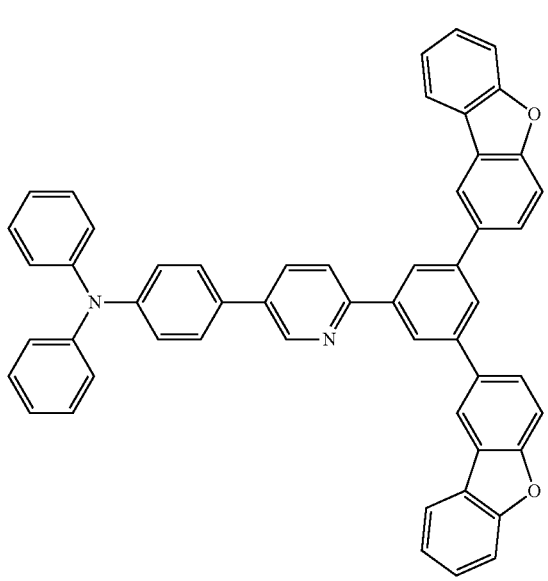

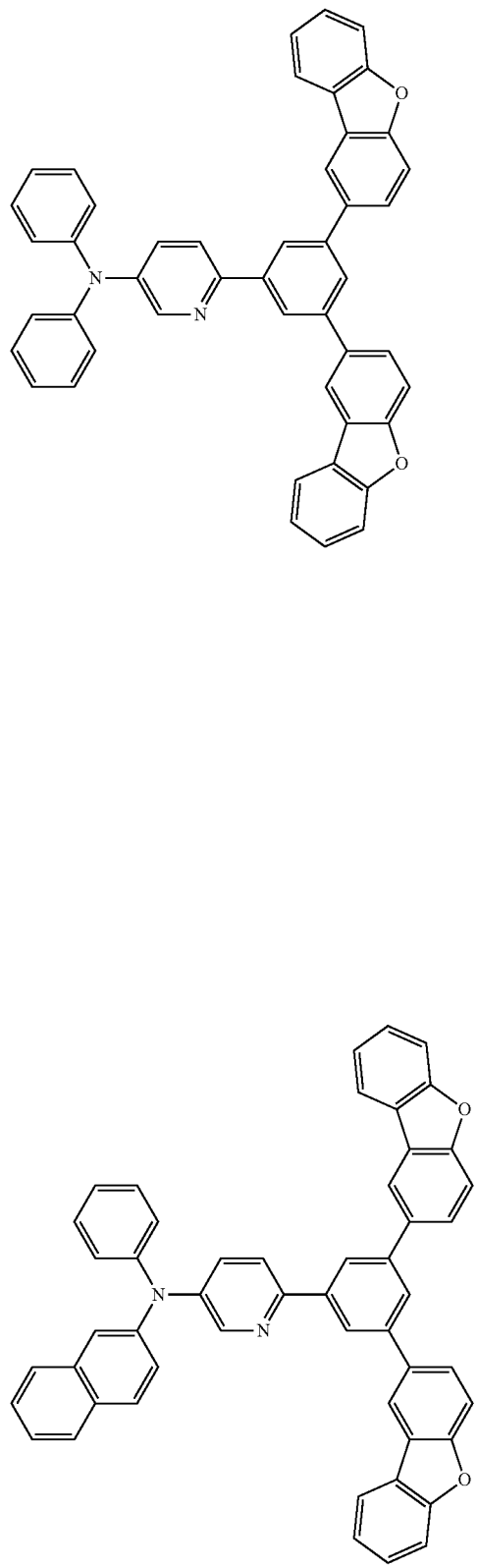
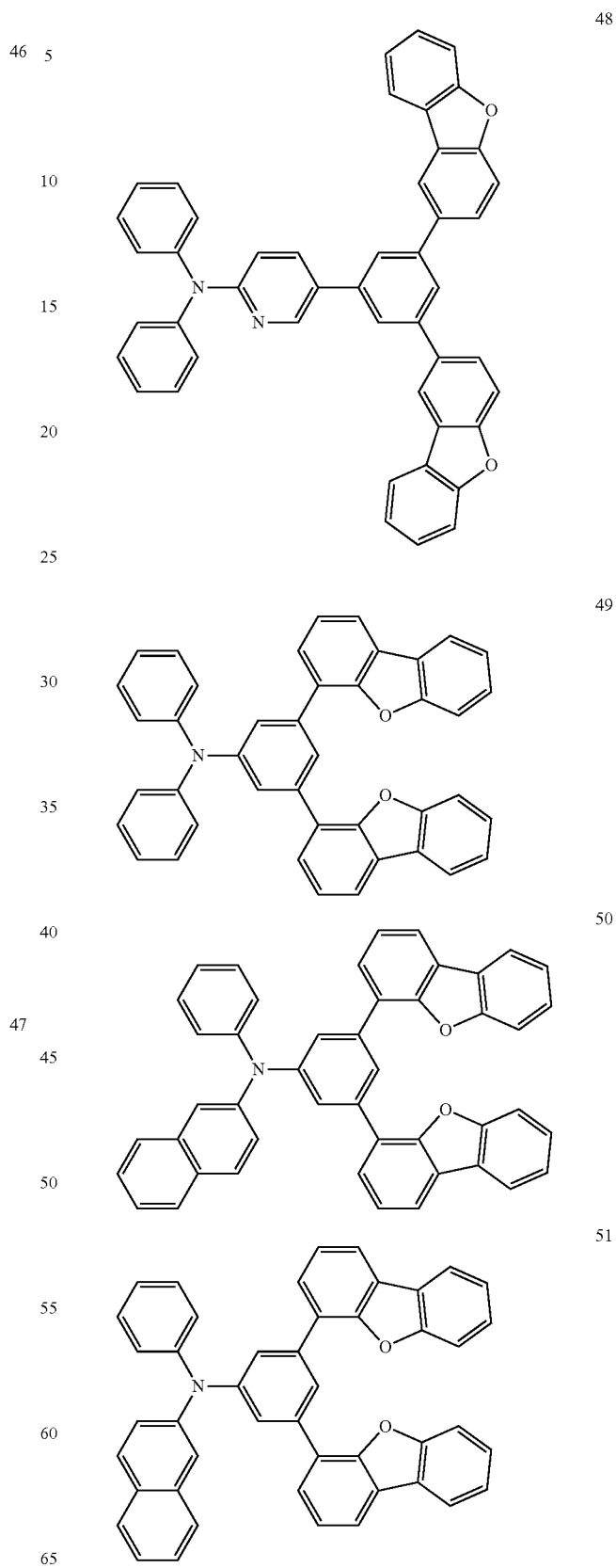

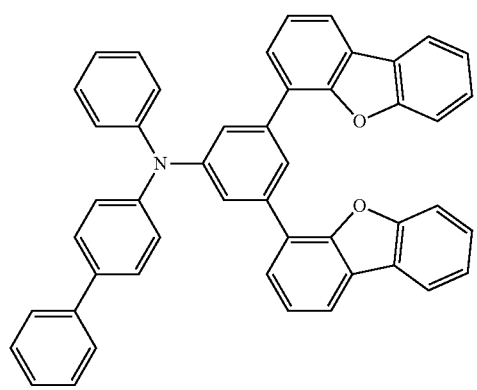
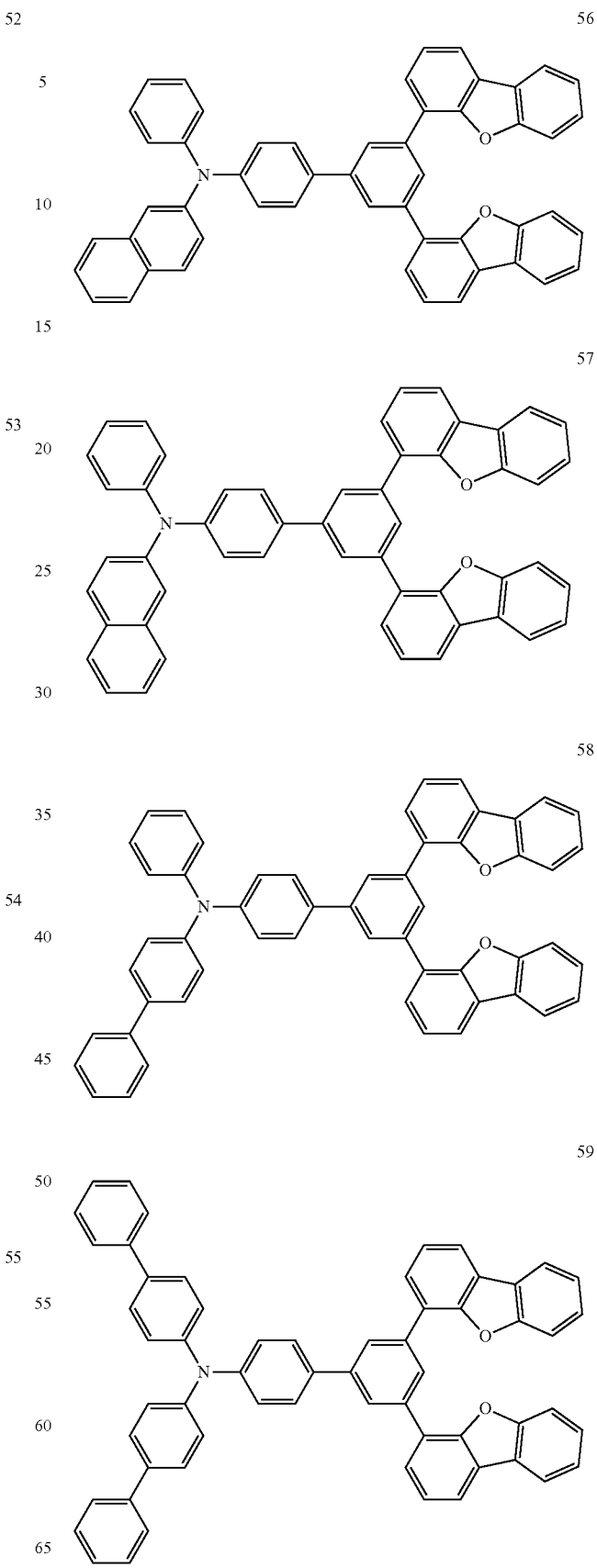

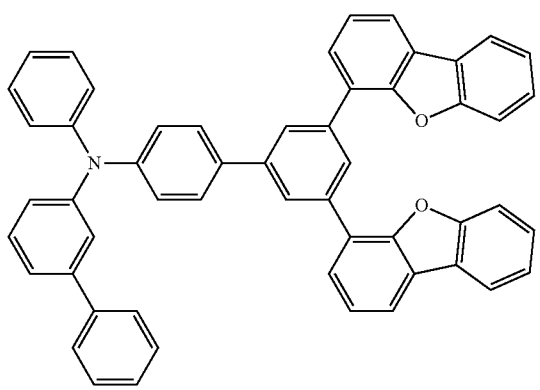
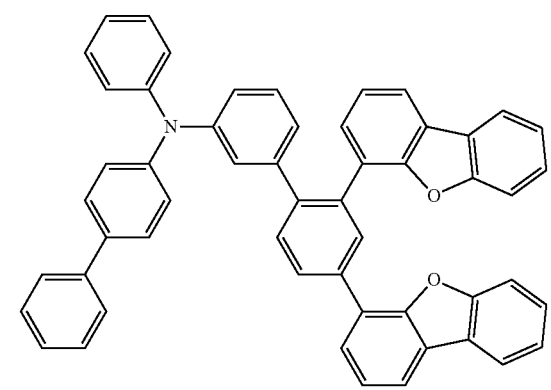
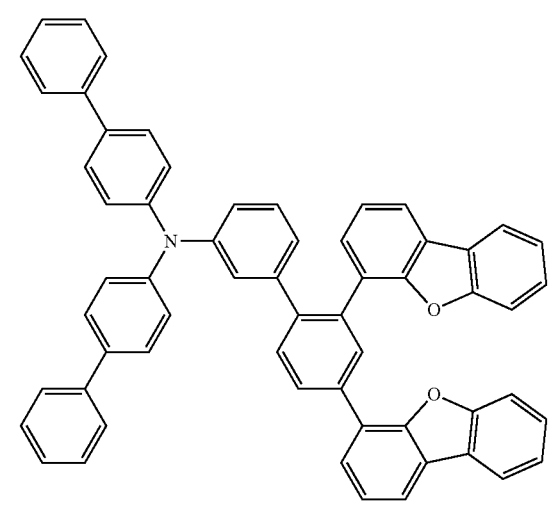
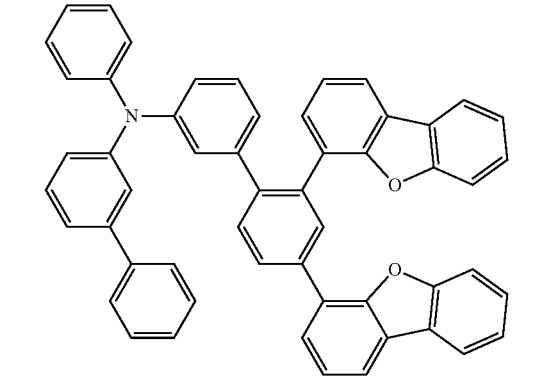
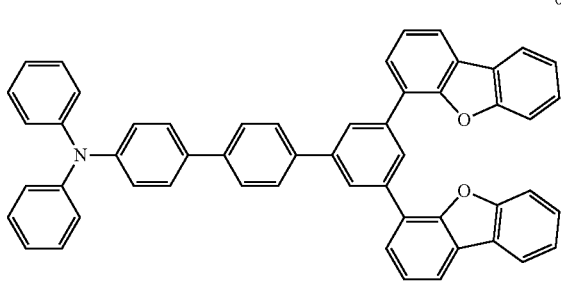

68
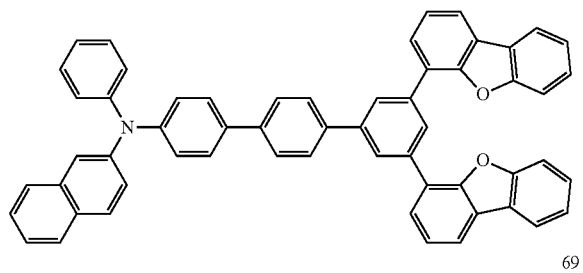
69
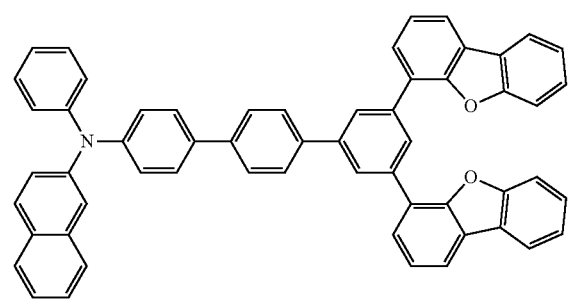
70
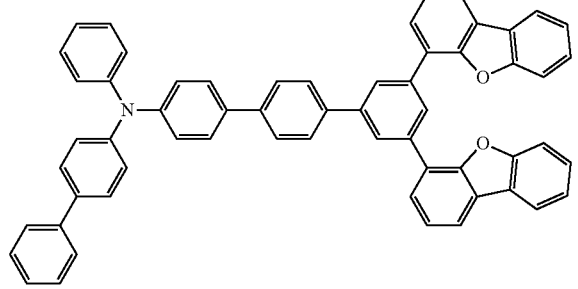
71
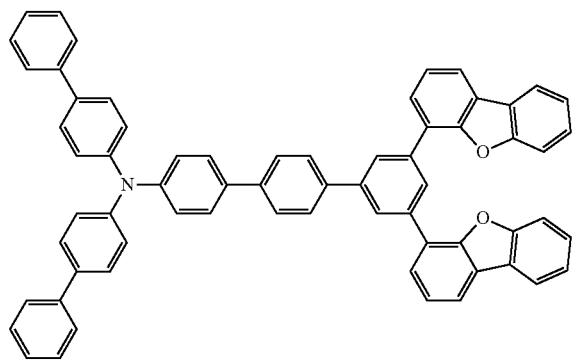
72
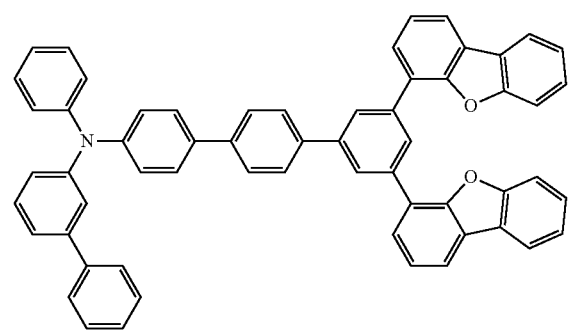
73
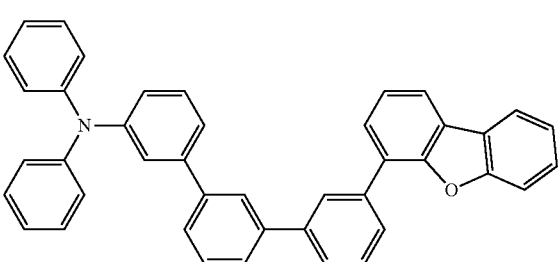
74
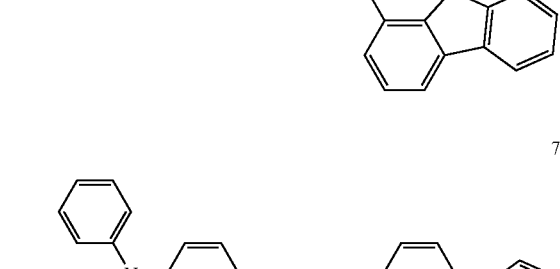
75
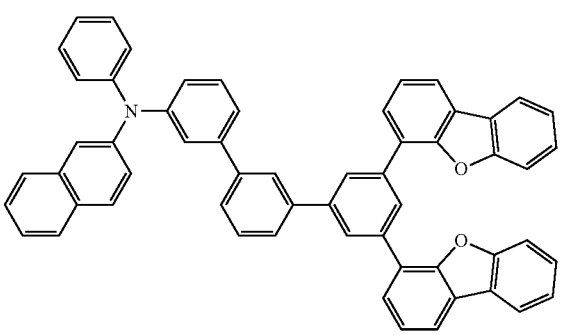
76
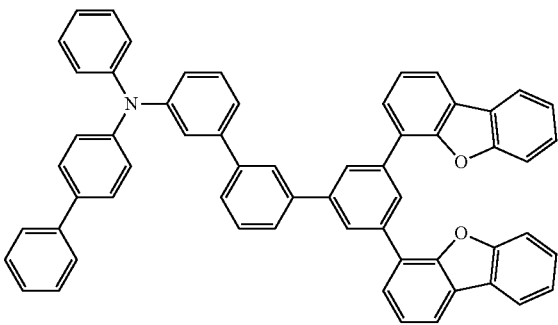

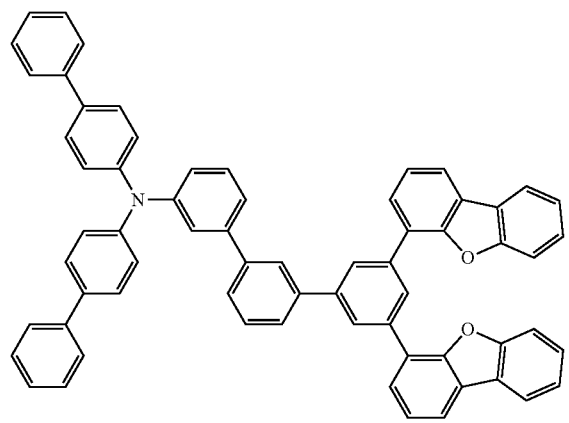
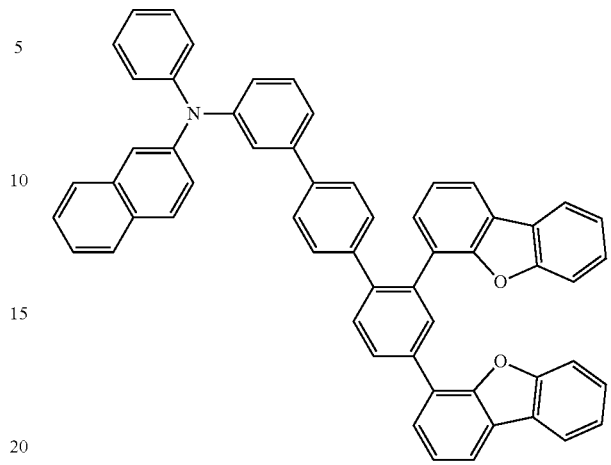
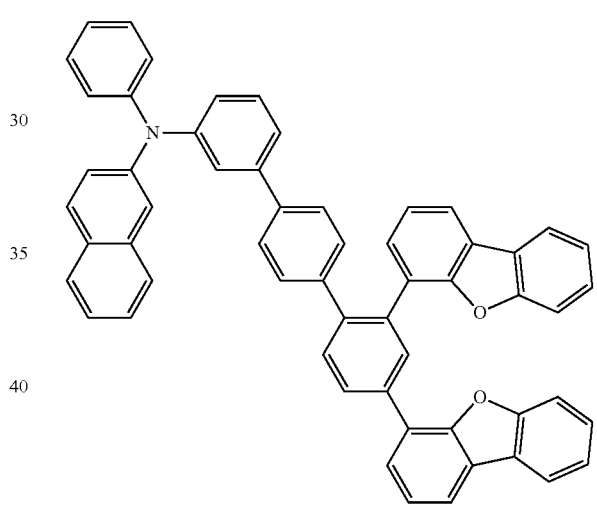
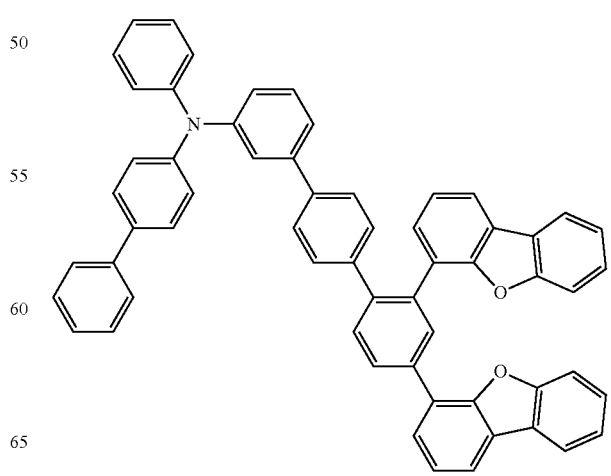

83
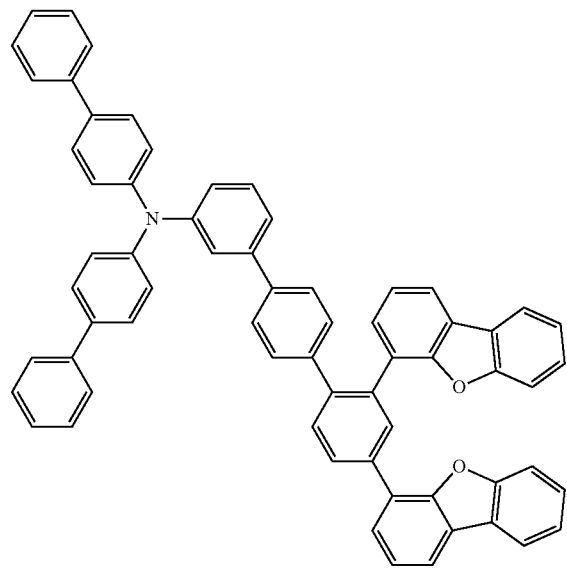
84
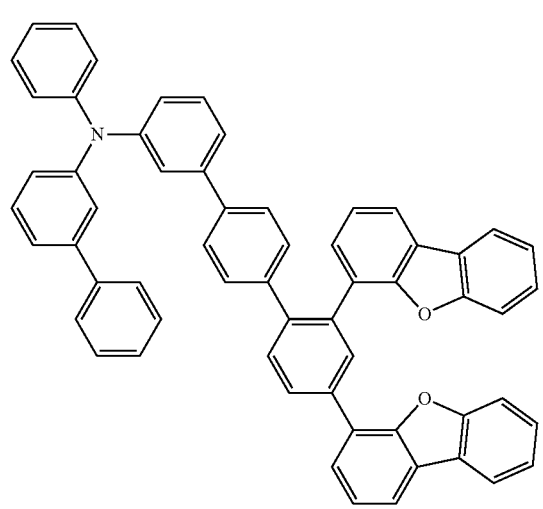
85
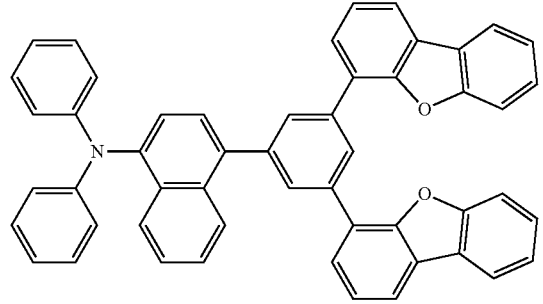
86
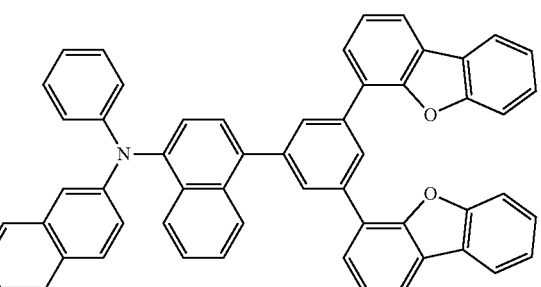
87
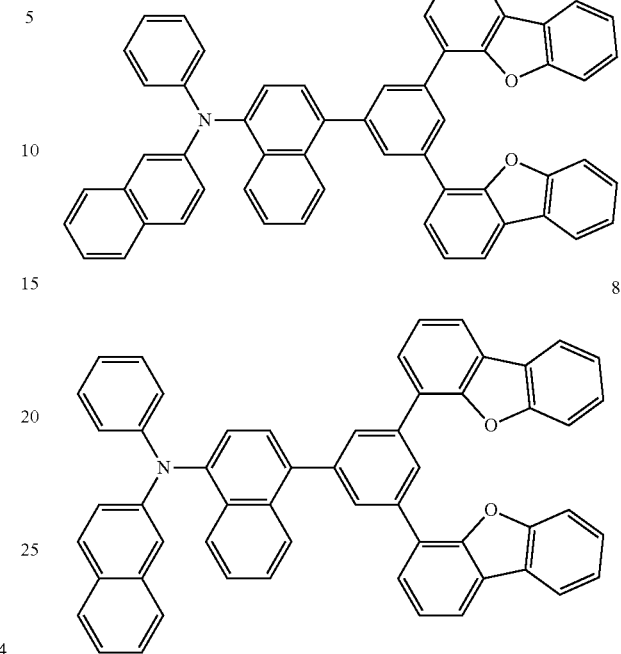
88
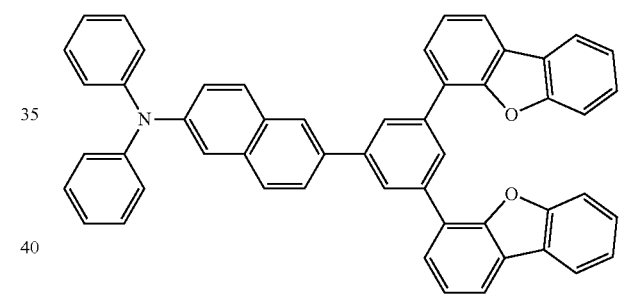
89
90
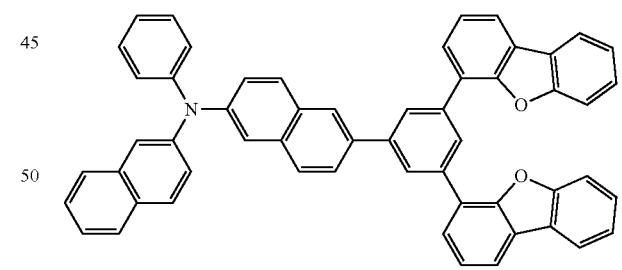

91
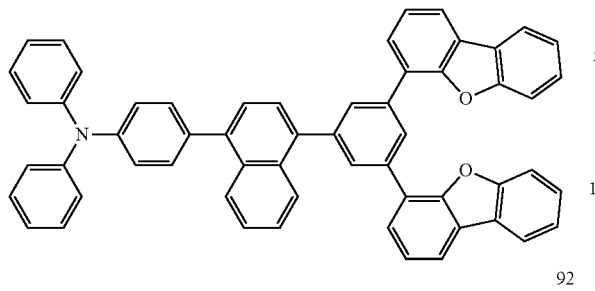
92
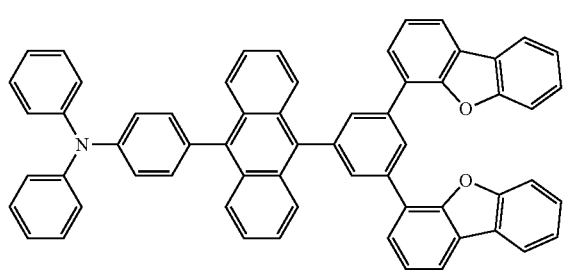
93
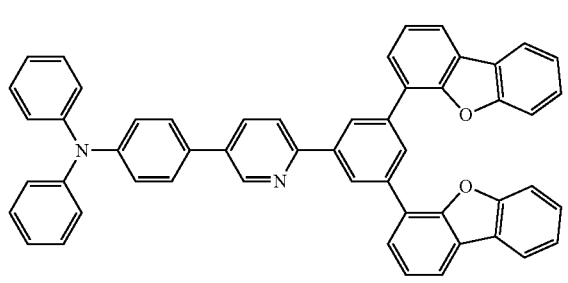
94
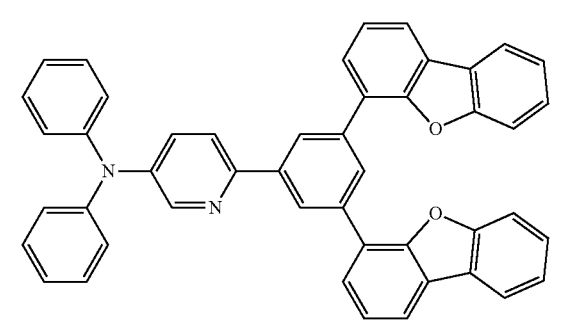
95
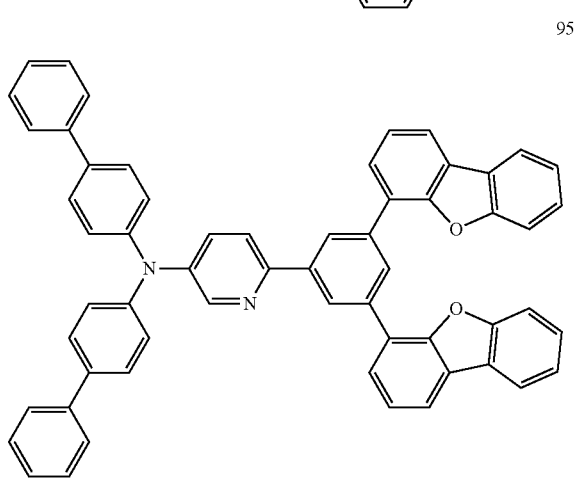
96
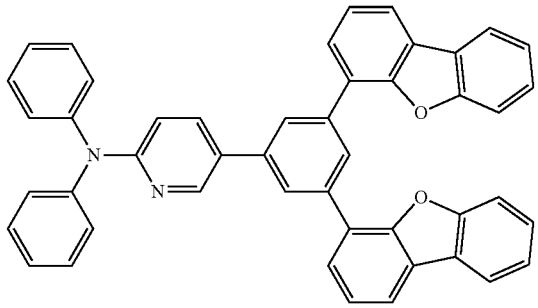
97
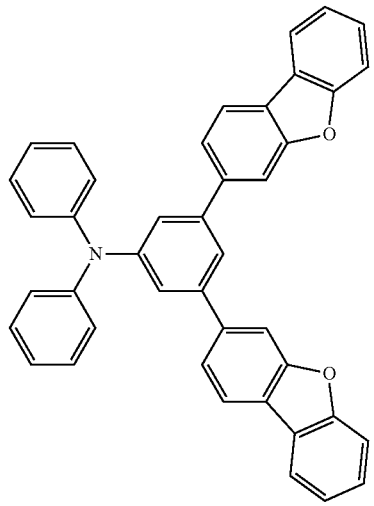
98
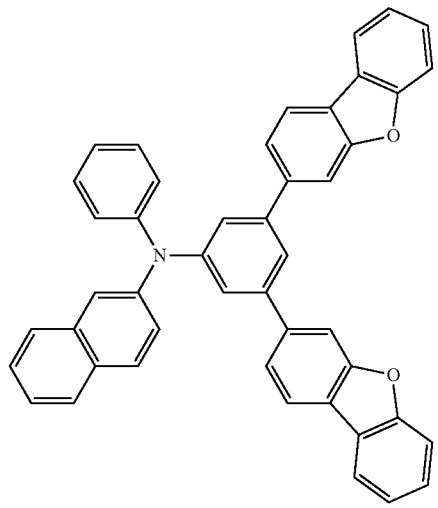

99
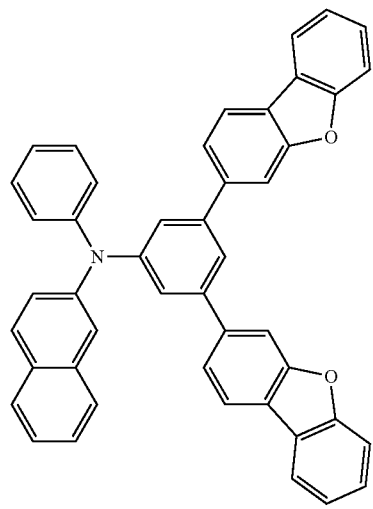
100
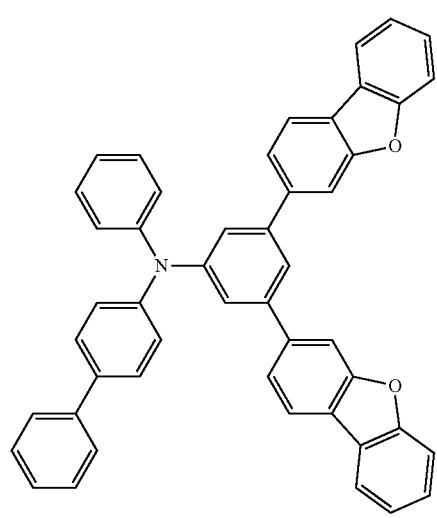
101
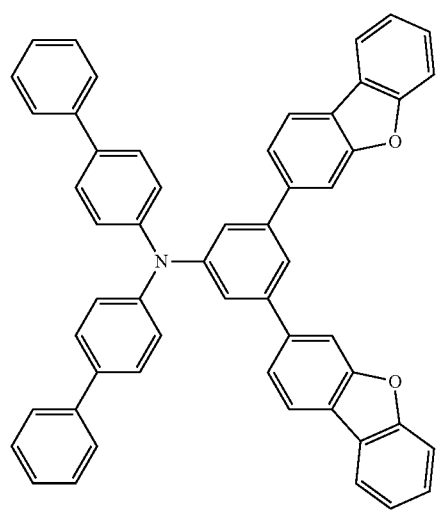
102
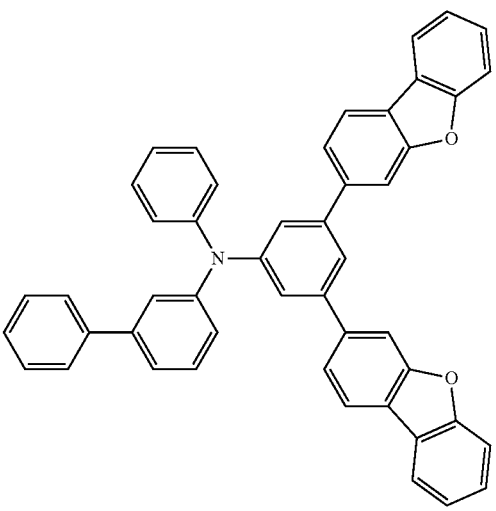
103
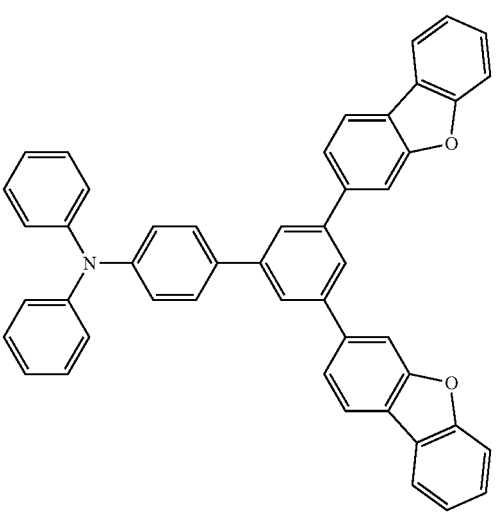
104
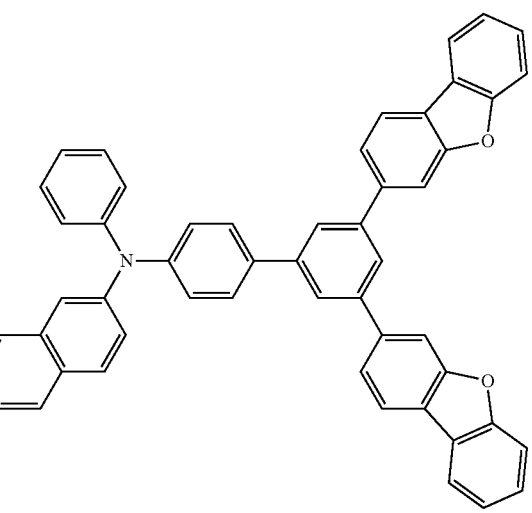

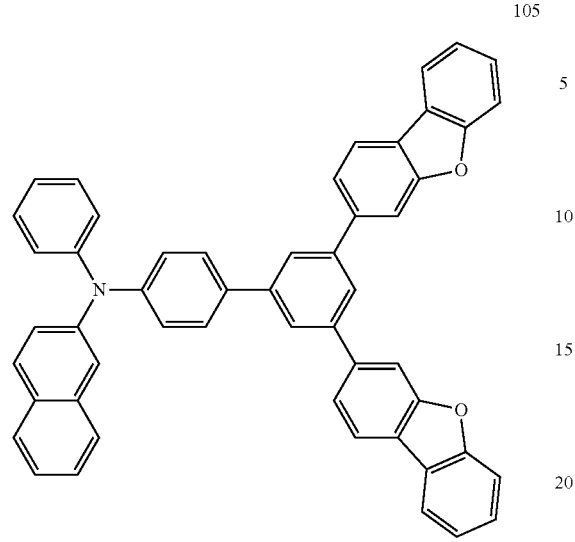
105
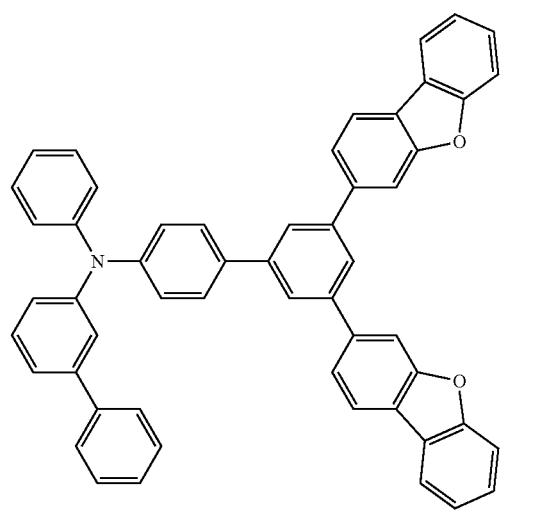
108
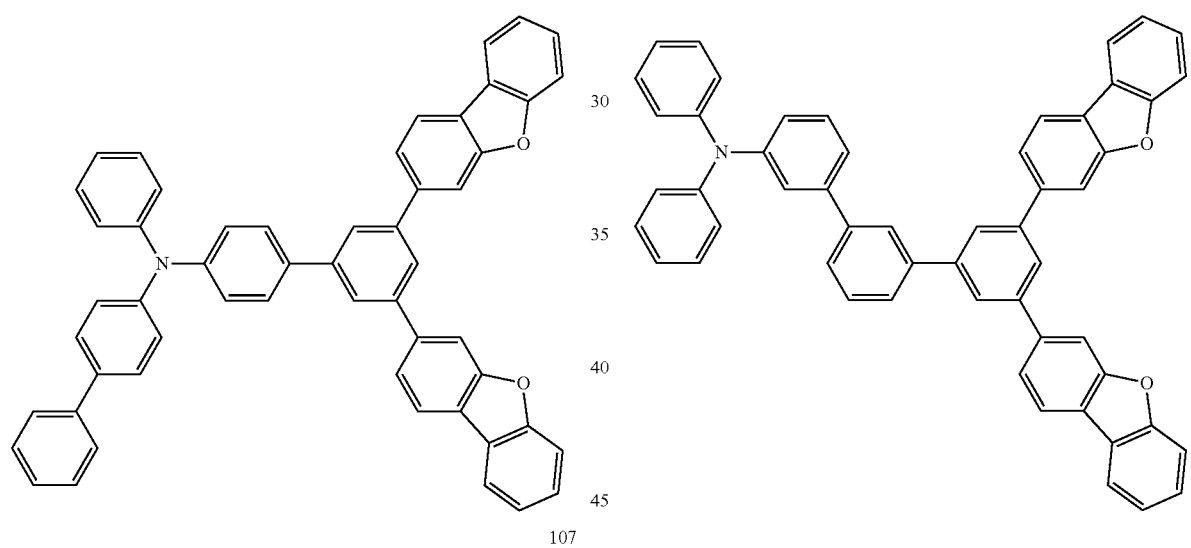
106
107
109
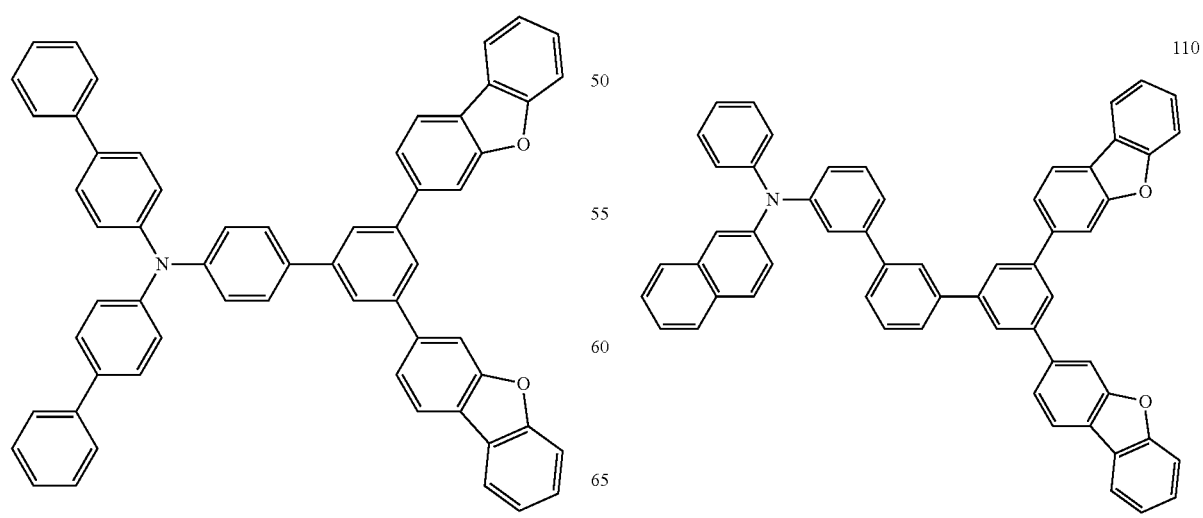
110

111
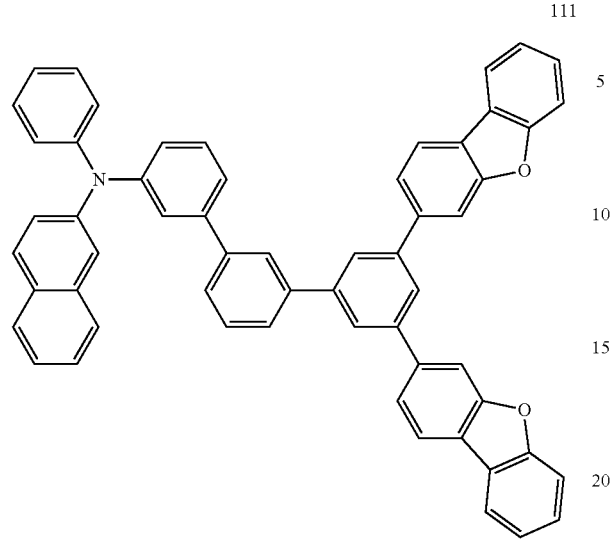
112
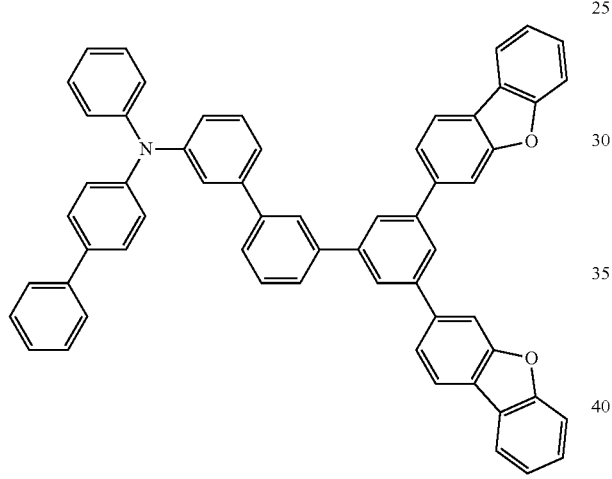
113
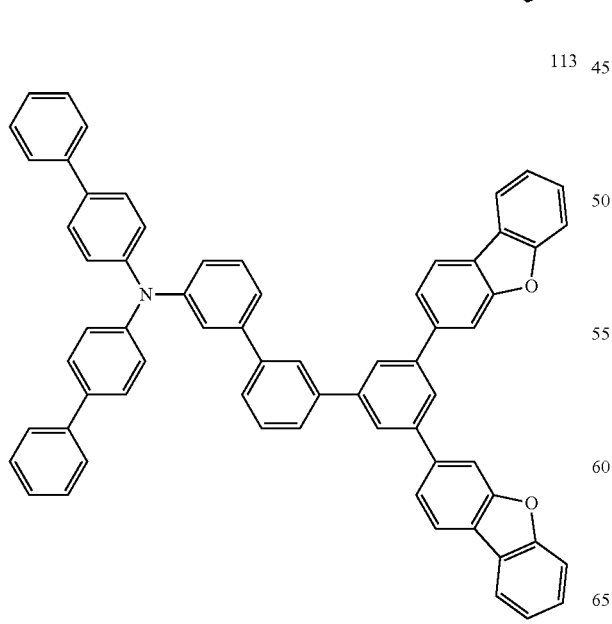
114
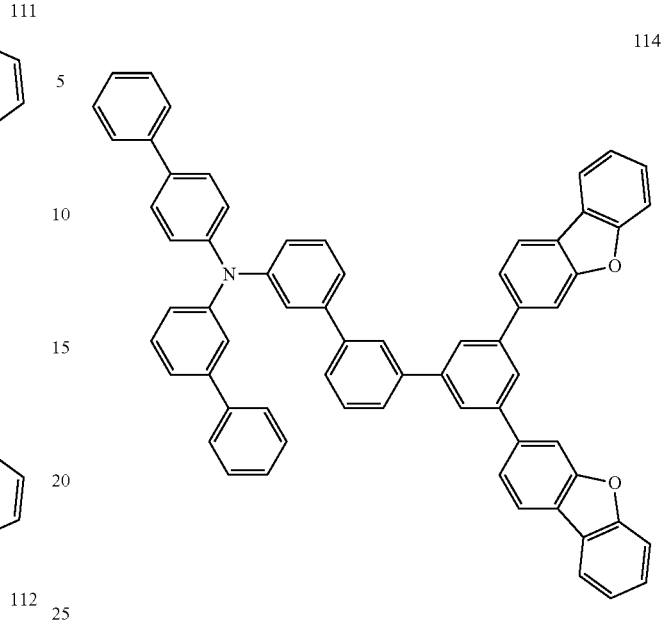
115
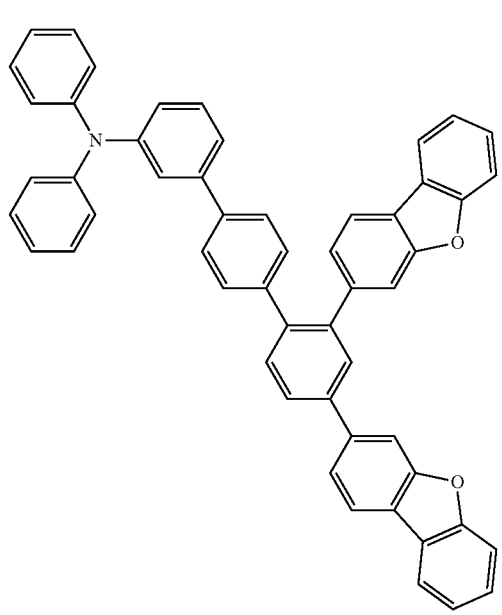

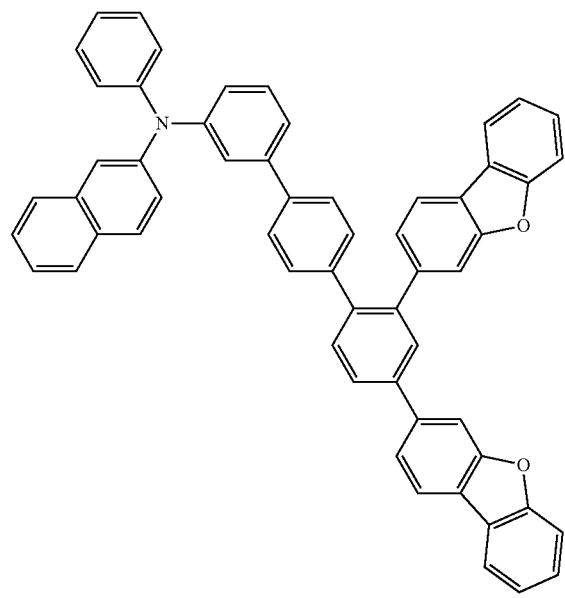
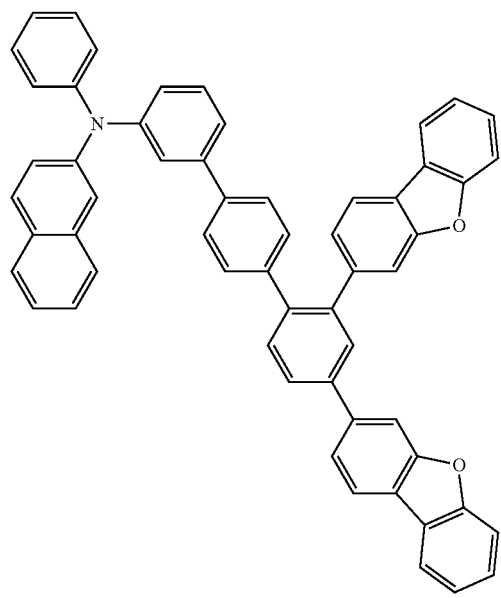

120
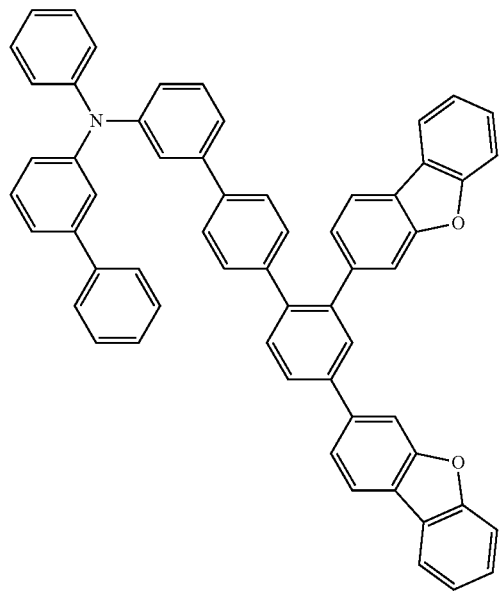
121
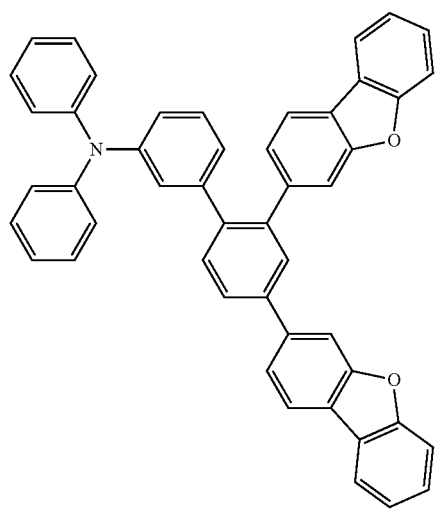
122
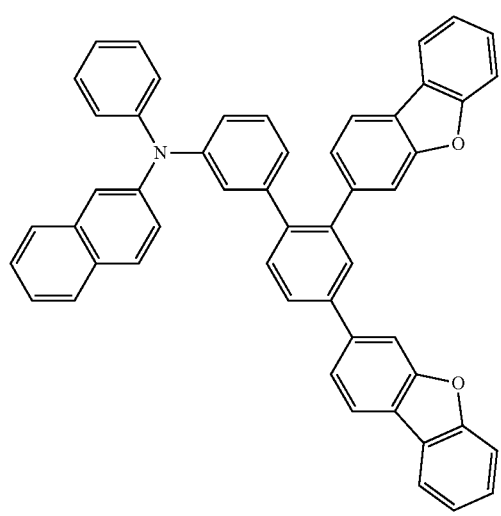
123
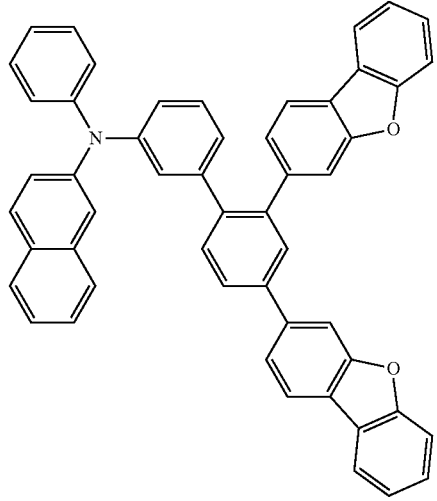
124
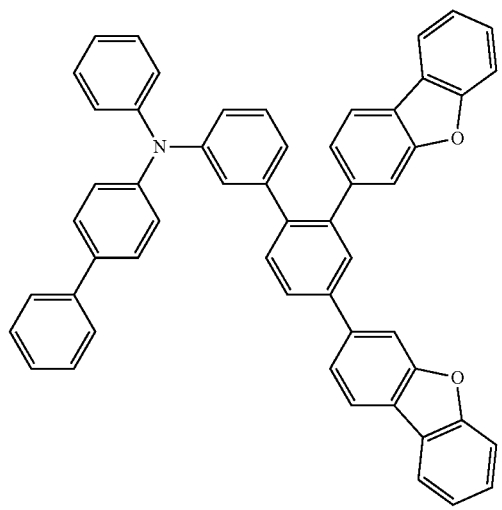
125
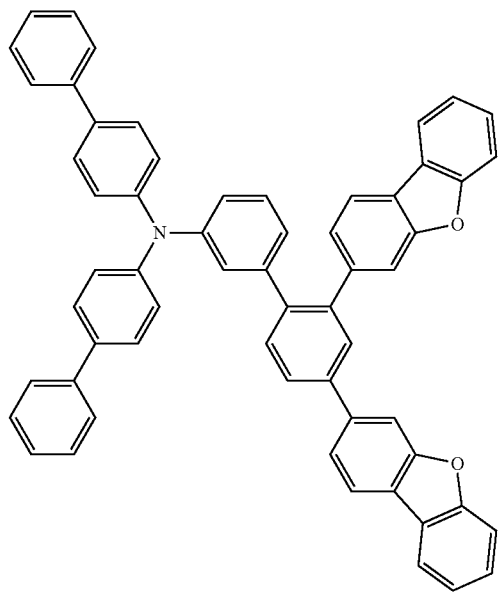

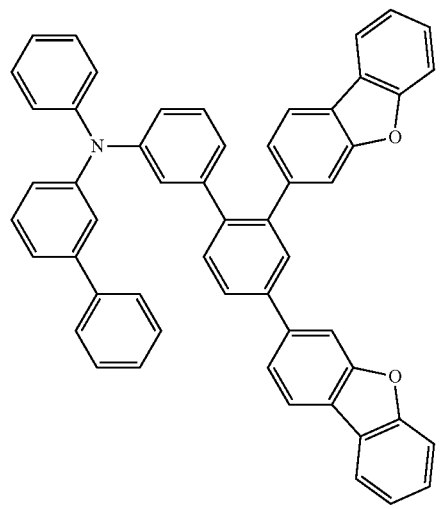
126
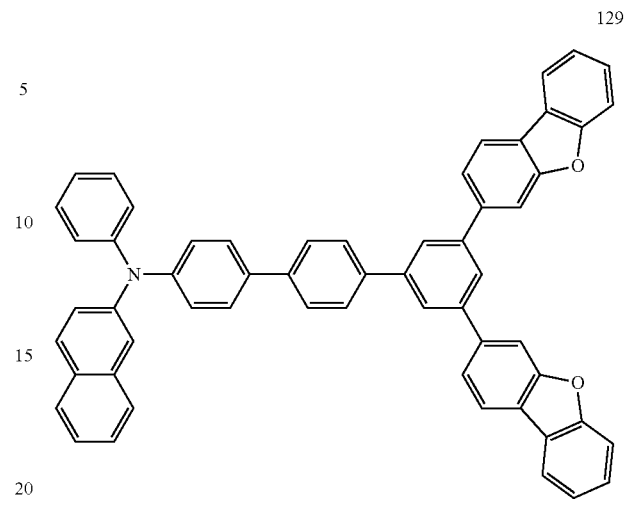
129
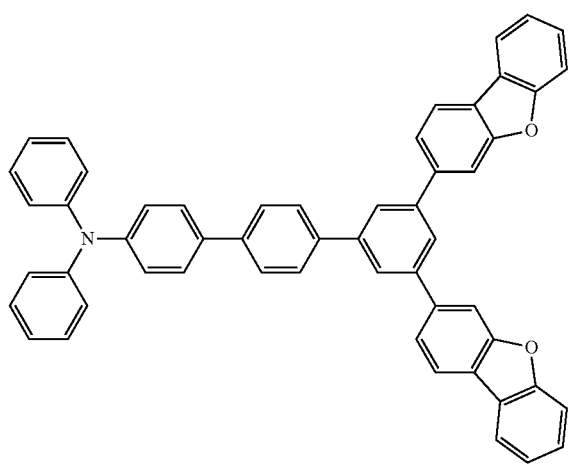
127
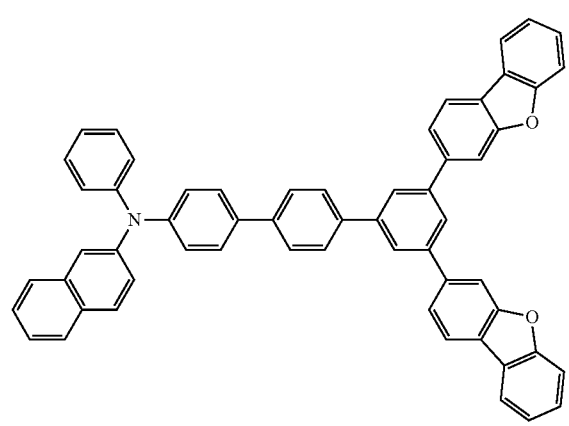
128
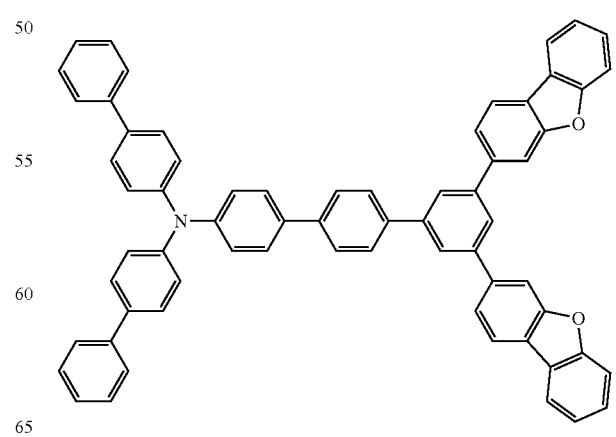
130
131

132
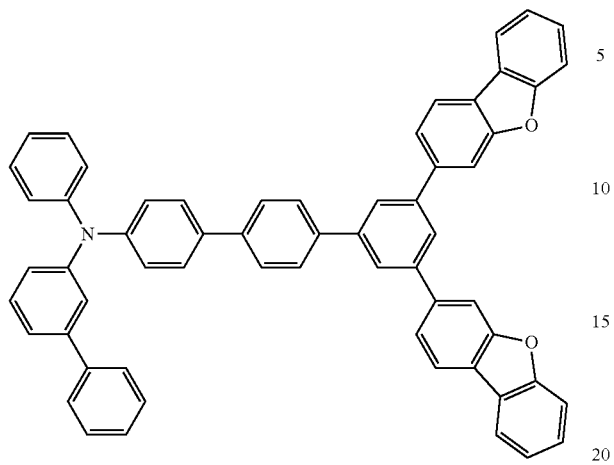
133
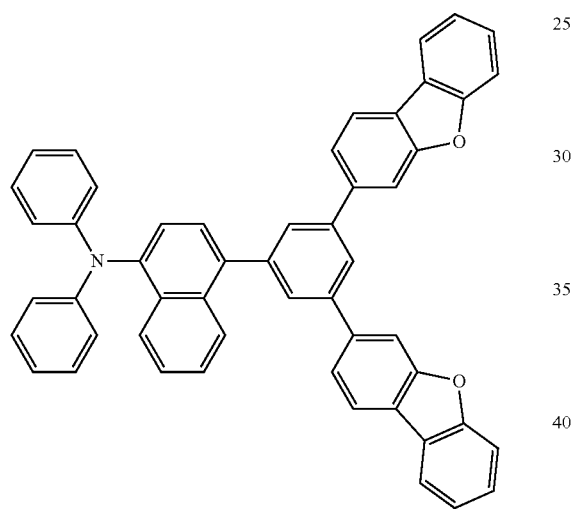
134
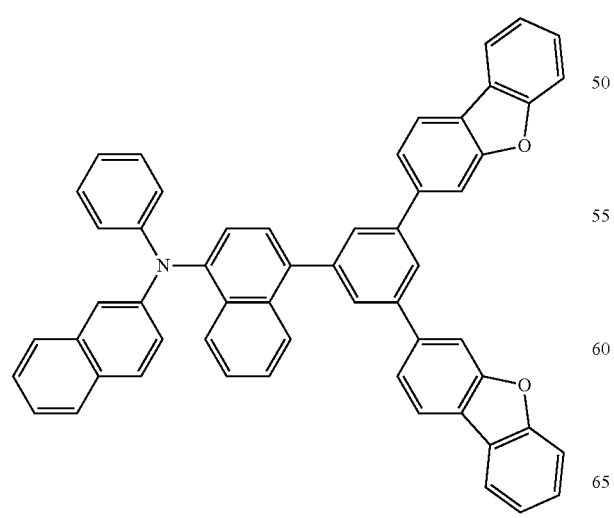
135
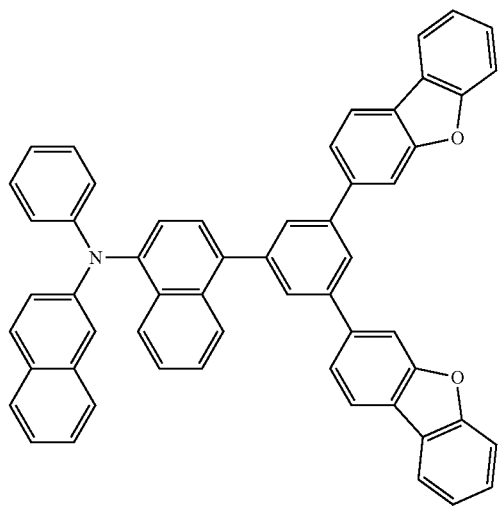
136
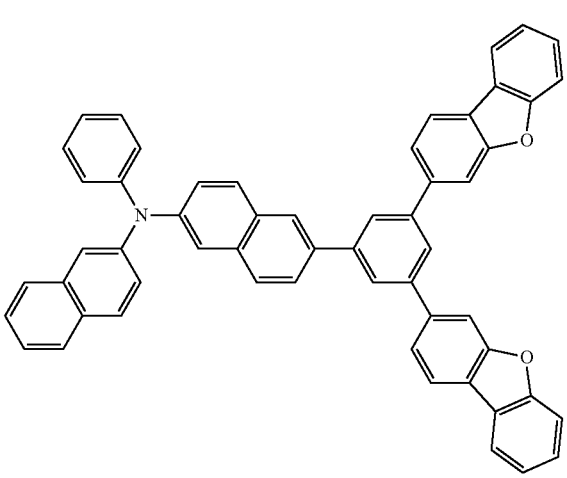
137

138
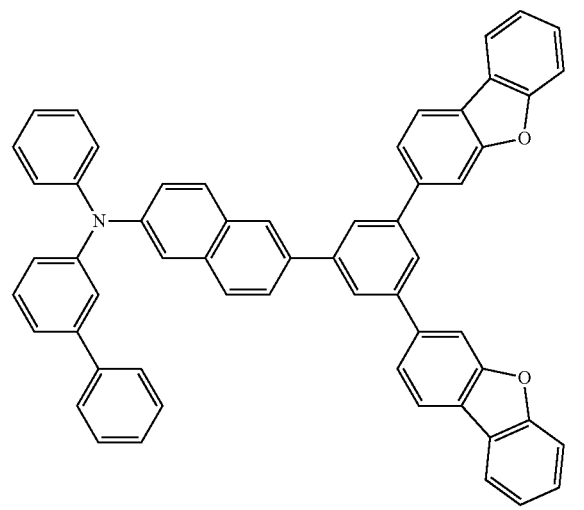
139
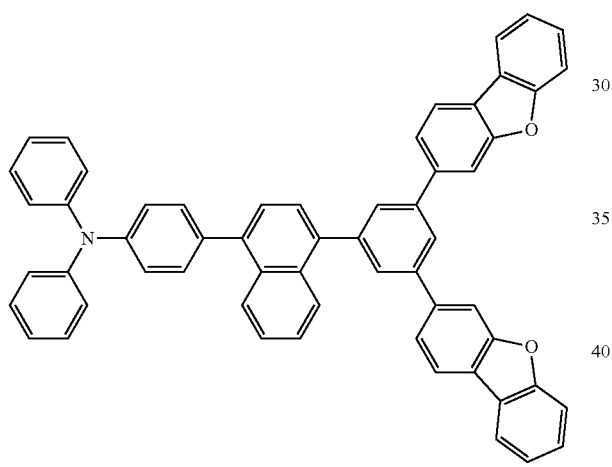
140
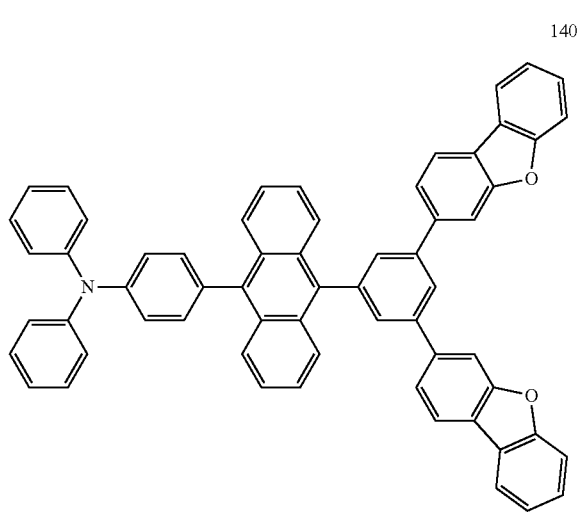
141
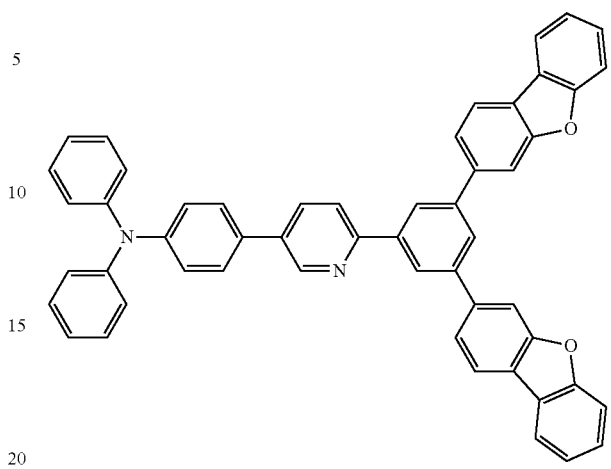
142
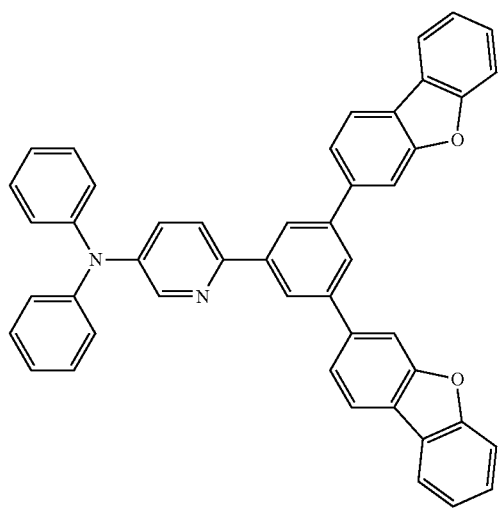
143
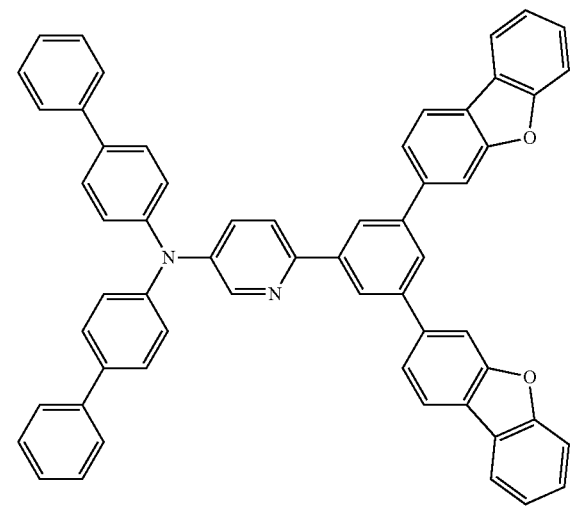

-continued

144

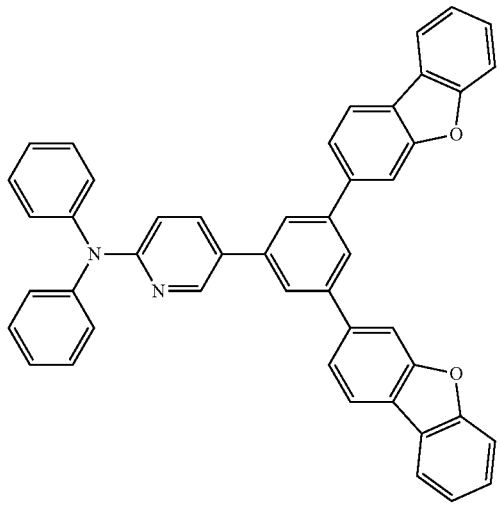

The amine-based compound represented by Formula 1 may have a structure in which A is bonded to two substituted or unsubstituted dibenzofurans (when each of $X_1$ and $X_2$ is O), two substituted or unsubstituted dibenzothiophenes (when each of $X_1$ and $X_2$ is S), or a substituted or unsubstituted dibenzofuran and a substituted or unsubstituted dibenzothiophene (when $X_1$ is S, and $X_2$ is O or when $X_1$ is O, and $X_2$ is S), thereby having one or more electron donating groups to provide an excellent hole mobility.

In addition, A in the amine-based compound represented by Formula 1 may be a substituted or unsubstituted $C_6$-$C_{20}$ aromatic ring to help prevent a reduction in the efficiency and lifespan, which may otherwise be caused by hole traps.

The amine-based compound represented by Formula 1 may be synthesized by using a suitable organic synthetic method. A synthesis method of the amine-based compound may be recognizable in the art in view of the following embodiments.

The amine-based compound represented by Formula 1 may be used or included between a pair of electrodes of an organic light-emitting device. In an implementation, the amine-based compound may be included in a hole transport region, e.g., a hole transport layer. Accordingly, an organic light-emitting device according to an embodiment may include, e.g., a first electrode; a second electrode facing the first electrode; and an organic layer between the first electrode and the second electrode, the organic layer including an emission layer. The organic layer may include at least one of the amine-based compound described above.

The expression that "(an organic layer) includes at least one amine-based compound" used herein may include a case in which "(an organic layer) includes identical amine-based compounds represented by Formula 1 and a case in which (an organic layer) includes two or more different amine-based compounds represented by Formula 1.

For example, the organic layer may include, as the amine-based compound, only Compound 1. In this case, Compound 1 may exist in an emission layer of the organic light-emitting device. In some embodiments, the organic layer may include, as the amine-based compound, Compound 1 and Compound 2. In this regard, Compound 1 and Compound 2 may exist in an identical layer (for example, Compound 1 and Compound 2 may all exist in a hole transport layer), or different layers (for example, Compound 1 may exist in an emission layer and Compound 2 may exist in a hole transport layer).

The organic layer may include, e.g., i) a hole transport region that is disposed between the first electrode (anode) and the emission layer and that includes at least one of a hole injection layer, a hole transport layer, a buffer layer, and an electron blocking layer, and ii) an electron transport region that is disposed between the emission layer and the second electrode (cathode) and that includes at least one selected from a hole blocking layer, an electron transport layer, and an electron injection layer. In an implementation, the emission layer may include the amine-based compound represented by Formula 1.

The term "organic layer" used herein refers to a single layer and/or a plurality of layers disposed between the first electrode and the second electrode of an organic light-emitting device. A material included in the "organic layer" is not limited to an organic material.

FIG. 1 illustrates a schematic view of an organic light-emitting device 10 according to an embodiment. The organic light-emitting device 10 may include a first electrode 110, an organic layer 150, and a second electrode 190.

Hereinafter, the structure of an organic light-emitting device according to an embodiment and a method of manufacturing an organic light-emitting device according to an embodiment will be explained in connection with FIG. 1.

In FIG. 1, a substrate may be additionally disposed under the first electrode 110 or above the second electrode 190. The substrate may be a glass substrate or transparent plastic substrate, each with excellent mechanical strength, thermal stability, transparency, surface smoothness, ease of handling, and water-resistance.

The first electrode 110 may be formed by depositing or sputtering a material for forming the first electrode on the substrate. When the first electrode 110 is an anode, the material for the first electrode may be selected from materials with a high work function to facilitate hole injection. The first electrode 110 may be a reflective electrode or a transmissive electrode. The material for the first electrode may be a transparent and highly conductive material, and examples of such a material may include indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one of magnesium (Mg), aluminum(Al), aluminum-lithium(Al—Li), calcium (Ca), magnesium-indium(Mg—In), magnesium-silver (Mg—Ag) may be used.

The first electrode 110 may have a single-layer structure, or a multi-layer structure including two or more layers. For example, the first electrode 110 may have a three-layered structure of ITO/Ag/ITO.

An organic layer 150 may be disposed on the first electrode 110. The organic layer 150 may include an emission layer.

The organic layer 150 may further include a hole transport region between the first electrode and the emission layer, and/or an electron transport region between the emission layer and the second electrode.

The hole transport region may include at least one selected from a hole injection layer (HIL), a hole transport layer (HTL), a buffer layer, and an electron blocking layer (EBL). The electron transport region may include at least one selected from a hole blocking layer (HBL), an electron transport layer (ETL), and an electron injection layer (EIL).

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order.

When the hole transport region includes a hole injection layer, the hole injection layer may be formed on the first electrode 110 by using various methods, e.g., vacuum deposition, spin coating casting, a Langmuir-Blodgett (LB) method, ink-jet printing, laser-printing, or laser-induced thermal imaging.

When a hole injection layer is formed by vacuum deposition, e.g., the vacuum deposition may be performed at a temperature of a deposition temperature of about 100° C. to about 500° C., at a vacuum degree of about $10^{-8}$ torr to about $10^{-3}$ torr, and/or at a deposition rate of about 0.01 Å/sec to about 100 Å/sec in consideration of a compound for a hole injection layer to be deposited, and the structure of a hole injection layer to be formed.

When a hole injection layer is formed by spin coating, the spin coating may be performed at a coating rate of about 2,000 rpm to about 5,000 rpm, and/or at a temperature of about 80° C. to about 200° C. in consideration of a compound for a hole injection layer to be deposited, and the structure of a hole injection layer to be formed.

Suitable hole injection materials may be used as a hole injection material, e.g., N,N'-diphenyl-N,N'-bis-[4-(phenyl-m-tolyl-amino)-phenyl]-biphenyl-4,4'-diamine (DNTPD), a phthalocyanine compound such as copper phthalocyanine, m-MTDATA [4,4',4''-tris(3-methylphenylphenylamino)triphenylamine], NPB(N,N'-di(1-naphthyl)-N,N'-diphenyl-benzidine(N,N'-di(1-naphthyl)-N,N'-diphenylbenzidine)), TDATA, 2-TNATA, Pani/DBSA (polyaniline/dodecylbenzenesulfonic acid:polyaniline/dodecylbenzenesulfonic acid), PEDOT/PSS(poly(3,4-ethylenedioxythiophene)/poly(4-styrenesulfonate):poly(3,4-ethylenedioxythiophene)/poly(4-styrenesulfonate)), Pani/CSA (polyaniline/camphor sulfonic acid:polyaniline/camphor sulfonic acid) or PANI/PSS (polyaniline)/poly(4-styrenesulfonate):polyaniline)/poly(4-styrene sulfonate)).

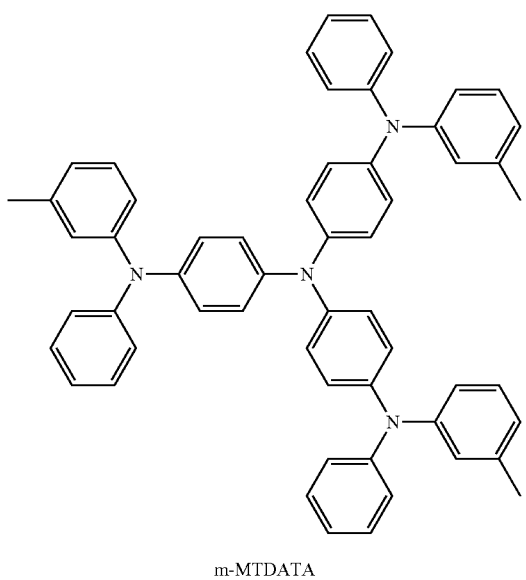

m-MTDATA

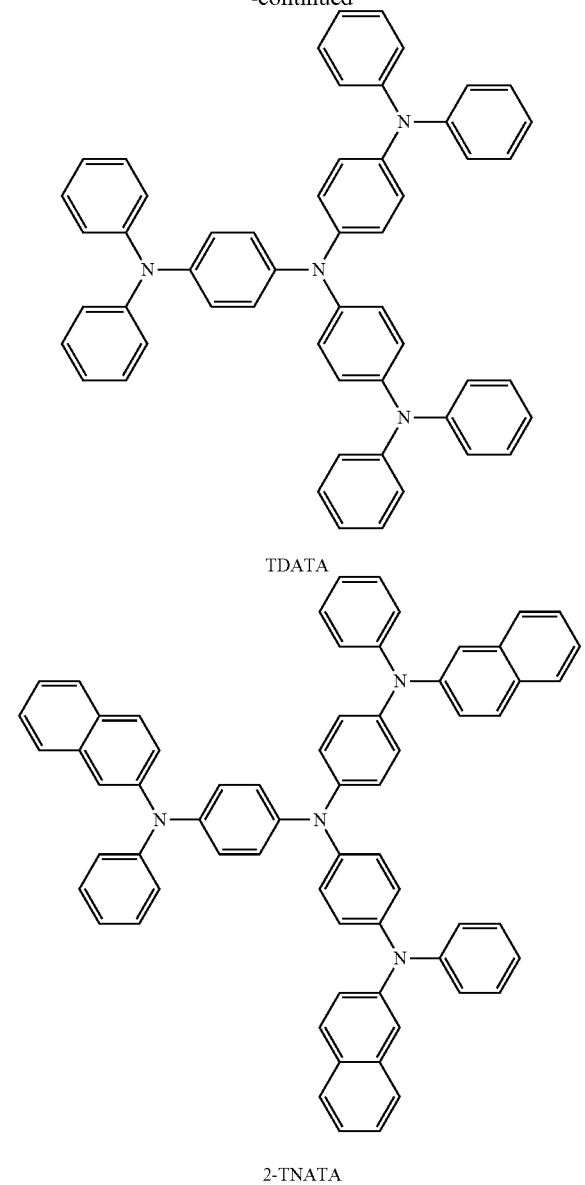

TDATA

2-TNATA

In an implementation, the hole injection layer may include the amine-based compound represented by Formula 1, and/or may include other materials.

Then, the hole transport layer may be formed on the first electrode 110 or on the hole injection layer by using various methods, e.g., vacuum deposition, spin coating, casting, a Langmuir-Blodgett (LB) method, ink-jet printing, laser-printing, or laser-induced thermal imaging (LITI). When the hole transport layer is formed by vacuum deposition or spin coating, deposition and coating conditions for the hole transport layer may be determined by referring to the deposition and coating conditions for the hole injection layer.

For use as a hole transport material, a suitable hole transport materials may be used.

In an implementation, the amine-based compound represented by Formula 1 may be used as the hole transport material.

A thickness of the hole transport region may be in a range of about 100 Å to about 10,000 Å, e.g., about 100 Å to about 1,000 Å. When the hole transport region includes a hole injection layer and a hole transport layer, the thickness of the hole injection layer may be in a range of about 100 Å to about 10,000 Å, e.g., about 100 Å to about 1,000 Å, and the thickness of the hole transport layer may be in a range of about 50 Å to about 2,000 Å, e.g., about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or unhomogeneously dispersed in the hole transport region.

The charge-generation material may be, e.g., a p-dopant. The p-dopant may include one selected from a quinone derivative, a metal oxide, and a cyano group-containing compound. Examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below.

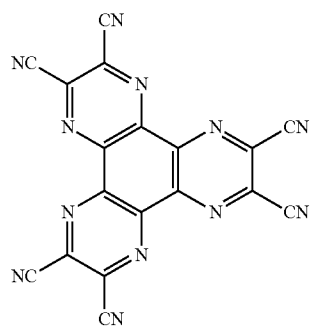

<Compound HT-D1>

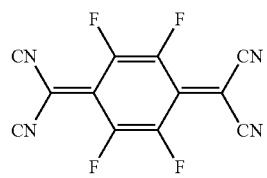

<F4-TCNQ>

The hole transport region may further include, in addition to the hole injection layer and the hole transport layer, at least one of a buffer layer and an electron blocking layer. The buffer layer may compensate for an optical resonance distance according to a wavelength of light emitted from the emission layer, and light-emission efficiency of a formed organic light-emitting device may be improved. For use as a material included in the buffer layer, materials that are included in the hole transport region may be used. The electron blocking layer prevents injection of electrons from the electron transport region.

An emission layer may be formed on the first electrode 110 or the hole transport region by using various methods, e.g., vacuum deposition, spin coating, casting, a LB method, ink-jet printing, laser-printing, or laser-induced thermal imaging. When the emission layer is formed by vacuum deposition or spin coating, deposition and coating conditions for the emission layer may be determined by referring to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. In an implementation, the emission layer may have a stacked structure of a red emission layer, a green emission layer, and a blue emission layer, or may include a red-light emission material, a green-light emission material, and a blue-light emission material, which are mixed with each other in a single layer, to emit white light.

In an implementation, the emission layer may include the amine-based compound represented by Formula 1.

The emission layer may include a host and a dopant.

The host may include at least one selected from TPBi, TBADN, ADN (also referred to as "DNA"), CBP, CDBP, and TCP:

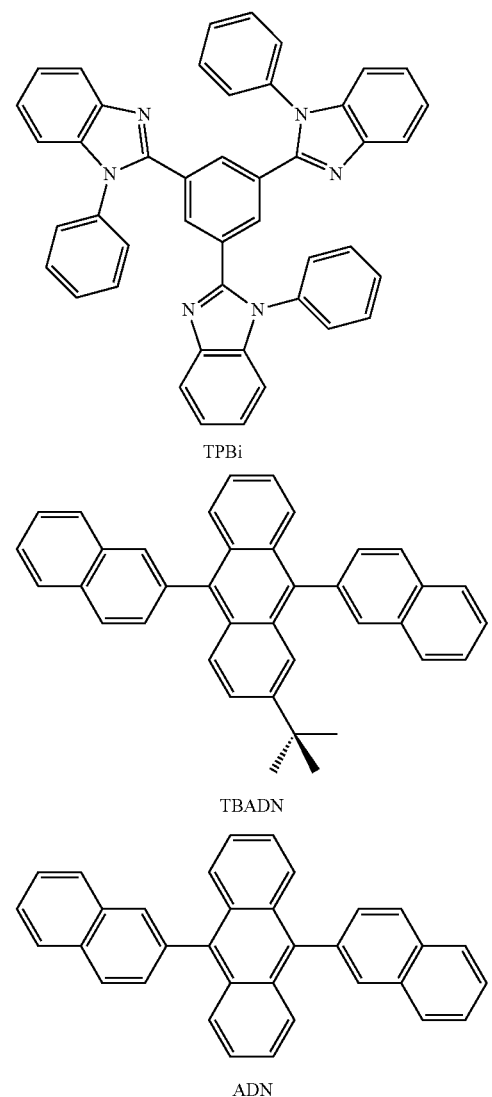

TPBi

TBADN

ADN

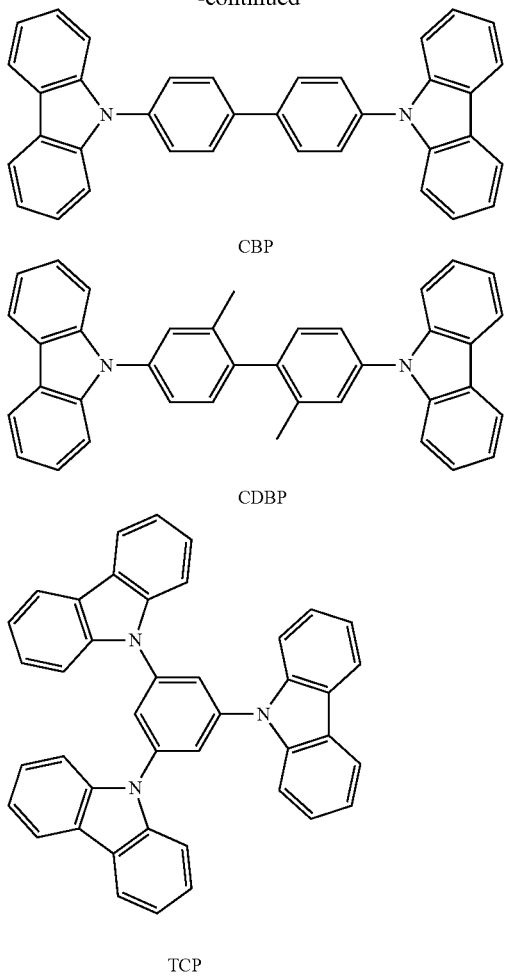

CBP

CDBP

TCP

In an implementation, the host may include a compound represented by Formula 301 below.

Ar$_{301}$-[(L$_{301}$)$_{xb1}$-R$_{301}$]$_{xb2}$   <Formula 301>

In Formula 301,

Ar$_{301}$ may be selected from:

a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si(Q$_{301}$)(Q$_{302}$)(Q$_{303}$) (wherein Q$_{301}$ to Q$_{303}$ are each independently selected from a hydrogen, a $C_1$-$C_{60}$ alkyl group, a $C_2$-$C_{60}$ alkenyl group, a $C_1$-$C_{60}$ aryl group, and a $C_1$-$C_{60}$ heteroaryl group);

L$_{301}$ may be the same as explained in connection with L$_1$;

R$_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3;

xb2 may be selected from 1, 2, 3, and 4.

For example, in Formula 301,

L$_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

In an implementation, the host may include at least one selected from Compounds H43 to H49 below.

H43

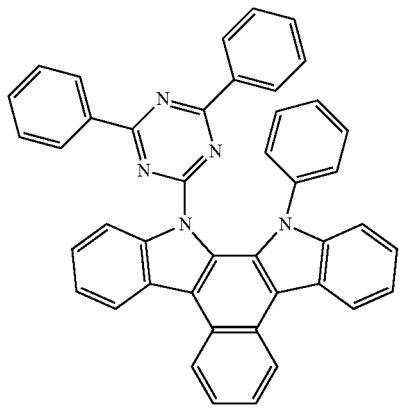

H44

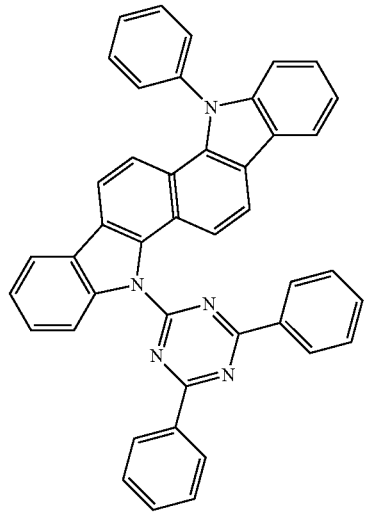

H45

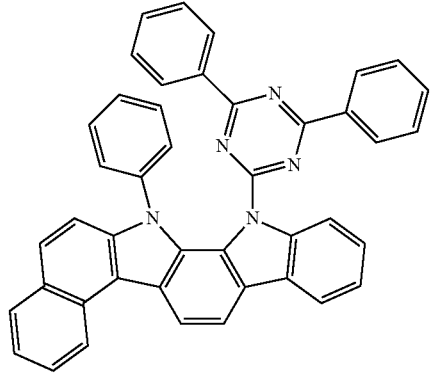

H46

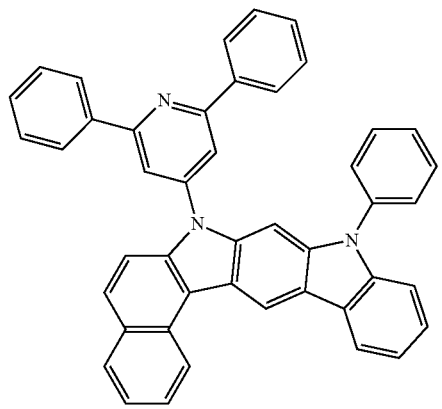

-continued

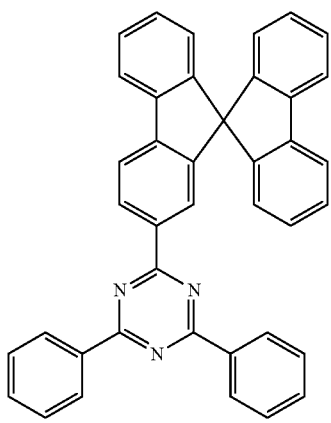
H47

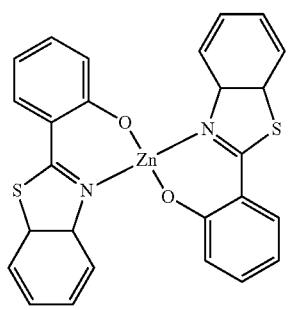
H48

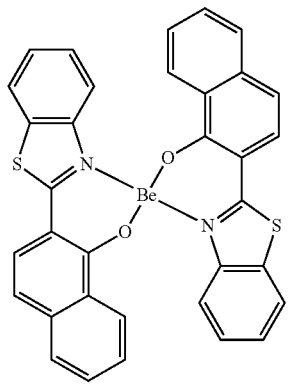
H49

The dopant may include at least one selected from a fluorescent dopant and a phosphorescent dopant.

In an implementation, the phosphorescent dopant may include an organometallic complex represented by Formula 401 below.

<Formula 401>

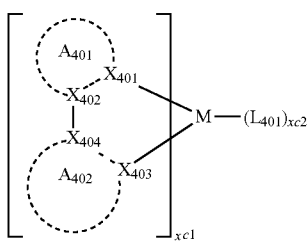

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may each independently be nitrogen or carbon;

rings $A_{401}$ and $A_{402}$ may each independently be selected from a substituted or unsubstituted benzene, a substituted or unsubstituted naphthalene, a substituted or unsubstituted fluorenene, a substituted or unsubstituted spiro-fluorenene, a substituted or unsubstituted indene, a substituted or unsubstituted pyrrol, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazol, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; and at least one substituent of the substituted benzene, substituted naphthalene, substituted fluorenene, substituted spiro-fluorenene, substituted indene, substituted pyrrol, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazol, substituted benzoimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_1$-$C_{60}$ alkenyl group, a $C_1$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;
xc1 may be 1, 2, or 3; and
xc2 may be 0, 1, 2, or 3.

In an implementation, $L_{401}$ may be a monovalent, divalent, or trivalent organic ligand. For example, $L_{401}$ may be selected from a halogen ligand (e.g., Cl or F), a diketone ligand (e.g., acetylacetonate, 1,3-diphenyl-1,3-propandionate, 2,2,6,6-tetramethyl-3,5-heptandionate, or hexafluoroacetonate), a carboxylic acid ligand (e.g., picolinate, dimethyl-3-pyrazolecarboxylate, or benzoate), a carbon monooxide ligand, an isonitrile ligand, a cyano ligand, and a phosphorous ligand (e.g., phosphine, and phosphaite).

When $A_{401}$ in Formula 401 has two or more substituents, a plurality of substituents of $A_{401}$ may bind to each other to form a saturated or unsaturated ring.

When $A_{402}$ in Formula 401 has two or more substituents, a plurality of substituents of $A_{402}$ may bind to each other to form a saturated or unsaturated ring.

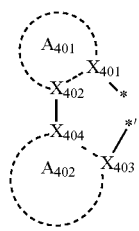

When xc1 in Formula 401 is 2 or more, a plurality of ligands in Formula 401 may be identical or different. When xc1 in Formula 401 is 2 or more, $A_{401}$ and $A_{402}$ may each be linked to $A_{401}$ and $A_{402}$ of a neighboring other ligand, directly or via a linking group (e.g., a $C_1$-$C_5$ alkylene group, —N(R')— (wherein R' is a $C_1$-$C_{10}$ alkyl group or a $C_6$-$C_{20}$ aryl group), or —C(=O)—).

In an implementation, the phosphorescent dopant may include at least one selected from Compounds PD1 to PD74 below.

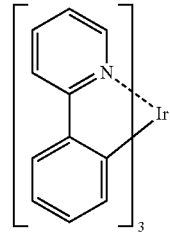

PD1

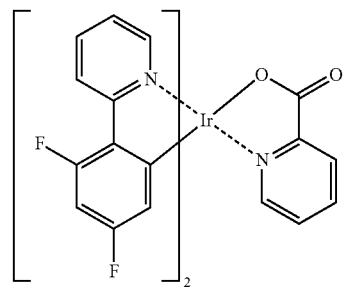

PD2

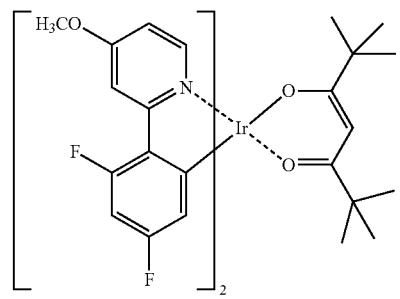

PD3

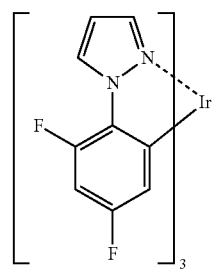

PD4

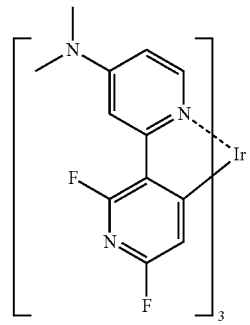

PD5

-continued
PD6 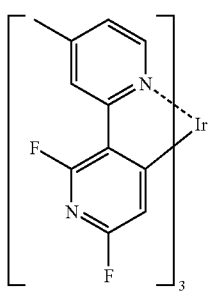
PD7 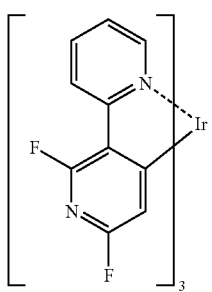
PD8 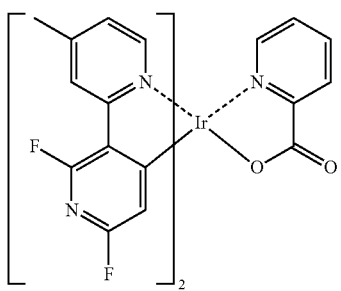
PD9 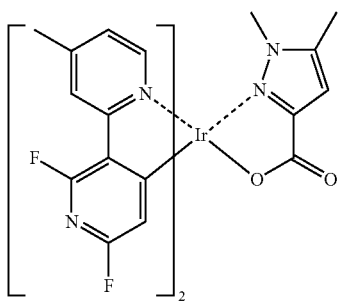
PD10 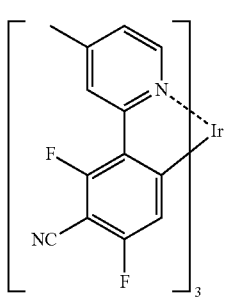
-continued
PD11 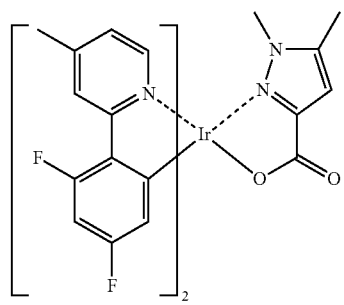
PD12 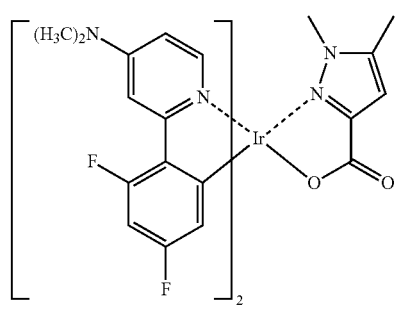
PD13 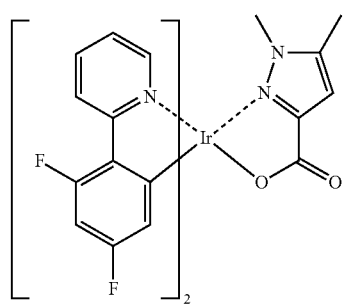
PD14 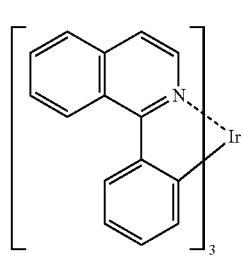
PD15 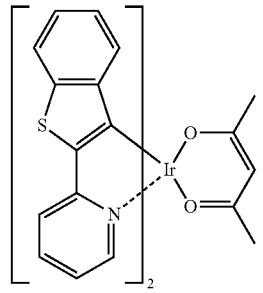

PD16 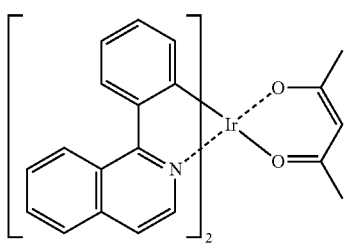
PD17 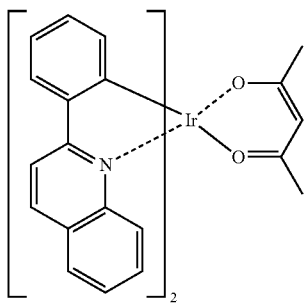
PD18 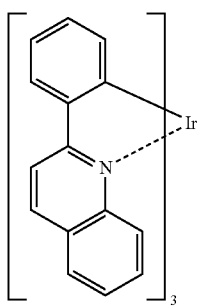
PD19 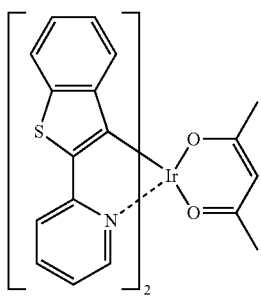
PD20 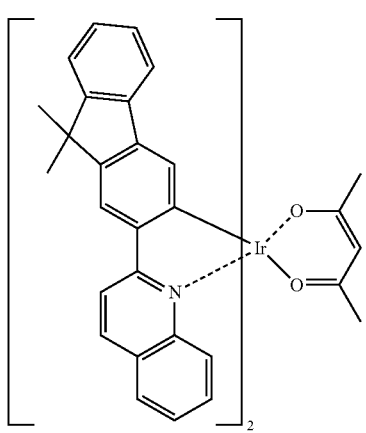
PD21 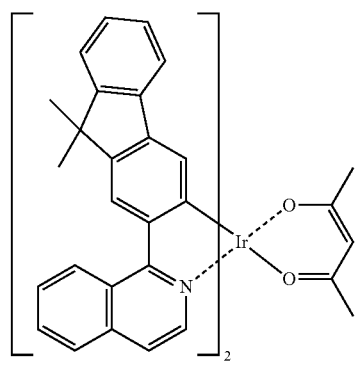
PD22 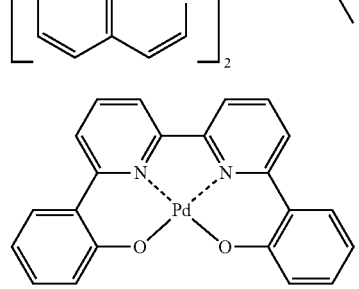
PD23 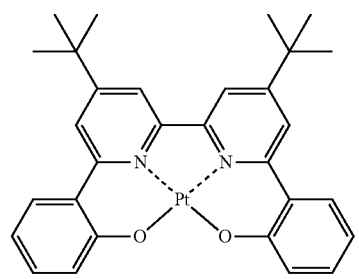
PD24 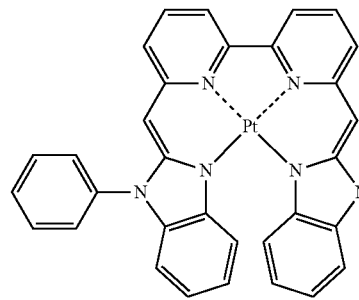
PD25 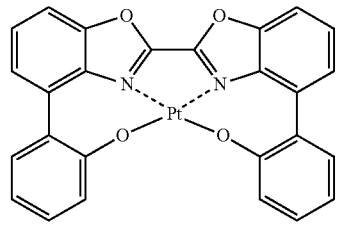
PD26

PD27 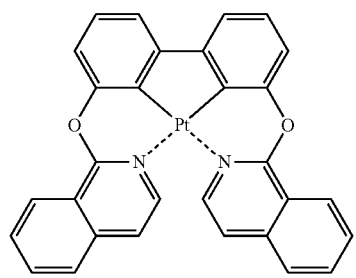
PD28 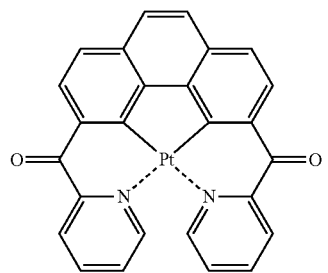
PD29 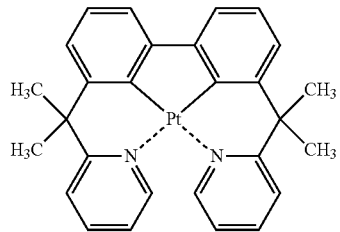
PD30 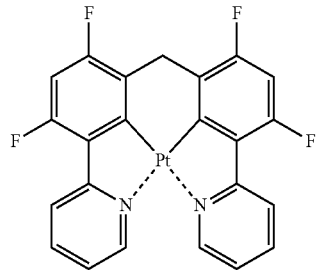
PD31 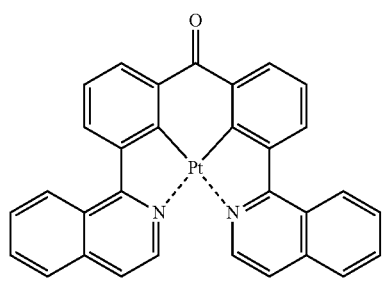
PD32 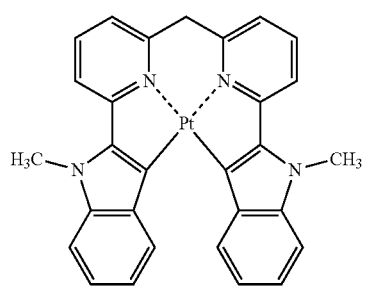
PD33 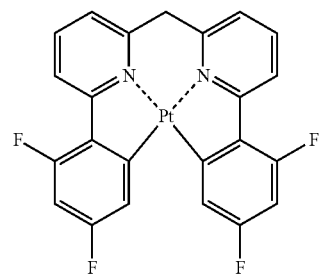
PD34 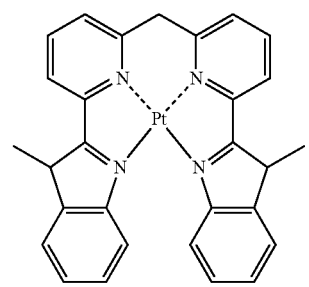
PD35 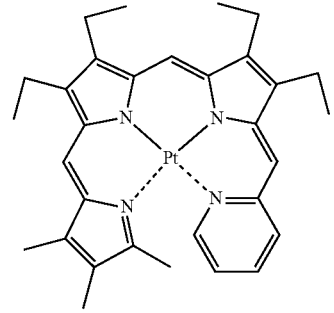
PD36 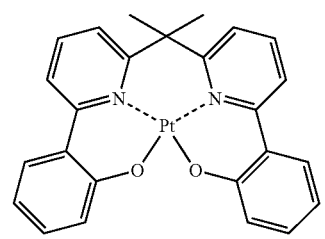
PD37 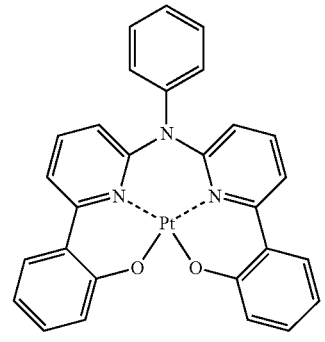

-continued
PD38
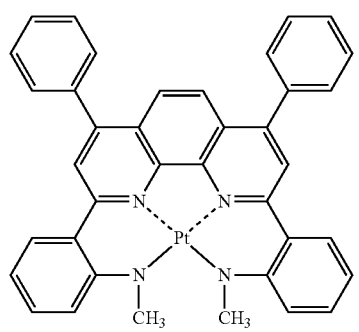
PD39
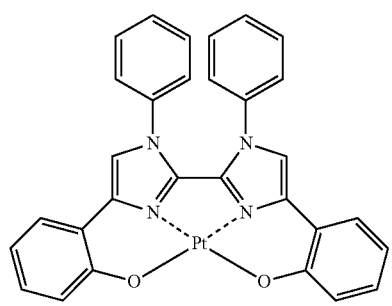
PD40
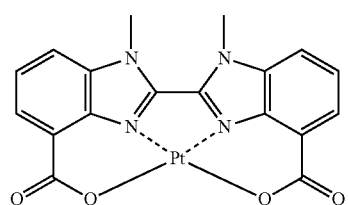
PD41
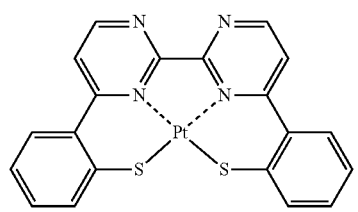
PD42
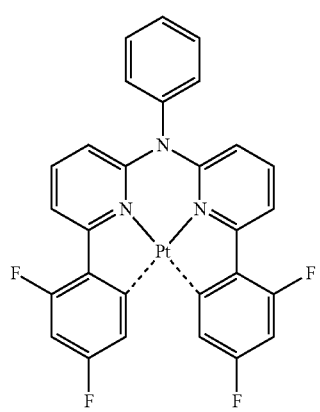
-continued
PD43
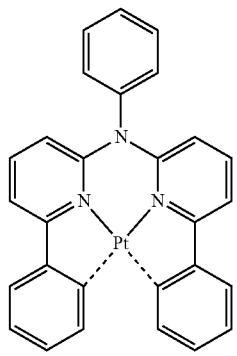
PD44
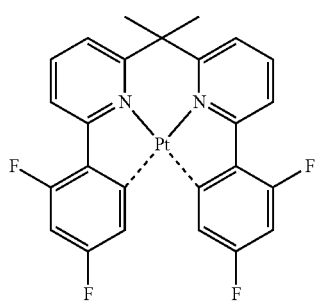
PD45
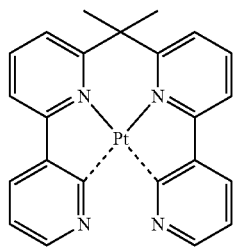
PD46
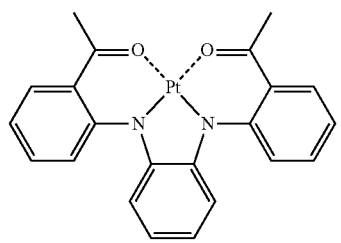
PD47
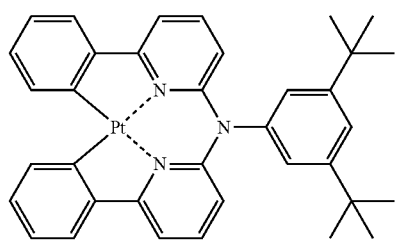
PD48
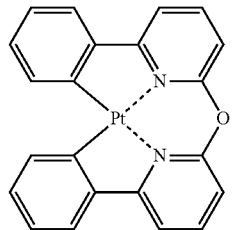

PD49 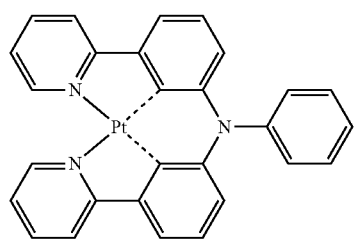
PD50 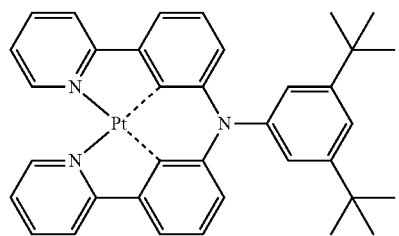
PD51 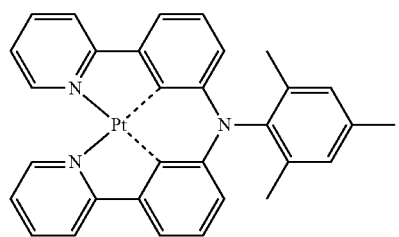
PD52 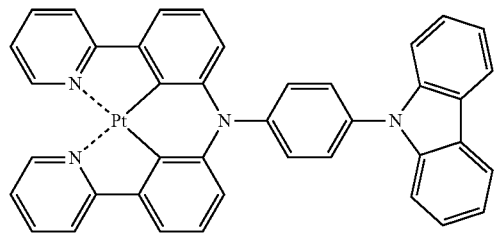
PD53 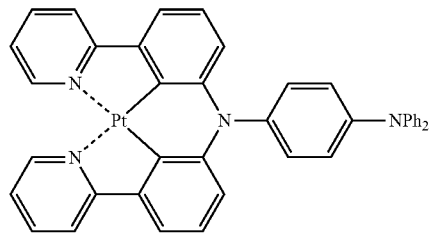
PD54 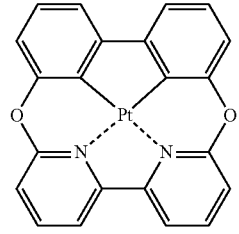
PD55 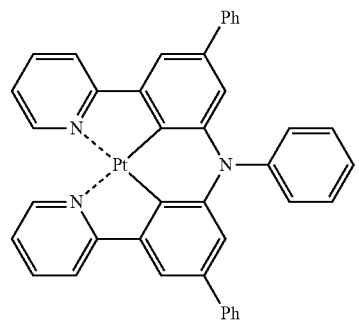
PD56 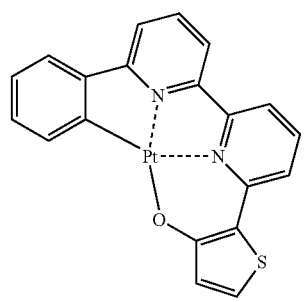
PD57 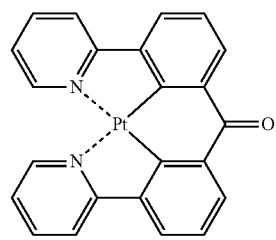
PD58 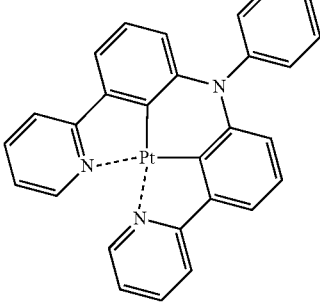
PD59 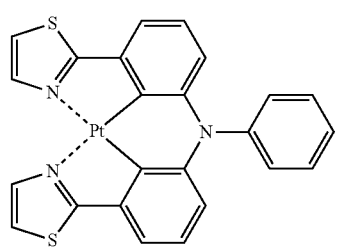

PD60 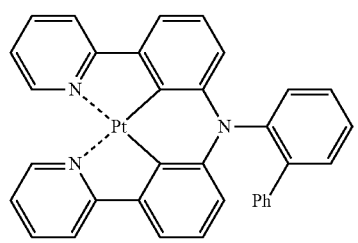
PD61 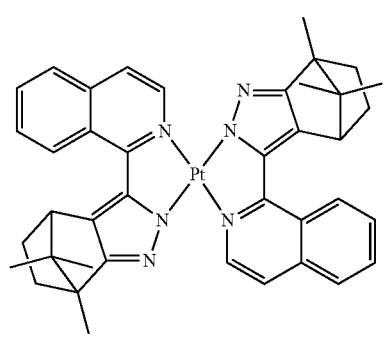
PD62 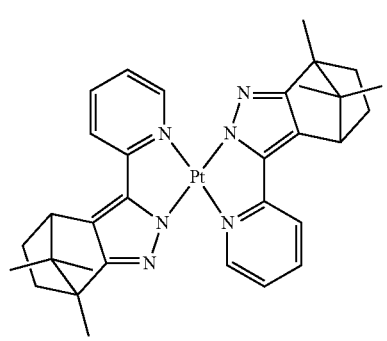
PD63 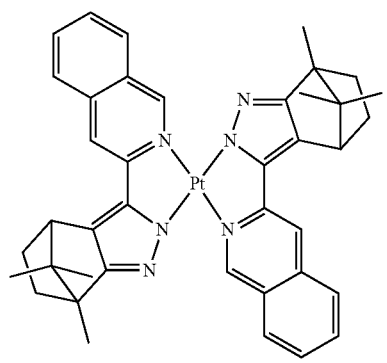
PD64 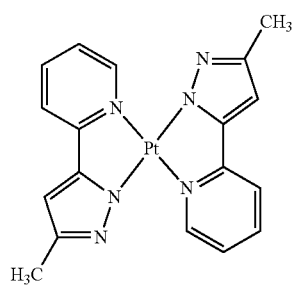
PD65 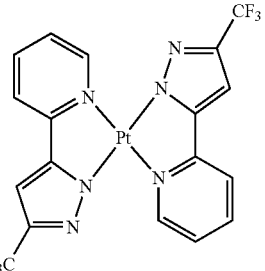
PD66 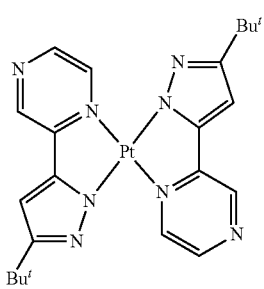
PD67 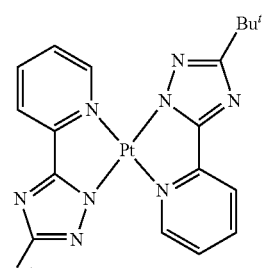
PD68 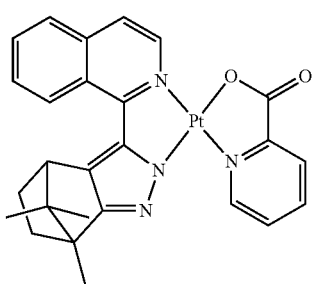
PD69 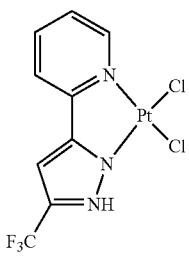
PD70 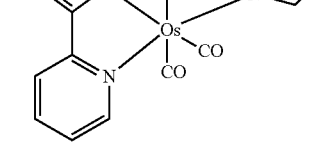

-continued
PD71
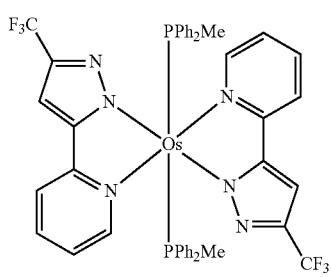
PD72
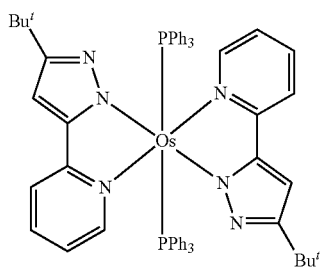
PD73
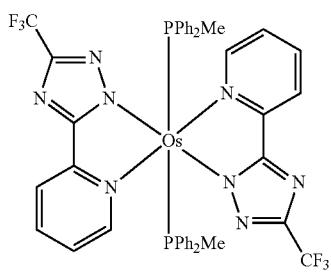
-continued
PD74
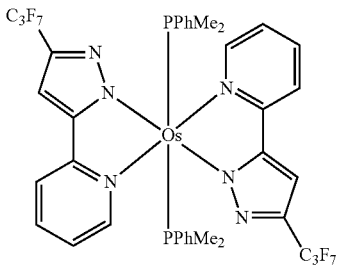
In an implementation, the phosphorescent dopant may include PtOEP.
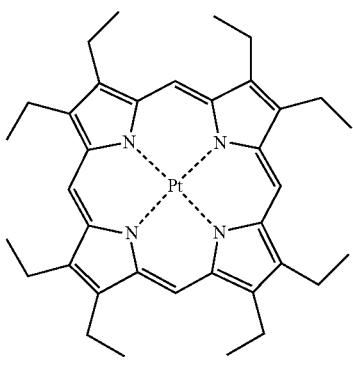
PtOEP
In an implementation, the fluorescent dopant may include at least one selected from DPAVBi, BDAVBi, TBPe, DCM, DCJTB, Coumarin 6, and C545T.
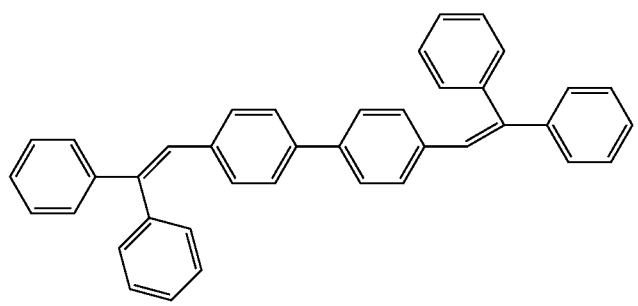
DPVBi
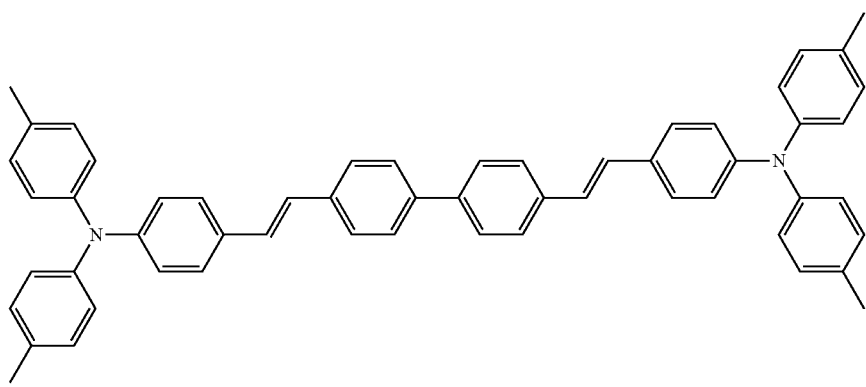
DPAVBi -continued

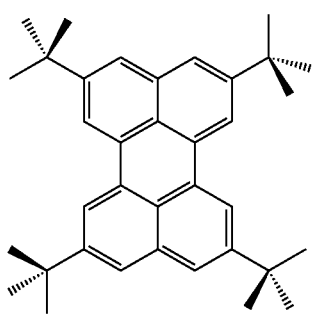

TBPe

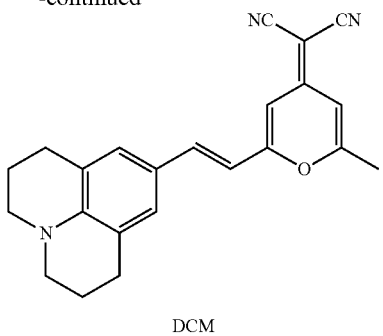

DCM

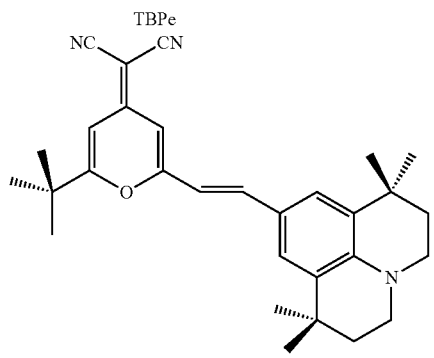

DCJTB

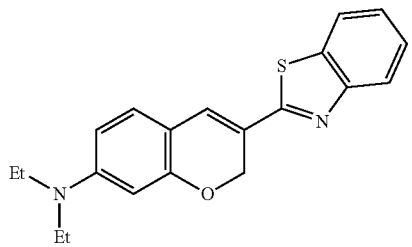

Coumarin 6

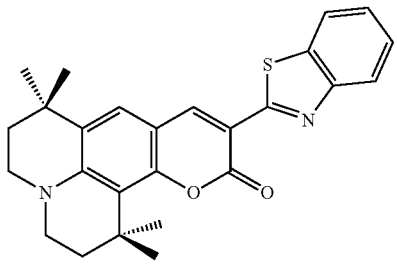

C545T

In an implementation, the fluorescent dopant may include a compound represented by Formula 501 below.

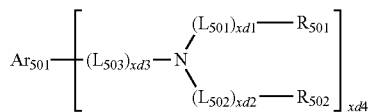

<Formula 501>

In Formula 501, $Ar_{501}$ may be:

a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, or an indenoanthracene; or a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ are each independently selected from a hydrogen, a $C_1$-$C_{60}$ alkyl group, a $C_2$-$C_{60}$ alkenyl group, a $C_1$-$C_{60}$ aryl group, and a $C_1$-$C_{60}$ heteroaryl group);

$L_{501}$ to $L_{503}$ are the same as explained in connection with $L_{201}$;

$R_{501}$ and $R_{502}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may each independently be selected from 0, 1, 2, and 3; and xb4 may be selected from 1, 2, 3, and 4.

An amount of the dopant in the emission layer may be, e.g., in a range of about 0.01 part by weight to about 15 parts by weight, based on 100 parts by weight of the host.

A thickness of the emission layer may be in a range of about 100 Å to about 1,000 Å, e.g., about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer.

For example, the electron transport region may have a structure of electron transport layer/electron injection layer or a structure of hole blocking layer/electron transport layer/electron injection layer, wherein layers of each structure are sequentially stacked from the emission layer in the stated order.

In an implementation, the organic layer 150 of the organic light-emitting device may include an electron transport region between the emission layer and the second electrode 190.

The electron transport region may include a hole blocking layer. The hole blocking layer may be formed, when the emission layer includes a phosphorescent dopant, to help prevent diffusion of excitons or holes into an electron transport layer.

When the electron transport region includes a hole blocking layer, the hole blocking layer may be formed on the emission layer by using various methods, e.g., vacuum deposition, spin coating casting, a LB method, ink-jet printing, laser-printing, or laser-induced thermal imaging. When the hole blocking layer is formed by vacuum deposition or spin coating, deposition and coating conditions for the hole blocking layer may be determined by referring to the deposition and coating conditions for the hole injection layer.

The hole blocking layer may include, e.g., at least one selected from BCP and Bphen.

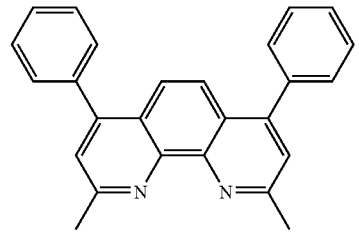

BCP

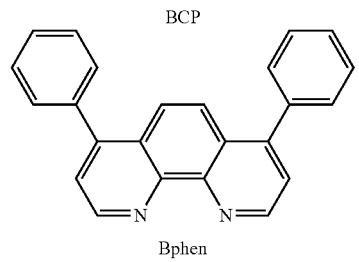

Bphen

A thickness of the hole blocking layer may be in a range of about 20 Å to about 1,000 Å, e.g., about 30 Å to about 300 Å. When the thickness of the hole blocking layer is within these ranges, the hole blocking layer may have improved hole blocking ability without a substantial increase in driving voltage.

The electron transport region may include an electron transport layer. The electron transport layer may be formed on the emission layer or the hole blocking layer by using various methods, e.g., vacuum deposition, spin coating, casting, a LB method, ink-jet printing, laser-printing, or laser-induced thermal imaging. When an electron transport layer is formed by vacuum deposition or spin coating, deposition and coating conditions for the electron transport layer may be determined by referring to the deposition and coating conditions for the hole injection layer.

In an implementation, the organic layer 150 of the organic light-emitting device may include an electron transport region between the emission layer and the second electrode 190. The electron transport region may include at least one selected from an electron transport layer and an electron injection layer.

The electron transport layer may further include at least one selected from BCP, Bphen, $Alq_3$, Balq, TAZ, and NTAZ.

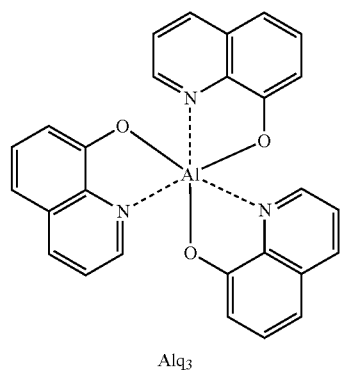

$Alq_3$

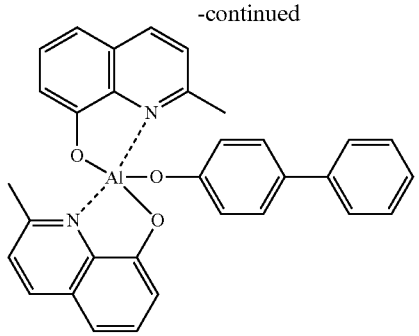

BAlq

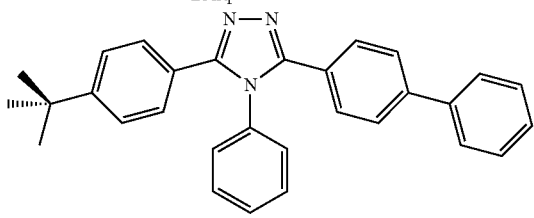

TAZ

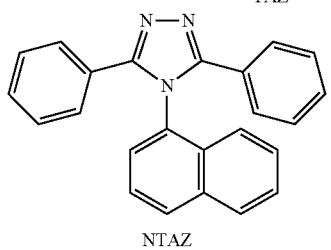

NTAZ

In an implementation, the electron transport layer may include at least one compound selected from a compound represented by Formula 601 and a compound represented by Formula 602 illustrated below.

$$Ar_{601}\text{-}[(L_{601})_{xe1}\text{-}E_{601}]_{xe2} \quad \text{<Formula 601>}$$

In Formula 601, $Ar_{601}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene and an indenoanthracene;

a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ are each independently selected from a hydrogen, a $C_1$-$C_{60}$ alkyl group, a $C_2$-$C_{60}$ alkenyl group, a $C_1$-$C_{60}$ aryl group, and a $C_1$-$C_{60}$ heteroaryl group);

$L_{601}$ may be the same as explained in connection with $L_{201}$;

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3; and
xe2 may be selected from 1, 2, 3, and 4.

<Formula 602>

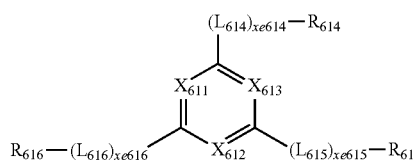

In Formula 602, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, and at least one selected from $X_{611}$ to $X_{613}$ may be N;

$L_{611}$ to $L_{616}$ may be the same as explained in connection with $L_{201}$;

$R_{611}$ to $R_{616}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

The compound represented by Formula 601 and/or the compound represented by Formula 602 may each independently be selected from Compounds ET1 to ET15 illustrated below.

ET1

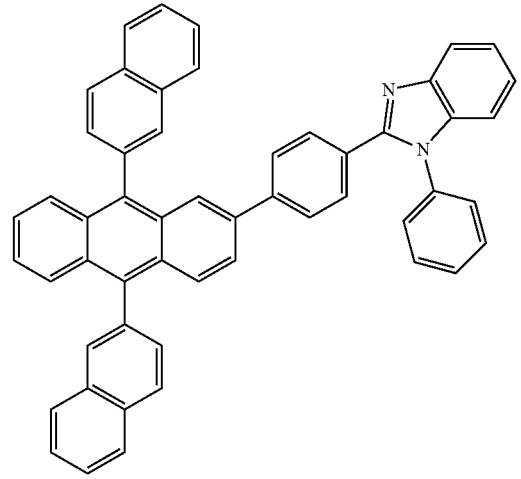

ET2

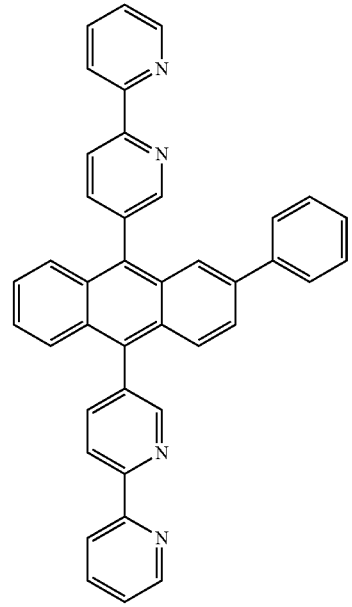

ET3

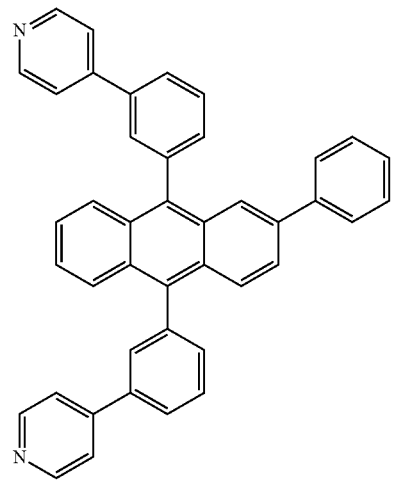

ET4
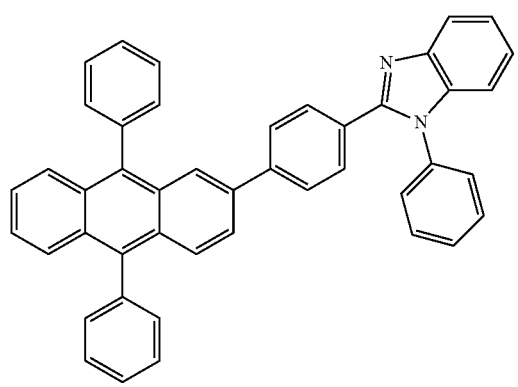
ET5
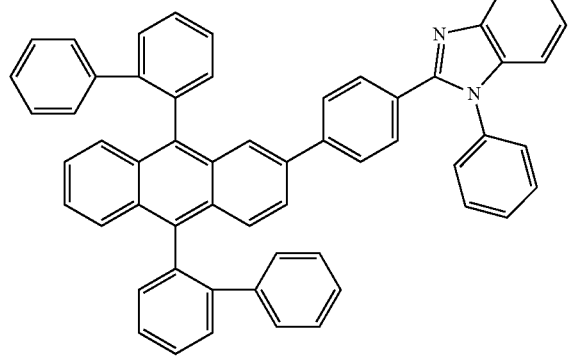
ET6
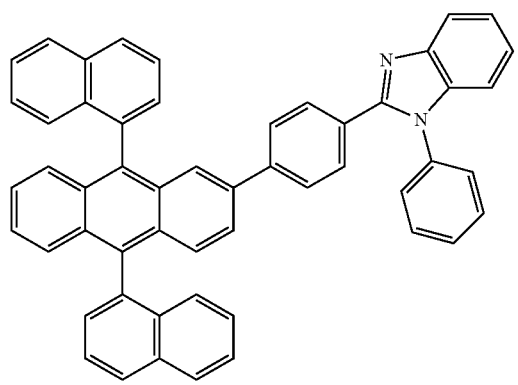
ET7
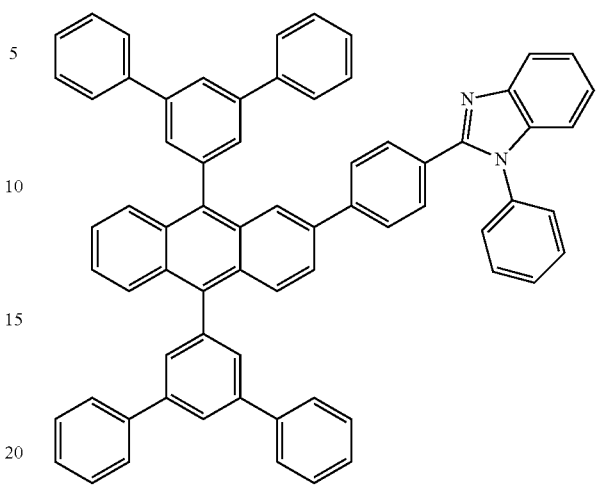
ET8
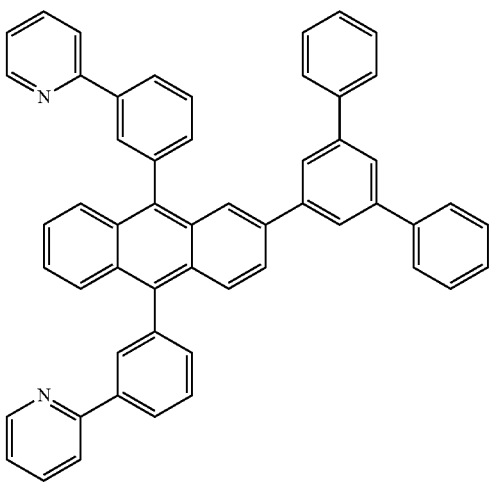
ET9
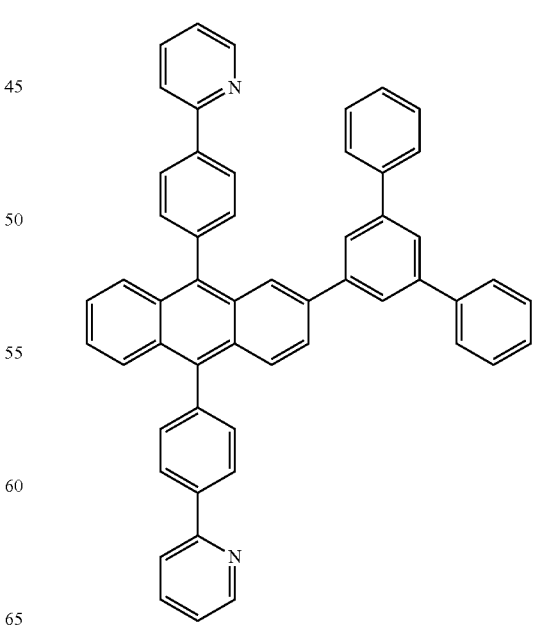

ET10
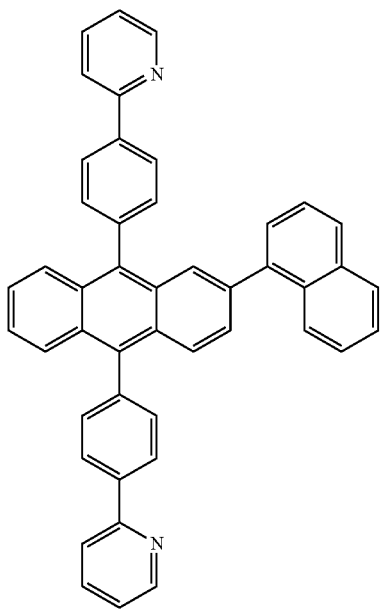

ET13
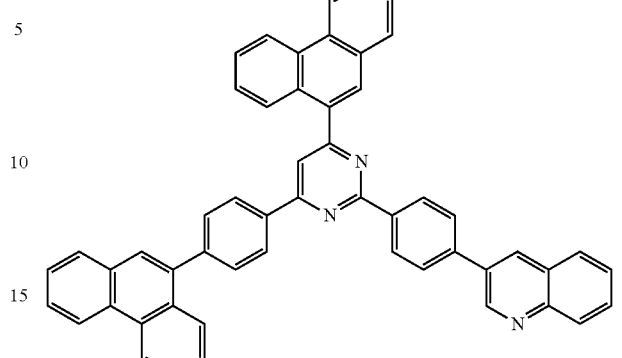

ET14
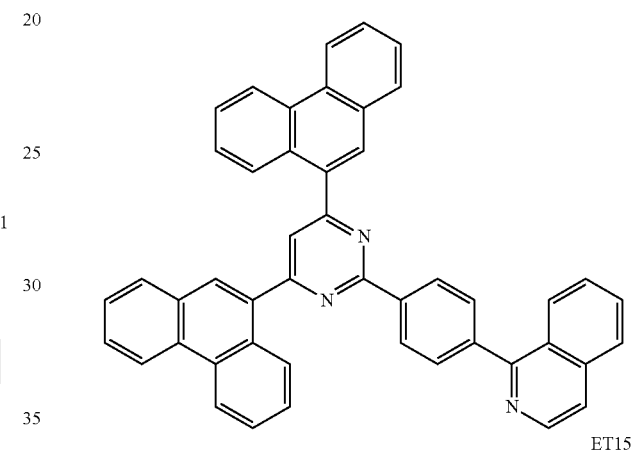

ET11
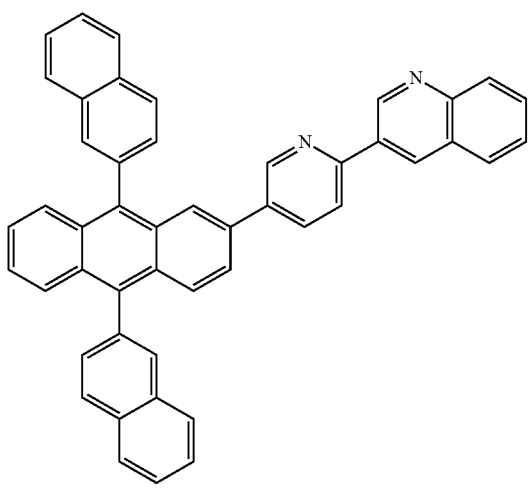

ET15
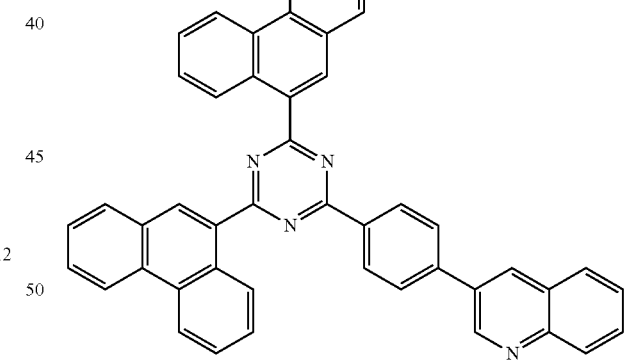

ET12
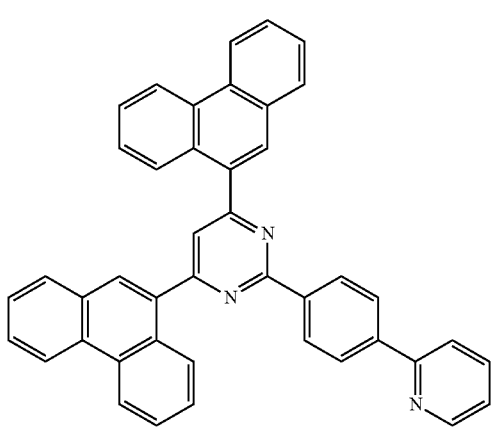

A thickness of the electron transport layer may be in a range of about 100 Å to about 1,000 Å, e.g., about 150 Å to about 500 Å. When the thickness of the electron transport layer is within the range described above, the electron transport layer may have satisfactory electron transport characteristics without a substantial increase in driving voltage.

In an implementation, the electron transport layer may further include, in addition to the materials described above, a metal-containing material.

The metal-containing material may include a Li complex. The Li complex may include, for example, Compound ET-D1 (lithium quinolate, LiQ) or ET-D2.

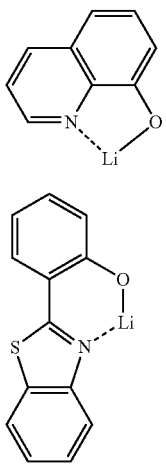

ET-D1

ET-D2

The electron transport region may include an electron injection layer that allows electrons to be easily provided from the second electrode 190.

The electron injection layer may be formed on the electron transport layer by using various methods, e.g., vacuum deposition, spin coating, casting, a LB method, ink-jet printing, laser-printing, or laser-induced thermal imaging. When an electron injection layer is formed by vacuum deposition or spin coating, deposition and coating conditions for the electron injection layer may be determined by referring to the deposition and coating conditions for the hole injection layer.

The electron injection layer may include at least one selected from, LiF, NaCl, CsF, $Li_2O$, BaO, and LiQ.

A thickness of the electron injection layer may be in a range of about 1 Å to about 100 Å, e.g., about 3 Å to about 90 Å. When the thickness of the electron injection layer is within the range described above, the electron injection layer may have satisfactory electron injection characteristics without a substantial increase in driving voltage.

The second electrode 190 may be disposed on the organic layer 150 having such a structure. The second electrode 190 may be a cathode that is an electron injection electrode, and in this regard, a material for forming the second electrode 190 may be a material having a low work function. Such a material may include a metal, alloy, an electrically conductive compound, or a mixture thereof. Examples of the material for the second electrode 190 may include lithium (Li), magnesium (Mg), aluminum (Al), aluminum-lithium (Al—Li), calcium (Ca), magnesium-indium (Mg—In), or magnesium-silver (Mg—Ag). In some embodiments, the material for forming the second electrode 190 may be ITO or IZO. The second electrode 190 may be a reflective electrode, a semi-transmissive electrode, or a transmissive electrode.

Hereinbefore, the organic light-emitting device has been described with reference to FIG. 1.

A $C_1$-$C_{60}$ alkyl group used herein refers to a linear or branched aliphatic hydrocarbon monovalent group having 1 to 60 carbon atoms, and detailed examples thereof include a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group), and detailed examples thereof include a methoxy group, an ethoxy group, and an isopropyloxy group.

A $C_2$-$C_{60}$ alkenyl group used herein refers to a hydrocarbon group formed by substituting at least one carbon double bond in the middle or at the terminal of the $C_2$-$C_{60}$ alkyl group, and detailed examples thereof include an ethenyl group, a prophenyl group, and a butenyl group. A $C_2$-$C_{60}$ alkylene group used herein refers to a divalent group having the same structure as the $C_2$-$C_{60}$ alkyl group.

A $C_2$-$C_{60}$ alkynyl group used herein refers to a hydrocarbon group formed by substituting at least one carbon triple bond in the middle or at the terminal of the $C_2$-$C_{60}$ alkyl group, and detailed examples thereof include an ethynyl group, and a propynyl group. A $C_2$-$C_{60}$ alkylene group used herein refers to a divalent group having the same structure as the $C_2$-$C_{60}$ alkyl group.

A $C_3$-$C_{10}$ cycloalkyl group used herein refers to a monovalent hydrocarbon monocyclic group having 3 to 10 carbon atoms, and detailed examples thereof include a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group having at least one hetero atom selected from N, O, P, and S as a ring-forming atom, and 1 to 10 carbon atoms, and detailed examples thereof include a tetrahydrofuranyl group and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity, and detailed examples thereof include a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one hetero atom selected from N, O, P, and S as a ring-forming atom, 1 to 10 carbon atoms, and at least one double bond in its ring. Detailed examples of the $C_1$-$C_{10}$ heterocycloalkenyl group include a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group used herein refers to a monovalent group having a carbocyclic aromatic system that has at least one hetero atom selected from N, O, P, and S as a ring-forming atom, and 1 to 60 carbon atoms. A $C_1$-$C_{60}$ heteroarylene group used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group used herein refers to a monovalent group (e.g., having 8 to 60 carbon atoms) that has two or more rings condensed to each other, only carbon atoms as a ring forming atom, and non-aromaticity in the entire molecular structure. Detailed examples of the monovalent non-aromatic condensed polycyclic group include a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group (e.g., having 1 to 60 carbon atoms) that has two or more rings condensed to each other, has a heteroatom selected from N, O P, and S, other than carbon atoms, as a ring forming atom, and has non-aromaticity in the entire molecular structure. Examples of the monovalent non-aromatic condensed heteropolycyclic group include a carbazolyl group. A divalent non-aromatic condensed heteropolycyclic group used herein refers to a divalent group having the same structure as the monovalent non-aromatic condensed heteropolycyclic group.

At least one substituent of the substituted $C_6$-$C_{20}$ aromatic ring, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_1$-$C_{60}$ heteroaryl group, substituted monovalent non-aromatic condensed polycyclic group and substituted monovalent non-aromatic condensed heteropolycyclic group, may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), and —B($Q_{14}$)($Q_{15}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —Si($Q_{21}$)($Q_{22}$)($Q_{23}$), and —B($Q_{24}$)($Q_{25}$); and —Si($Q_{31}$)($Q_{32}$)($Q_{33}$) and —B($Q_{34}$)($Q_{35}$), wherein $Q_{11}$ to $Q_{15}$, $Q_{21}$ to $Q_{25}$, and $Q_{31}$ to $Q_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, the at least one substituent of the substituted $C_6$-$C_{20}$ aromatic ring, $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted a divalent non-aromatic condensed polycyclic group, substituted a divalent non-aromatic condensed heteropolycyclic group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_1$-$C_{60}$ heteroaryl group, substituted monovalent non-aromatic condensed polycyclic group and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —Si($Q_{11}$)($Q_{12}$)($Q_{12}$)($Q_{13}$), and —B($Q_{14}$)($Q_{15}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, —Si($Q_{21}$)($Q_{22}$)($Q_{23}$), and —B($Q_{24}$)($Q_{25}$); and —Si($Q_{31}$)($Q_{32}$)($Q_{33}$) and —B($Q_{34}$)($Q_{35}$), wherein $Q_{11}$ to $Q_{15}$, $Q_{21}$ to $Q_{25}$, and $Q_{31}$ to $Q_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The term "Ph" used herein refers to a phenyl group, the term "Me" used herein refers to a methyl group, the term "Et" used herein refers to an ethyl group, and the term "ter-Bu" or "But" used herein refers to a tert-butyl group.

Hereinafter, an organic light-emitting device according to an embodiment will be described in detail with reference to Synthesis Examples and Examples. The expression "B was used instead of A" used in describing Synthesis Examples means that a molar equivalent of A was identical to a molar equivalent of B.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Example

Synthesis Example 1: Synthesis of Compound 1

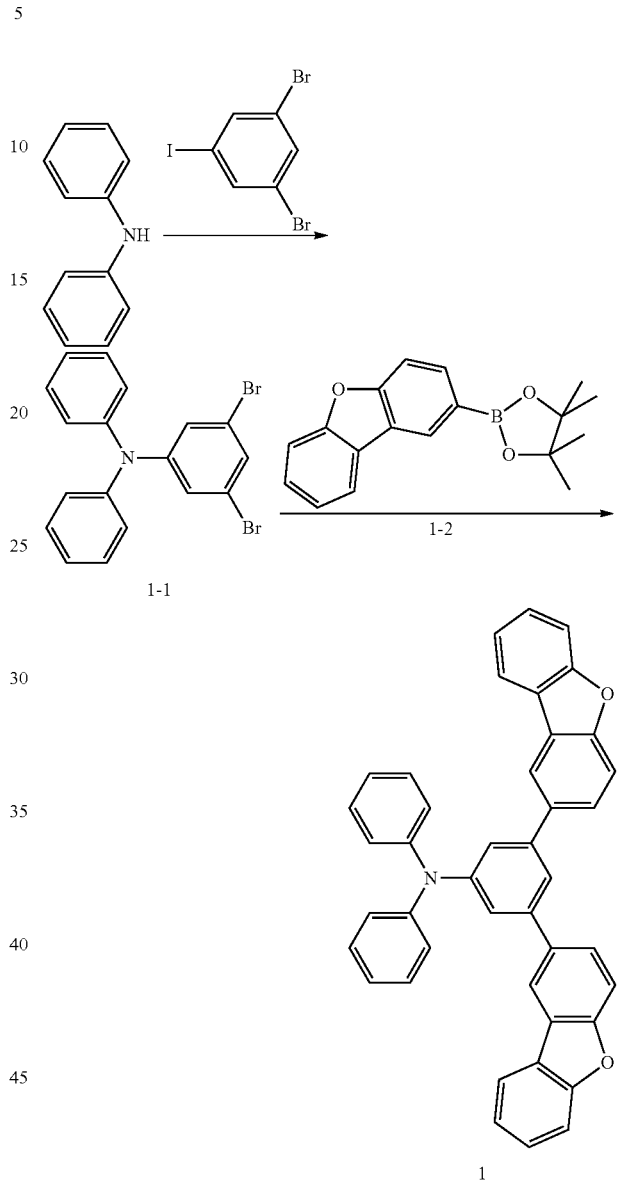

Synthesis of Intermediate 1-1

0.85 g (5.0 mmol) of diphenylamine, 1.41 g (5.0 mmol) of 1,3-dibromo-5-iodobenzene, 0.09 g (0.1 mmol) of $Pd_2(dba)_3$, 0.01 g (0.1 mmol) of $PtBu_3$ and 1.38 g (10.0 mmol) of KOtBu were dissolved in 20 mL of toluene and the resultant was stirred at a temperature of 85° C. for 2 hours. The reaction solution was cooled to ambient temperature, and then extracted three times with 20 mL of water and 20 mL of diethyl ether. A collected organic layer was dried by using magnesium sulfate, and then, the residual obtained by evaporating a solvent therefrom was separation-purified by silica gel column chromatography to obtain 1.38 g (yield of 85%) of Intermediate 1-1. LC/MS cal: 400.94. found: 401.94.

Synthesis of Intermediate 1-2

10 g of 2-bromodibenzo[b,d]furan was diluted in 150 ml of tetrahydrofuran (THF) and the resultant was cooled to a temperature of −78° C. At a temperature of −78° C., 2.5 M (14.7 ml) of n-BuLi was dropwise added thereto. After 1 hour, 3 g of 2-isopropoxy-4,4,5,5-tetramethyl-1,3,2-dioxaborolane was slowly added thereto. After 30 minutes, the resultant was slowly heated to ambient temperature and then stirred for 6 hours. The reaction was terminated by adding a saturated aqueous ammonium chloride solution. An organic layer was separated therefrom and then dried by using anhydrous magnesium sulfate and concentrated at reduced pressure. The residual obtained therefrom was separation-purified by silica gel column chromatography to obtain 9.17 g (yield of 78%) of Intermediate 1-2. LC/MS cal: 294.14. found: 295.14.

Synthesis of Compound 1

7.42 g (20 mmol) of Intermediate 1-1, 11.76 g (40 mmol) of Intermediate 1-2, 2.3 g (2.0 mmol) of Pd(PPh$_3$)$_4$ and 8.28 g (60.0 mmol) of K$_2$CO$_3$ were dissolved in 60 mL of a mixed solution of THF/H$_2$O (2/1 volume ratio), and then the resultant was stirred at a temperature of 80° C. for 5 hours. The reaction solution was cooled to ambient temperature, and then extracted three times with 60 mL of water and 60 mL of diethyl ether. A collected organic layer was dried by using magnesium sulfate and then, the residual obtained by evaporating a solvent therefrom was separation-purified by silica gel column chromatography to obtain 7.73 g (yield of 67%) of Compound 1. The synthesized compound was confirmed by MS/FAB and $^1$H NMR.

Synthesis Example 2: Synthesis of Compound 21

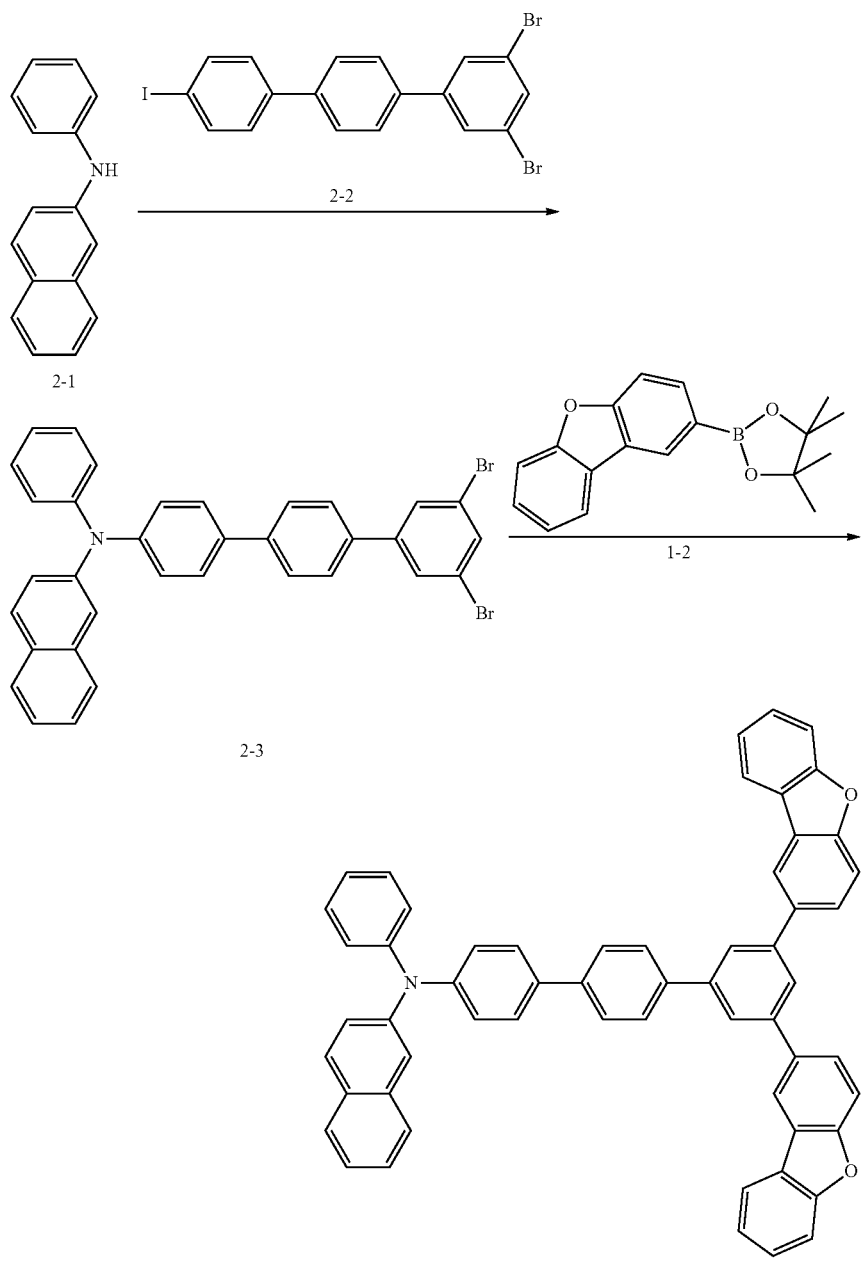

Synthesis of Intermediate 2-3

Intermediate 2-3 was obtained in the same manner as in the synthesis of Intermediate 1-1, except that Intermediate 2-1 was used instead of diphenylamine, and Intermediate 2-2 was used instead of 1,3-dibromo-5-iodobenzene.

Synthesis of Compound 21

Compound 21 was obtained in the same manner as in the synthesis of Compound 1, except that Intermediate 2-3 was used instead of Intermediate 1-1. The synthesized compound was confirmed by $^1$H NMR and MS/FAB Synthesis Example 3: Synthesis of Compound 29

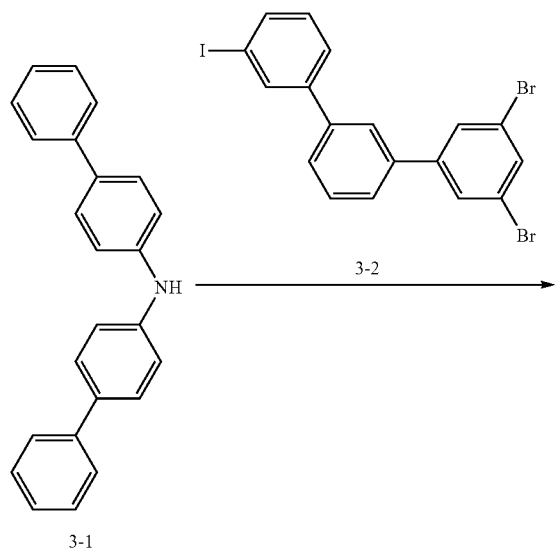

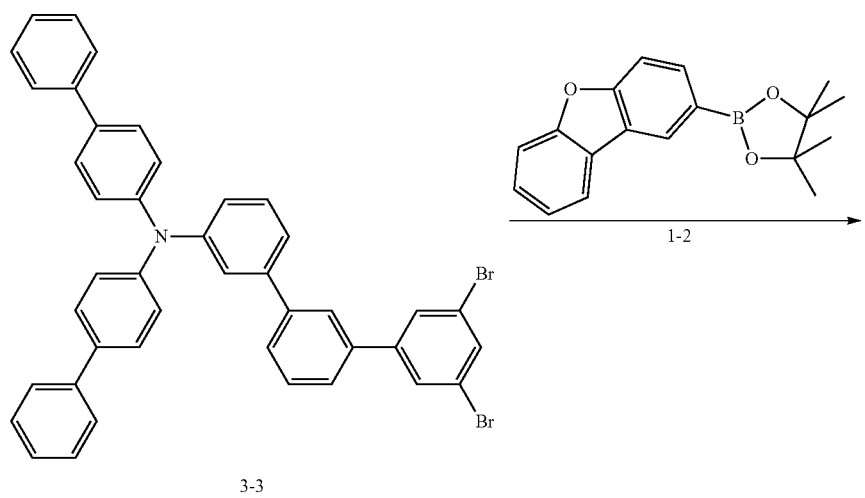

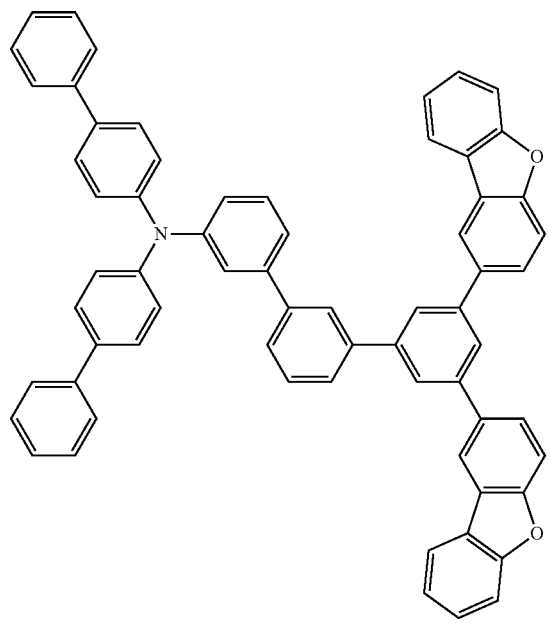

29

Synthesis of Intermediate 3-3

Intermediate 3-3 was obtained in the same manner as in the synthesis of Intermediate 1-1, except that Intermediate 3-1 was used instead of diphenylamine, and Intermediate 3-2 was used instead of 1,3-dibromo-5-iodobenzene. The obtained compound was confirmed by $^1$H NMR and MS/FAB.

Synthesis of Compound 29

Compound 29 was obtained in the same manner as in the synthesis of Compound 1, except that Intermediate 3-3 was used instead of Intermediate 1-1. The obtained compound was confirmed by $^1$H NMR and MS/FAB.

Synthesis Example 4: Synthesis of Compound 40

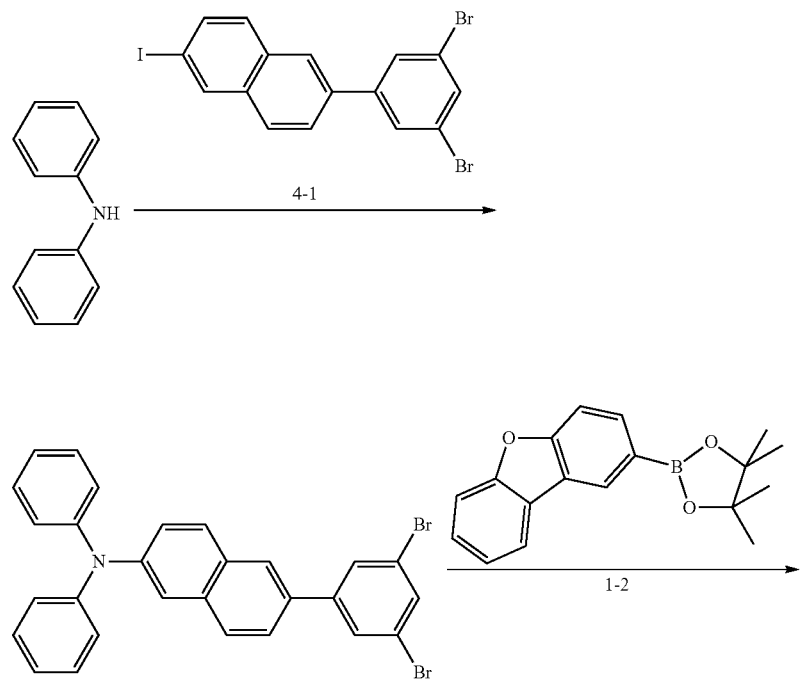

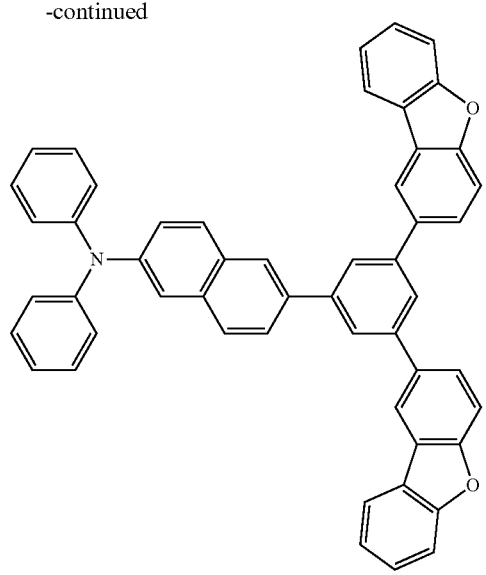

40

Synthesis of Intermediate 4-2

Intermediate 4-2 was obtained in the same manner as in the synthesis of Intermediate 1-1, except that Intermediate 4-1 was used instead of 1,3-dibromo-5-iodobenzene.

Synthesis of Compound 40

Compound 40 was obtained in the same manner as in the synthesis of Compound 1, except that Intermediate 4-2 was used instead of Intermediate 1-1. The obtained compound was confirmed by $^1$H NMR and MS/FAB.

Synthesis Example 5: Synthesis of Compound 49

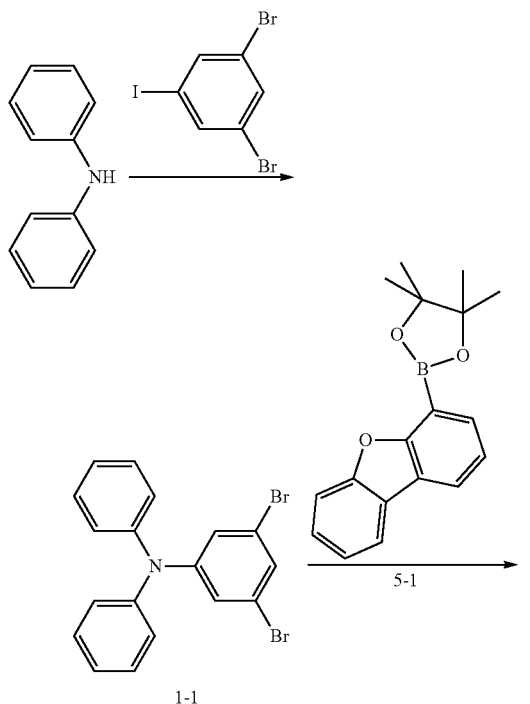

-continued

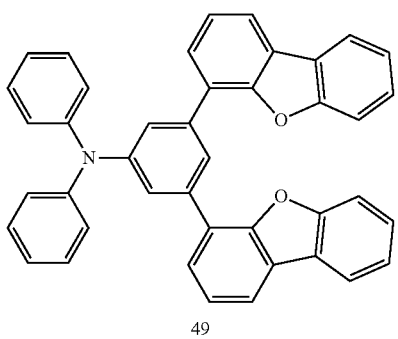

49

Synthesis of Intermediate 5-1

Intermediate 5-1 was obtained in the same manner as in the synthesis of Intermediate 1-2, except that 4-bromodibenzo[b,d]furan was used instead of 2-bromodibenzo[b,d]furan.

Synthesis of Compound 49

Compound 49 was obtained in the same manner as in the synthesis of Compound 1, except that Intermediate 5-1 was used instead of Intermediate 1-2. The synthesized compound was confirmed by $^1$H NMR and MS/FAB.

Synthesis Example 6: Synthesis of Compound 56

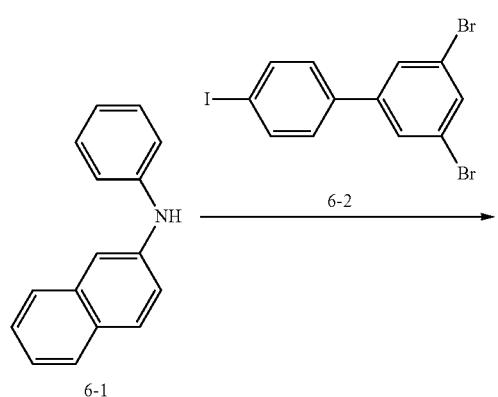

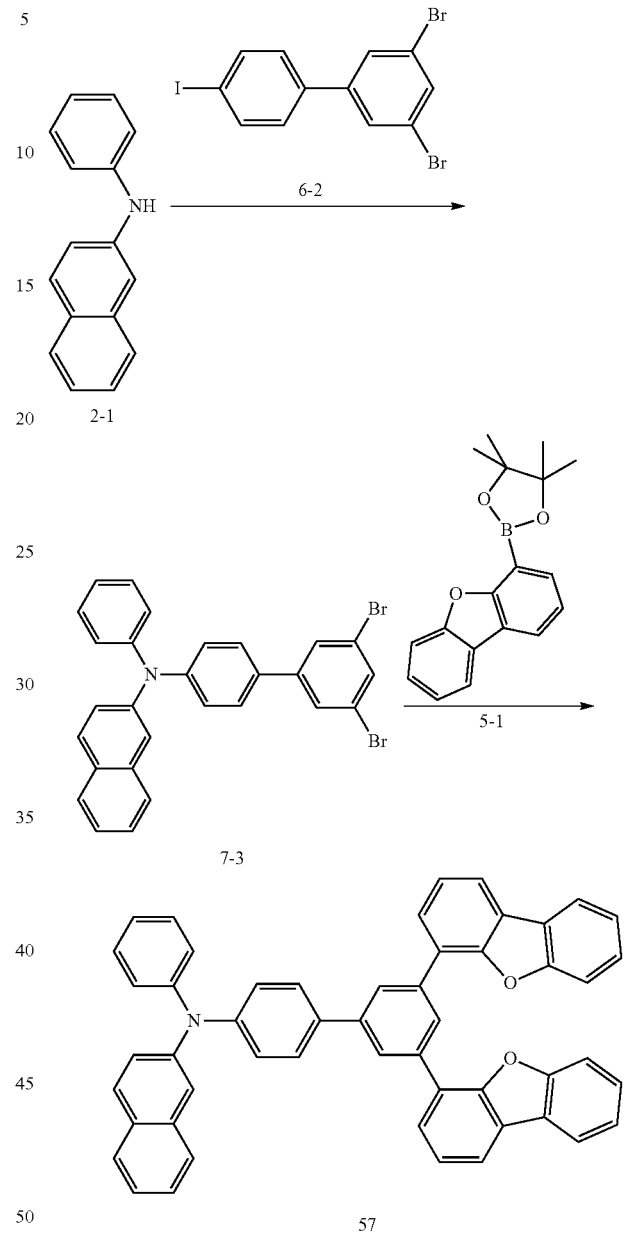

Synthesis of Intermediate 6-3

Intermediate 6-3 was obtained in the same manner as in the synthesis of Intermediate 1-1, except that Intermediate 6-1 was used instead of diphenylamine, and Intermediate 6-2 was used instead of 1,3-dibromo-5-iodobenzene.

Synthesis of Compound 56

Compound 56 was obtained in the same manner as in the synthesis of Compound 1, except that Intermediate 6-3 was used instead of Intermediate 1-1, and Intermediate 5-1 was used instead of Intermediate 1-2. The obtained compound was confirmed by $^1$H NMR and MS/FAB.

Synthesis Example 7: Synthesis of Compound 57

Synthesis of Intermediate 7-3

Intermediate 7-3 was obtained in the same manner as in the synthesis of Intermediate 1-1, except that Intermediate 2-1 was used instead of diphenylamine, and Intermediate 6-2 was used instead of 1,3-dibromo-5-iodobenzene.

Synthesis of Compound 57

Compound 57 was obtained in the same manner as in the synthesis of Compound 1, except that Intermediate 7-3 was used instead of Intermediate 1-1, and Intermediate 5-1 was used instead of Intermediate 1-2. The synthesized compound was confirmed by $^1$H NMR and MS/FAB.

Synthesis Example 8: Synthesis of Compound 59

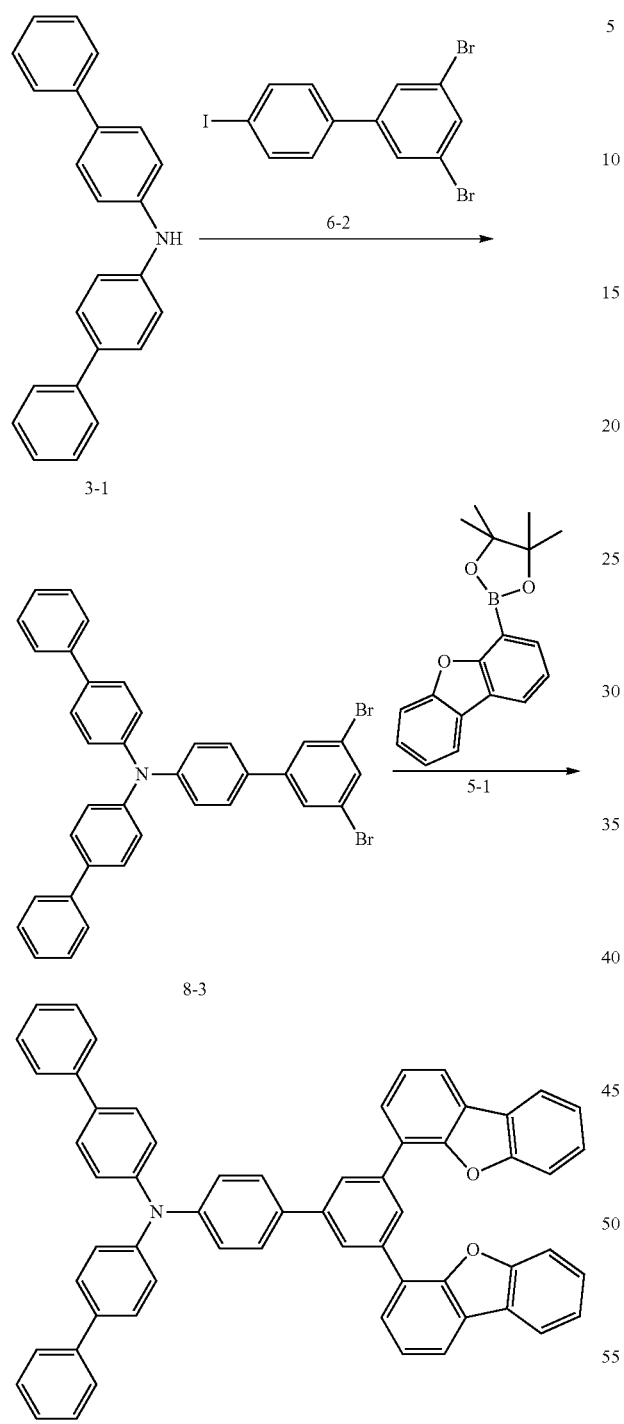

Synthesis of Intermediate 8-3

Intermediate 8-3 was obtained in the same manner as in the synthesis of Intermediate 1-1, except that Intermediate 3-1 was used instead of diphenylamine, and Intermediate 6-2 was used instead of 1,3-dibromo-5-iodobenzene.

Synthesis of Compound 59

Compound 59 was obtained in the same manner as in the synthesis of Compound 1, except that Intermediate 8-3 was used instead of Intermediate 1-1, and Intermediate 5-1 was used instead of Intermediate 1-2. The synthesized compound was confirmed by $^1$H NMR and MS/FAB.

Synthesis Example 9: Synthesis of Compound 62

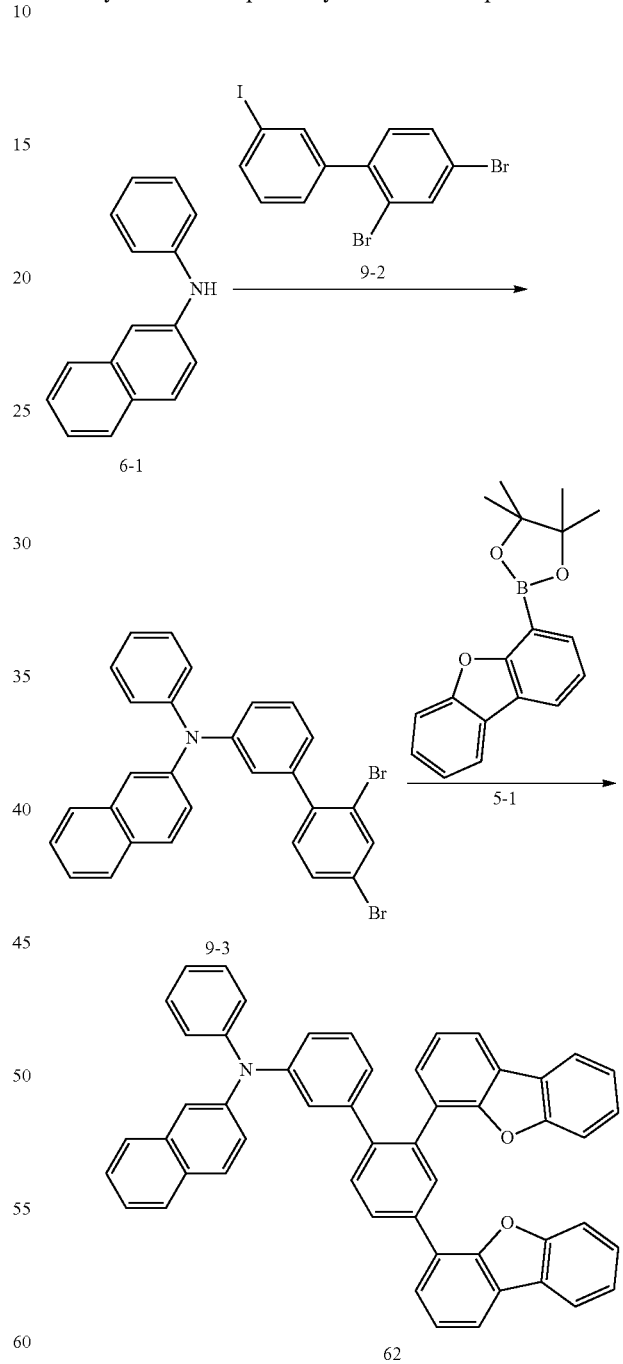

Synthesis of Intermediate 9-3

Intermediate 9-3 was obtained in the same manner as in the synthesis of Intermediate 1-1, except that Intermediate 6-1 was used instead of diphenylamine, and Intermediate 9-2 was used instead of 1,3-dibromo-5-iodobenzene.

Synthesis of Compound 62

Compound 62 was obtained in the same manner as in the synthesis of Compound 1, except that Intermediate 9-3 was used instead of Intermediate 1-1, and Intermediate 5-1 was used instead of Intermediate 1-2. The synthesized compound was confirmed by $^1$H NMR and MS/FAB.

Synthesis Example 10: Synthesis of Compound 63

Synthesis of Intermediate 10-1

Intermediate 10-1 was obtained in the same manner as in the synthesis of Intermediate 1-1, except that Intermediate 2-1 was used instead of diphenylamine, and Intermediate 9-2 was used instead of 1,3-dibromo-5-iodobenzene.

Synthesis of Compound 63

Compound 63 was obtained in the same manner as in the synthesis of Compound 1, except that Intermediate 10-1 was used instead of Intermediate 1-1, and Intermediate 5-1 was used instead of Intermediate 1-2. The synthesized compound was confirmed by $^1$H NMR and MS/FAB.

Synthesis Example 11: Synthesis of Compound 70

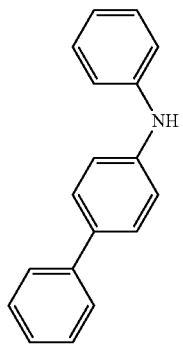

11-1

Synthesis of Intermediate 11-2

Intermediate 11-2 was obtained in the same manner as in the synthesis of Intermediate 1-1, except that Intermediate 11-1 was used instead of diphenylamine, and Intermediate 2-2 was used instead of 1,3-dibromo-5-iodobenzene.

Synthesis of Compound 70

Compound 70 was obtained in the same manner as in the synthesis of Compound 1, except that Intermediate 11-2 was used instead of Intermediate 1-1, and Intermediate 5-1 was used instead of Intermediate 1-2. The synthesized compound was confirmed by $^1$H NMR and MS/FAB.

Synthesis Example 12: Synthesis of Compound 74

Synthesis of Intermediate 12-1

Intermediate 12-1 was obtained in the same manner as in the synthesis of Intermediate 1-1, except that Intermediate 6-1 was used instead of diphenylamine, and Intermediate 3-2 was used instead of 1,3-dibromo-5-iodobenzene.

Synthesis of Compound 74

Compound 74 was obtained in the same manner as in the synthesis of Compound 1, except that Intermediate 12-1 was used instead of Intermediate 1-1, and Intermediate 5-1 was used instead of Intermediate 1-2. The synthesized compound was confirmed by $^1$H NMR and MS/FAB.

Synthesis Example 13: Synthesis of Compound 78

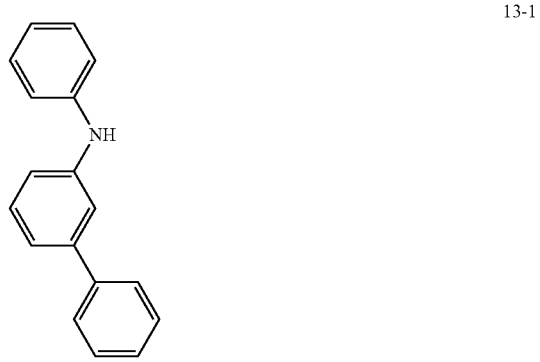 [SMILES: c1ccc(Nc2cccc(-c3ccccc3)c2)cc1]

13-1

Synthesis of Intermediate 13-2

Intermediate 13-2 was obtained in the same manner as in the synthesis of Intermediate 1-1, except that Intermediate 13-1 was used instead of diphenylamine, and Intermediate 3-2 was used instead of 1,3-dibromo-5-iodobenzene.

Synthesis of Compound 78

Compound 78 was obtained in the same manner as in the synthesis of Compound 1, except that Intermediate 13-2 was used instead of Intermediate 1-1, and Intermediate 5-1 was used instead of Intermediate 1-2. The synthesized compound was confirmed by $^1$H NMR and MS/FAB.

Synthesis Example 14: Synthesis of Compound 85

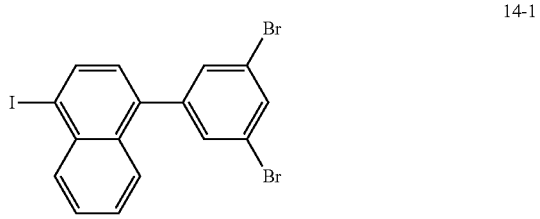 [SMILES: Brc1cc(Br)cc(-c2ccc(I)c3ccccc23)c1]

14-1

Synthesis of Intermediate 14-2

Intermediate 14-2 was obtained in the same manner as in the synthesis of Intermediate 1-1, except that Intermediate 14-1 was used instead of 1,3-dibromo-5-iodobenzene.

Synthesis of Compound 85

Compound 85 was obtained in the same manner as in the synthesis of Compound 1, except that Intermediate 14-2 was used instead of Intermediate 1-1, and Intermediate 5-1 was used instead of Intermediate 1-2. The synthesized compound was confirmed by $^1$H NMR and MS/FAB.

Synthesis Example 15: Synthesis of Compound 89

Synthesis of Intermediate 15-1

Intermediate 15-1 was obtained in the same manner as in the synthesis of Intermediate 1-1, except that Intermediate 6-1 was used instead of diphenylamine, and Intermediate 4-1 was used instead of 1,3-dibromo-5-iodobenzene.

Synthesis of Compound 89

Compound 89 was obtained in the same manner as in the synthesis of Compound 1, except that Intermediate 15-1 was used instead of Intermediate 1-1, and Intermediate 5-1 was used instead of Intermediate 1-2. The synthesized compound was confirmed by $^1$H NMR and MS/FAB.

Synthesis Example 16: Synthesis of Compound 90

Synthesis of Intermediate 16-1

Intermediate 16-1 was obtained in the same manner as in the synthesis of Intermediate 1-1, except that Intermediate 11-1 was used instead of diphenylamine, and Intermediate 4-1 was used instead of 1,3-dibromo-5-iodobenzene.

Synthesis of Compound 89

Compound 90 was obtained in the same manner as in the synthesis of Compound 1, except that Intermediate 16-1 was used instead of Intermediate 1-1, and Intermediate 5-1 was used instead of Intermediate 1-2. The synthesized compound was confirmed by $^1$H NMR and MS/FAB.

Synthesis Example 17: Synthesis of Compound 98

Synthesis of Intermediate 17-1

Intermediate 17-1 was obtained in the same manner as in the synthesis of Intermediate 1-1, except that Intermediate 6-1 was used instead of diphenylamine.

Synthesis of Intermediate 17-2

Intermediate 17-2 was obtained in the same manner as in the synthesis of Intermediate 1-2, except that 3-bromodibenzo[b,d]furan was used instead of 2-bromodibenzo[b,d]furan.

Synthesis of Compound 98

Compound 98 was obtained in the same manner as in the synthesis of Compound 1, except that Intermediate 17-1 was used instead of Intermediate 1-1, and Intermediate 17-2 was used instead of Intermediate 1-2. The synthesized compound was confirmed by $^1$H NMR and MS/FAB.

Synthesis Example 18: Compound 102

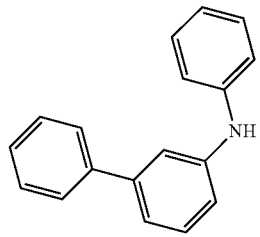

18-1

Synthesis of Intermediate 18-2

Intermediate 18-2 was obtained in the same manner as in the synthesis of Intermediate 1-1, except that Intermediate 18-1 was used instead of diphenylamine.

Synthesis of Compound 102

Compound 102 was obtained in the same manner as in the synthesis of Compound 1, except that Intermediate 18-2 was used instead of Intermediate 1-1, and Intermediate 17-2 was used instead of Intermediate 1-2. The synthesized compound was confirmed by $^1$H NMR and MS/FAB.

Synthesis Example 19: Synthesis of Compound 106

Synthesis of Intermediate 19-1

Intermediate 19-1 was obtained in the same manner as in the synthesis of Intermediate 1-1, except that Intermediate 11-1 was used instead of diphenylamine, and Intermediate 6-2 was used instead of 1,3-dibromo-5-iodobenzene.

Synthesis of Compound 106

Compound 106 was obtained in the same manner as in the synthesis of Compound 1, except that Intermediate 19-1 was used instead of Intermediate 1-1, and Intermediate 17-2 was used instead of Intermediate 1-2. The synthesized compound was confirmed by $^1$H NMR and MS/FAB.

Synthesis Example 20: Synthesis of Compound 110

Synthesis of Intermediate 20-1

Intermediate 20-1 was obtained in the same manner as in the synthesis of Intermediate 1-1, except that Intermediate 6-1 was used instead of diphenylamine, and Intermediate 3-2 was used instead of 1,3-dibromo-5-iodobenzene.

Synthesis of Compound 110

Compound 110 was obtained in the same manner as in the synthesis of Compound 1, except that Intermediate 20-1 was used instead of Intermediate 1-1, and Intermediate 17-2 was used instead of Intermediate 1-2. The synthesized compound was confirmed by $^1$H NMR and MS/FAB $^1$H NMR, MS/FAB, and yields of the synthesized compounds are shown in Table 1 below.

TABLE 1

| Compound | ¹H NMR (CDCl₃, 400 MHz) | MS/FAB found | MS/FAB calc. | yield of (%) |
|---|---|---|---|---|
| 1 | δ = 8.01 (s, 2H), 7.89 (d, 2H), 7.81-7.79 (d, 2H), 7.61-7.59 (m, 3H), 7.51-7.49 (d, 2H), 7.45-7.30 (m, 4H), 7.09-7.07 (m, 4H), 6.89 (s, 2H), 6.66-6.63(m, 2H), 6.23-6.21 (d, 4H) | 578.20 | 577.20 | 67 |
| 21 | δ = 8.06 (s, 2H), 7.93-7.91 (m, 5H), 7.78-7.74 (m, 5H), 7.68-7.65 (m, 4H), 7.51-7.30 (m, 13H), 7.14-7.04 (m, 3H), 6.85-6.83 (m, 2H), 6.65-6.63 (m, 1H), 6.24-6.22 (d, 2H) | 780.28 | 779.28 | 65 |
| 29 | δ = 8.06 (s, 2H), 8.01-7.89 (m, 5H), 7.77 (s, 3H), 7.70-7.58 (m, 9H), 7.46-7.10 (m, 17H), 7.08-6.99 (m, 2H), 6.60-6.57 (m, 4H), 6.24-6.21 (m, 1H) | 882.32 | 881.32 | 58 |
| 40 | δ = 8.08-8.06 (m, 3H), 7.93-7.91 (m, 4H), 7.77 (m, 5H), 7.66-7.64 (m, 4H), 7.38-7.32 (m, 7H), 7.04-6.97 (m, 4H), 6.66-6.63 (m, 2H), 6.18-6.16 (d, 4H) | 704.25 | 703.25 | 68 |
| 49 | δ = 7.91-7.88 (m, 5H), 7.70 (d, 2H), 7.59-7.54 (m, 4H), 7.34-7.23 (m, 4H), 7.07 (m, 4H), 6.91 (s, 2H), 6.66-6.63 (m, 2H), 6.23-6.21 (d, 4H) | 578.20 | 577.20 | 79 |
| 56 | δ = 8.07 (s, 1H), 7.90-7.82 (m, 9H), 7.59-7.52 (m, 12H), 7.36-7.34 (m, 3H), 7.14-7.04 (m, 3H), 6.66-6.63 (m, 3H), 6.24-6.22 (s, 2H) | 704.25 | 703.25 | 71 |
| 57 | δ = 8.07 (m, 1H), 7.86-7.82 (m, 9H), 7.59-7.52 (m, 9H), 7.34 (m, 1H), 7.14-7.04 (m, 6H), 6.66-6.63 (m, 3H), 6.24-6.22 (m, 2H) | 704.25 | 703.25 | 70 |
| 59 | δ = 8.07-8.06 (m, 1H), 7.91-7.82 (m, 8H), 7.58-7.44 (m, 20H), 7.38-7.30 (m, 4H), 6.85-6.81 (m, 4H), 6.67-6.63 (m, 2H) | 806.29 | 805.29 | 70 |
| 62 | δ = 8.22 (d, 1H), 7.94-7.82 (m, 7H), 7.78-7.75 (dd, 1H), 7.62-7.50 (m, 9H), 7.46-7.43(m, 1H), 7.37-7.36 (d, 1H), 7.34-7.30 (m, 3H), 7.26-7.24 (m, 1H), 7.15-7.05 (m, 4H), 7.00 (m, 1H) | 704.25 | 703.25 | 64 |
| 63 | δ = 8.22 (d, 1H), 7.94-7.82 (m, 7H), 7.77-7.75 (dd, 1H), 7.62 (d, 1H), 7.60-7.50 (m, 8H), 7.46-7.43 (m, 1H), 7.37-7.36 (m, 1H), 7.34-7.30 (m, 3H), 7.25-7.24 (m, 1H), 7.15-7.07 (m, 4H), 7.00(m, 1H) | 704.29 | 703.25 | 58 |
| 70 | δ = 8.07-8.06 (m, 1H), 7.99-7.98 (d, 2H), 7.91-7.82 (m, 8H), 7.68-7.64 (m, 2H), 7.60-7.42 (m, 14H), 7.38-7.30 (m, 3H), 7.08-7.03 (m, 2H), 6.85-6.81 (m, 4H) | 806.29 | 805.29 | 62 |
| 74 | δ = 8.04-8.03 (m, 1H), 8.01 (d, 2H), 7.91-7.82 (m, 8H), 7.71-7.50 (m, 12H), 7.46-7.43 (m, 1H), 7.37-7.36 (d, 1H), 7.34 (d, 1H), 7.32-7.30 (m, 1H), 7.26-7.24 (m, 1H), 7.15-7.14 (dd, 1H), 7.10-7.05 (m, 3H), 6.96-6.95 (m, 1H) | 780.29 | 779.28 | 60 |
| 78 | δ = 8.04-8.01 (m, 3H), 7.91-7.82 (m, 7H), 7.71-7.50 (m, 11H), 7.42-7.38 (m, 3H), 7.34-7.30 (m, 2H), 7.26-7.19 (m, 2H), 7.10-7.04 (m, 4H), 6.96-6.93 (m, 2H), 6.66-6.62 (m, 1H), 6.24-6.16 (m,4H) | 806.29 | 805.29 | 69 |
| 85 | δ = 8.11 (d, 1H), 8.02-8.00 (m, 1H), 7.91-7.87 (m, 4H), 7.84-7.82 (d, 2H), 7.76 (d, 2H), 7.68-7.63 (m, 1H), 7.59-7.48 (m, 8H), 7.43-7.41 (m, 1H), 7.34-7.30 (m, 2H), 7.08-7.01 (m, 5H), 6.65-6.61 (m, 2H), 6.08-6.04 (m, 4H) | 704.26 | 703.25 | 75 |
| 89 | δ = 8.14 (m, 1H), 8.04-8.01 (m, 3H), 7.91-7.72 (m, 9H), 7.59-7.43 (m, 11H), 7.37-7.30 (m, 4H), 7.15-7.03 (m, 4H), 6.67-6.62(m, 1H), 6.24-6.20 (1H) | 754.36 | 753.26 | 70 |
| 90 | δ = 8.14 (m, 1H), 8.04-8.01 (m, 3H), 7.91-7.72 (m, 7H), 7.59-7.43 (m, 13H), 7.38-7.30 (m, 4H), 7.09-7.04 (m, 3H), 6.67-6.62 (m, 1H), 6.54-6.50 (m, 2H), 6.25-6.21 (m, 3H) | 780.26 | 779.28 | 70 |
| 98 | δ = 8.24-8.23 (m, 1H), 7.97-7.94 (m, 2H), 7.88-7.80 (m, 5H), 7.59-7.49 (m, 5H), 7.46-7.36 (m, 6H), 7.25-7.21 (m, 2H), 7.11-7.06 (m, 2H), 6.87-6.85 (m, 3H), 6.67-6.63 (m, 2H), 6.28-6.24 (m, 3H) | 628.23 | 627.21 | 77 |
| 102 | δ = 8.24-8.23 (m, 1H), 7.97-7.94 (m, 2H), 7.86-7.84 (m, 2H), 7.80 (m, 2H), 7.57-7.49 (m, 4H), 7.44-7.35 (m, 7H), 7.25-7.19 (m, 3H), 7.11-7.04 (m, 3H), 6.93-6.91 (m, 1H), 6.84-6.83 (d, 2H), 6.66-6.62 (m, 1H), 6.28-6.24 (m, 1H), 5.92-5.89 (m, 2H) | 654.23 | 653.23 | 70 |
| 106 | δ = 7.99-7.96 (m, 2H), 7.86-7.84 (m, 2H), 7.74 (m, 2H), 7.69-7.66 (m, 3H), 7.58-7.56 (m, 2H), 7.51 (d, 1H), 7.49-7.43 (m, 9H), 7.40-7.34 (m, 3H), 7.25-7.21 (m, 2H), 7.08-7.03 (m, 2H), 6.85-6.81 (m, 2H), 6.67-6.57 (m, 3H), 6.23-6.19 (m, 2H) | 730.26 | 729.26 | 75 |
| 110 | δ = 7.99-7.96 (dd, 2H), 7.88-7.83 (m, 4H), 7.74-7.73 (m, 4H), 7.70-7.65 (m, 3H), 7.62-7.44 (m, 9H), 7.40-7.36 (m, 3H), 7.26-7.23 (m, 2H), 7.21 (d, 1H), 7.15-7.14 (dd, 1H), 7.10-7.05 (m, 3H), 6.96-6.95 (m, 1H), 6.67-6.62 (m, 1H), 6.24-6.17 (3H) | 780.28 | 779.28 | 69 |

Example 1

An ITO glass substrate (a product of Corning Co., Ltd) having a sheet resistance and thickness of 15 Ω/cm$^2$ and 1,200 Å was cut to a size of 50 mm×50 mm×0.7 mm, and then, sonicated by using isopropyl alcohol and pure water, each for 5 minutes, and cleaned by the exposure to ultraviolet rays for 30 minutes, and then ozone, and the ITO glass substrate was mounted on a vacuum deposition apparatus.

2-TNATA was vacuum-deposited on the ITO anode substrate to form a hole injection layer having a thickness of 600 Å, and then Compound 1 was vacuum-deposited on the hole injection layer to form a hole transport layer having a thickness of 300 Å.

9,10-di(naphthalen-2-yl)anthracene(ADN) (host) and N,N,N',N'-tetraphenyl-pyrene-1,6-diamine(TPD) (dopant) were co-deposited on the hole transport layer in a weight ratio of 98:2 to form an emission layer having a thickness of 300 Å.

Thereafter, Alq3 was deposited on the emission layer to form an electron transport layer having a thickness of 300 Å, and LiF was deposited on the electron transport layer to form an electron injection layer having a thickness of 10 Å, and Al was deposited on the electron injection layer to form a cathode having a thickness of 3,000 Å, thereby completing the manufacture of an organic light-emitting device.

Example 2

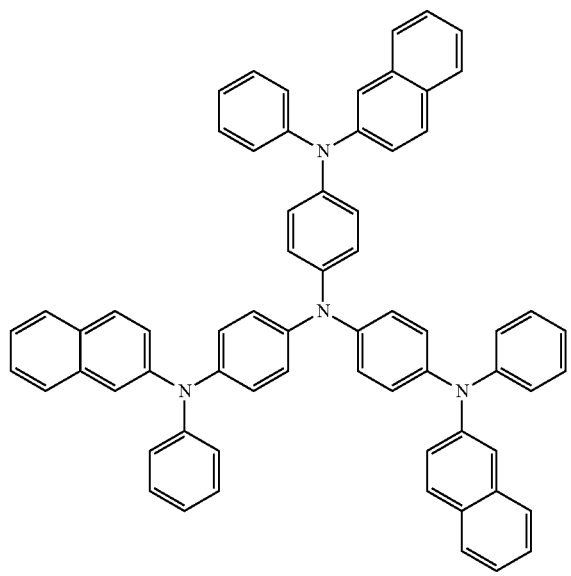

2-TNATA

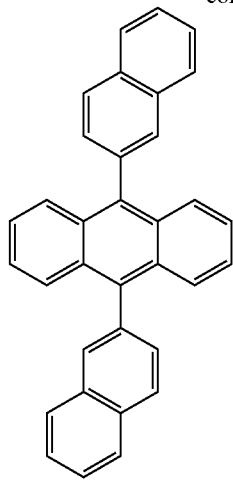

ADN

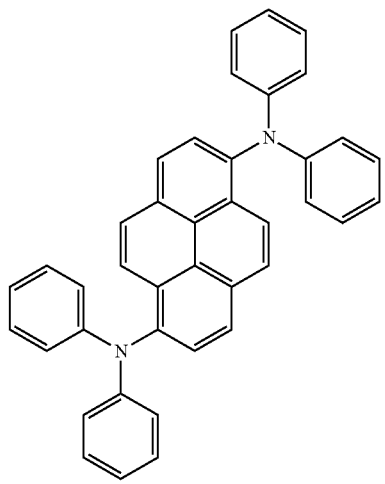

TPD

An organic light-emitting device was manufactured in the same manner as in Example 1, except that in forming the hole transport layer, Compound 21 was used instead of Compound 1.

Example 3

An organic light-emitting device was manufactured in the same manner as in Example 1, except that in forming the hole transport layer, Compound 29 was used instead of Compound 1.

Example 4

An organic light-emitting device was manufactured in the same manner as in Example 1, except that in forming the hole transport layer, Compound 40 was used instead of Compound 1.

Example 5

An organic light-emitting device was manufactured in the same manner as in Example 1, except that in forming the hole transport layer, Compound 49 was used instead of Compound 1.

Example 6

An organic light-emitting device was manufactured in the same manner as in Example 1, except that in forming the hole transport layer, Compound 56 was used instead of Compound 1.

Example 7

An organic light-emitting device was manufactured in the same manner as in Example 1, except that in forming the hole transport layer, Compound 57 was used instead of Compound 1.

Example 8

An organic light-emitting device was manufactured in the same manner as in Example 1, except that in forming the hole transport layer, Compound 59 was used instead of Compound 1.

Example 9

An organic light-emitting device was manufactured in the same manner as in Example 1, except that in forming the hole transport layer, Compound 62 was used instead of Compound 1.

Example 10

An organic light-emitting device was manufactured in the same manner as in Example 1, except that in forming the hole transport layer, Compound 63 was used instead of Compound 1.

Example 11

An organic light-emitting device was manufactured in the same manner as in Example 1, except that in forming the hole transport layer, Compound 70 was used instead of Compound 1.

Example 12

An organic light-emitting device was manufactured in the same manner as in Example 1, except that in forming the hole transport layer, Compound 74 was used instead of Compound 1.

Example 13

An organic light-emitting device was manufactured in the same manner as in Example 1, except that in forming the hole transport layer, Compound 78 was used instead of Compound 1.

Example 14

An organic light-emitting device was manufactured in the same manner as in Example 1, except that in forming the hole transport layer, Compound 85 was used instead of Compound 1.

Example 15

An organic light-emitting device was manufactured in the same manner as in Example 1, except that in forming the hole transport layer, Compound 89 was used instead of Compound 1.

Example 16

An organic light-emitting device was manufactured in the same manner as in Example 1, except that in forming the hole transport layer, Compound 90 was used instead of Compound 1.

Example 17

An organic light-emitting device was manufactured in the same manner as in Example 1, except that in forming the hole transport layer, Compound 98 was used instead of Compound 1.

Example 18

An organic light-emitting device was manufactured in the same manner as in Example 1, except that in forming the hole transport layer, Compound 102 was used instead of Compound 1.

Example 19

An organic light-emitting device was manufactured in the same manner as in Example 1, except that in forming the hole transport layer, Compound 106 was used instead of Compound 1.

Example 20

An organic light-emitting device was manufactured in the same manner as in Example 1, except that in forming the hole transport layer, Compound 110 was used instead of Compound 1.

Comparative Example 1

An organic light-emitting device was manufactured in the same manner as in Example 1, except that in forming the hole transport layer, NPB was used instead of Compound 1.

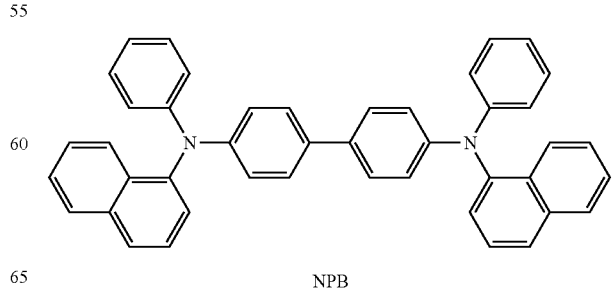

NPB

Comparative Example 2

An organic light-emitting device was manufactured in the same manner as in Example 1, except that in forming the hole transport layer, Compound A was used instead of Compound 1.

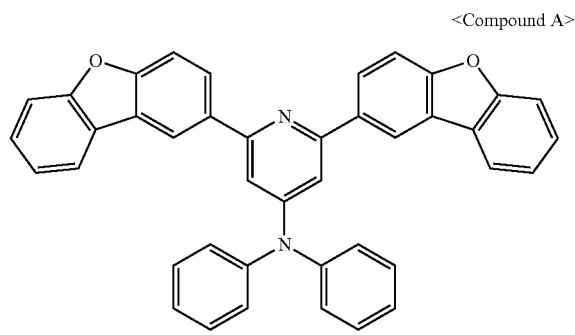 [SMILES: c1ccc(N(c2ccccc2)c2cc(-c3ccc4oc5ccccc5c4c3)nc(-c3ccc4oc5ccccc5c4c3)c2)cc1]

<Compound A>

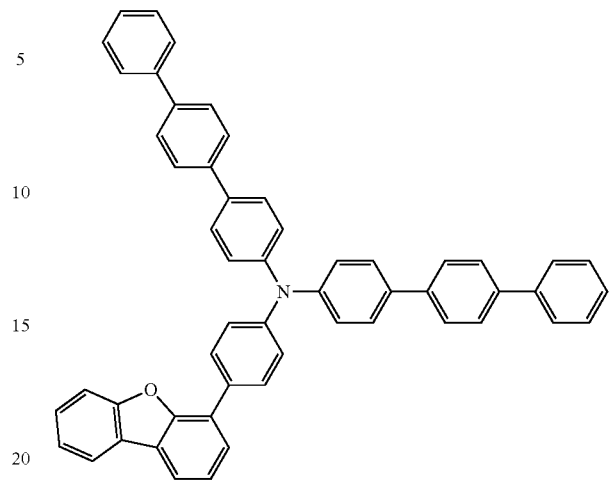

<Compound B>

Comparative Example 3

An organic light-emitting device was manufactured in the same manner as in Example 1, except that in forming the hole transport layer, Compound B was used instead of Compound 1.

Evaluation Example 1

The driving voltage, current density, brightness, efficiency, and half-lifespan of the organic light-emitting devices manufactured according to Examples 1 to 20, and Comparative Examples 1 to 3 were measured by using Kethley SMU 236 and a brightness photometer PR650, and results thereof are shown in Table 2. The half-lifespan is a period of time that taken until the brightness of the organic light-emitting device reaches 50% of initial brightness.

TABLE 2

| | Material for hole transport layer | Driving voltage (V) | Current Density (mA/cm$^2$) | Brightness (cd/m$^2$) | Efficiency (cd/A) | Emission color | Half lifespan (hr @ 100 mA/cm$^2$) |
|---|---|---|---|---|---|---|---|
| Example 1 | Compound 1 | 5.68 | 50 | 3080 | 6.16 | Blue | 305 |
| Example 2 | Compound 21 | 5.65 | 50 | 3085 | 6.17 | Blue | 308 |
| Example 3 | Compound 29 | 5.70 | 50 | 3082 | 6.16 | Blue | 312 |
| Example 4 | Compound 40 | 5.65 | 50 | 3095 | 6.19 | Blue | 300 |
| Example 5 | Compound 49 | 5.64 | 50 | 3110 | 6.42 | Blue | 315 |
| Example 6 | Compound 56 | 5.42 | 50 | 3190 | 6.22 | Blue | 325 |
| Example 7 | Compound 57 | 5.43 | 50 | 3220 | 6.44 | Blue | 329 |
| Example 8 | Compound 59 | 5.40 | 50 | 3250 | 6.50 | Blue | 340 |
| Example 9 | Compound 62 | 5.42 | 50 | 3330 | 6.66 | Blue | 355 |
| Example 10 | Compound 63 | 5.50 | 50 | 3280 | 6.56 | Blue | 335 |
| Example 11 | Compound 70 | 5.50 | 50 | 3220 | 6.44 | Blue | 370 |
| Example 12 | Compound 74 | 5.45 | 50 | 3215 | 6.43 | Blue | 340 |
| Example 13 | Compound 78 | 5.51 | 50 | 3220 | 6.44 | Blue | 325 |
| Example 14 | Compound 85 | 5.53 | 50 | 3218 | 6.43 | Blue | 330 |
| Example 15 | Compound 89 | 5.53 | 50 | 3220 | 6.44 | Blue | 335 |
| Example 16 | Compound 90 | 5.51 | 50 | 3215 | 6.43 | Blue | 350 |
| Example 17 | Compound 98 | 5.60 | 50 | 3200 | 6.40 | Blue | 338 |
| Example 18 | Compound 102 | 5.55 | 50 | 3290 | 6.58 | Blue | 330 |
| Example 19 | Compound 106 | 5.60 | 50 | 3210 | 6.42 | Blue | 325 |
| Example 20 | Compound 110 | 5.57 | 50 | 3200 | 6.40 | Blue | 340 |
| Comparative Example 1 | NPB | 7.01 | 50 | 2645 | 5.29 | Blue | 258 |
| Comparative Example 2 | Compound A | 8.99 | 50 | 2842 | 5.68 | Blue | 225 |
| Comparative Example 3 | Compound B | 7.66 | 50 | 2925 | 5.85 | Blue | 248 |

From Table 2, it may be that the organic light-emitting devices manufactured according to Examples 1 to 20 exhibited lower driving voltage, higher brightness, higher efficiency, and longer half-lifespan than the organic light-emitting devices manufactured according to Comparative Examples 1 to 3.

As described above, according to the one or more of the above exemplary embodiments, an organic light-emitting device including the amine-based compound may have a low driving voltage, high efficiency, high brightness, and long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An amine-based compound represented by Formula 1:

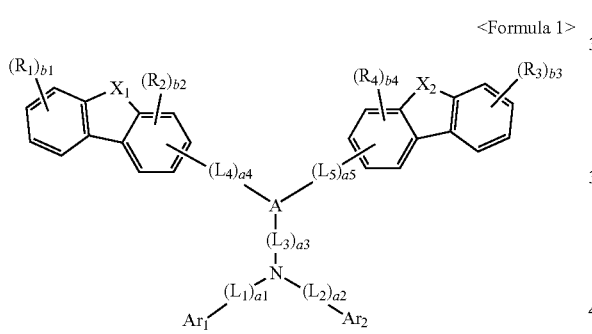

<Formula 1> wherein, in Formula 1, $X_1$ and $X_2$ are each independently O or S;

A is a substituted or unsubstituted $C_6$-$C_{20}$ aromatic ring;

$L_1$, $L_2$, $L_4$, and $L_5$ are each independently selected from the group consisting of a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

$L_3$ is a group represented by one of the following Formulae 3-2 to 3-33:

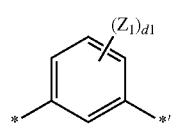

Formula 3-2

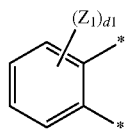

Formula 3-3

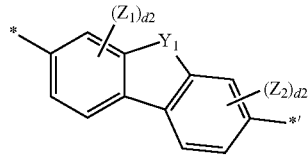

Formula 3-4

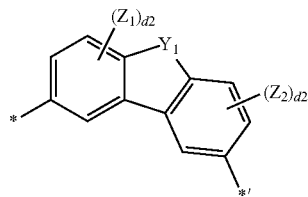

Formula 3-5

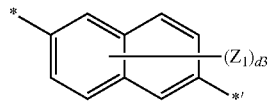

Formula 3-6

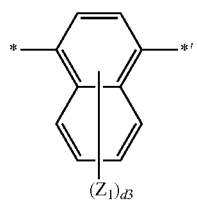

Formula 3-7

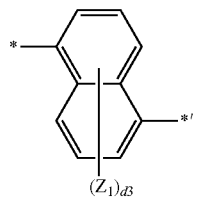

Formula 3-8

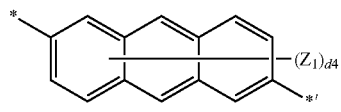

Formula 3-9

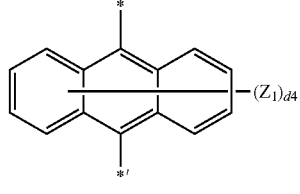

Formula 3-10

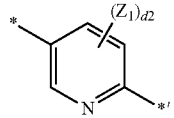

Formula 3-11

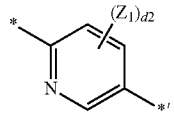

Formula 3-12

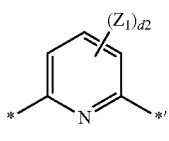
Formula 3-1
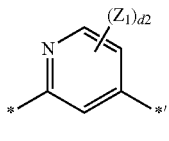
Formula 3-2
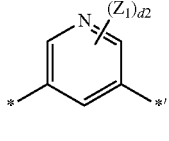
Formula 3-3
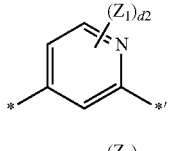
Formula 3-4
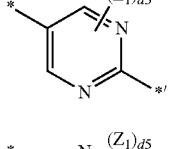
Formula 3-5
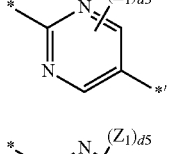
Formula 3-6
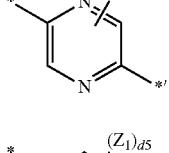
Formula 3-7
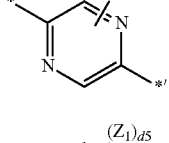
Formula 3-8
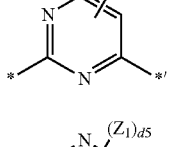
Formula 3-9
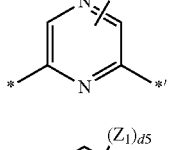
Formula 3-10
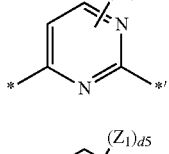
Formula 3-11
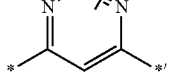
Formula 3-12
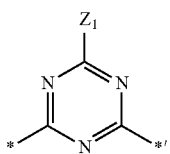
Formula 3-13
Formula 3-14
Formula 3-15
Formula 3-16
Formula 3-17
Formula 3-18
Formula 3-19
Formula 3-20
Formula 3-21
Formula 3-22
Formula 3-23
Formula 3-24
Formula 3-25
Formula 3-26
Formula 3-27
Formula 3-28
Formula 3-29
Formula 3-30
Formula 3-31
Formula 3-32
Formula 3-33 wherein, in Formulae 3-2 to 3-33, $Y_1$ is O, S, $C(Z_3)(Z_4)$, $N(Z_5)$, or $Si(Z_6)(Z_7)$;

$Z_1$ to $Z_7$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$ to $C_{20}$ alkyl group, a $C_1$ to $C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 is an integer of 1 to 4, d2 is an integer of 1 to 3, d3 is an integer of 1 to 6, d4 is an integer of 1 to 8, d5 is 1 or 2, d6 is an integer of 1 to 5, and each of * and *' indicates a binding site to a neighboring atom;

a1 to a5 are each independently selected from the group consisting of 0, 1, 2 and 3, when a1 is 2 or more, a plurality of $L_1$ are identical or different, when a2 is 2 or more, a plurality of $L_2$ are identical or different, when a3 is 2 or more, a plurality of $L_3$ are identical or different, when a4 is 2 or more, a plurality of $L_4$ are identical or different, and when a5 is 2 or more, a plurality of $L_5$ are identical or different;

$Ar_1$ and $Ar_2$ are each independently selected from the group consisting of a phenyl group, a pentalenyl group, an indenyl group, a naphthyl group, an azulenyl group, a heptalenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, an imidazopyrimidinyl group, each substituted with at least one selected from the group consisting of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, an imidazopyrimidinyl group, or —Si($Q_{31}$)($Q_{32}$)($Q_{33}$); in which $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_1$ to $R_4$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic heterocondensed polycyclic group, —Si$(Q_1)(Q_2)(Q_3)$, and —B$(Q_4)(Q_5)$;

b1 and b3 are each independently selected from the group consisting of 1, 2, 3 and 4, and b2 and b4 are each independently selected from the group consisting of 1, 2 and 3, when b1 is 2 or more, a plurality of $R_1$ are identical or different, when b2 is 2 or more, a plurality of $R_2$ are identical or different, when b3 is 2 or more, a plurality of $R_3$ are identical or different, and when b4 is 2 or more, a plurality of $R_4$ are identical or different;

at least one substituent of the substituted $C_6$-$C_{20}$ aromatic ring, substituted $C_3$-$C_{20}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from the group consisting of:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from the group consisting of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{11})(Q_{12})(Q_{13})$, and —B$(Q_{14})(Q_{15})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from the group consisting of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —Si$(Q_{21})(Q_{22})(Q_{23})$, and —B$(Q_{24})(Q_{25})$; and —Si$(Q_{31})(Q_{32})(Q_{33})$ and —B$(Q_{34})(Q_{35})$, in which $Q_1$ to $Q_5$, $Q_{11}$ to $Q_{15}$, $Q_{21}$ to $Q_{25}$, and $Q_{31}$ to $Q_{35}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The amine-based compound as claimed in claim 1, wherein A is selected from a substituted or unsubstituted benzene, a substituted or unsubstituted naphthalene, a substituted or unsubstituted anthracene, a substituted or unsubstituted pyrene, a substituted or unsubstituted phenanthrene, a substituted or unsubstituted chrysene, and a substituted or unsubstituted triphenylene.

3. The amine-based compound as claimed in claim 1, wherein A is a group represented by one of the following Formulae 2-1 to 2-19:

Formula 2-1
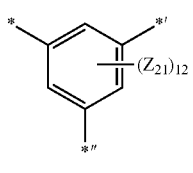
Formula 2-2
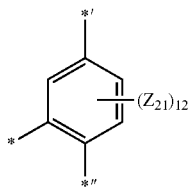
Formula 2-3
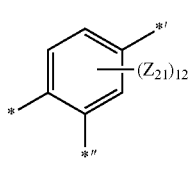
Formula 2-4
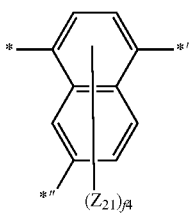
Formula 2-5
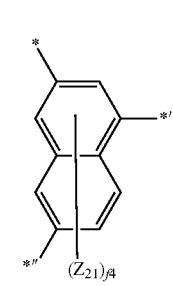
Formula 2-6
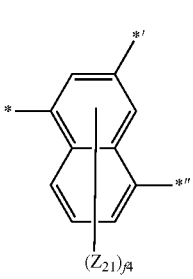
Formula 2-7
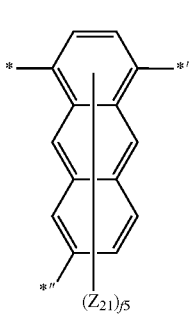
-continued
Formula 2-8
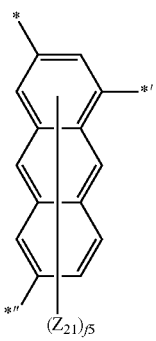
Formula 2-9
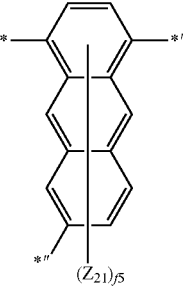
Formula 2-10
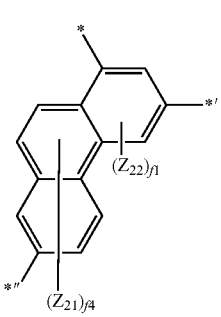
Formula 2-11
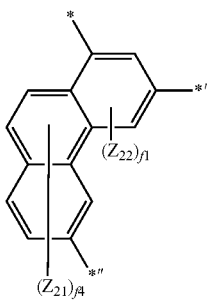
Formula 2-12
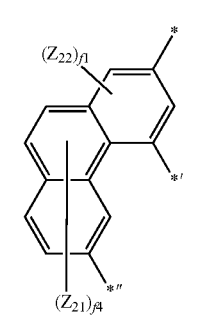

-continued

Formula 2-13

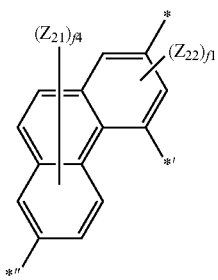

Formula 2-14

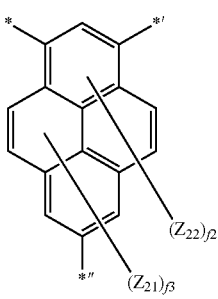

Formula 2-15

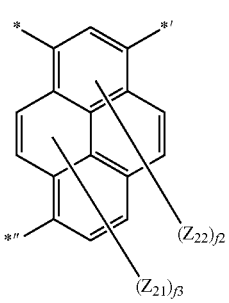

Formula 2-16

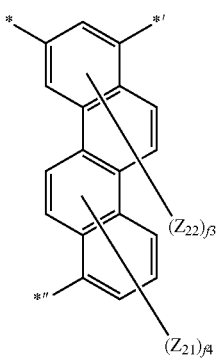

Formula 2-17

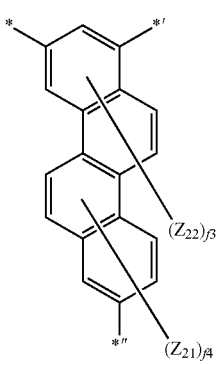

-continued

Formula 2-18

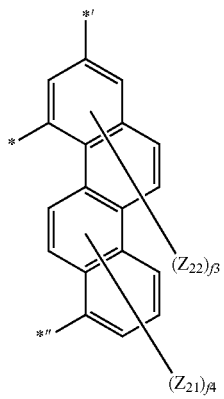

Formula 2-19

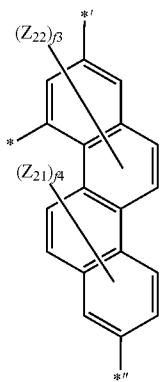

wherein, in Formulae 2-1 to 2-19, $Z_{21}$ and $Z_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$ to $C_{20}$ alkyl group, a $C_1$ to $C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

f1 is 1 or 2, f2 is an integer of 1 to 3, f3 is an integer of 1 to 4, f4 is an integer of 1 to 5, and f5 is an integer of 1 to 7; and each of * and *' is a binding site to a neighboring atom, and *" is a binding site to $L_3$ in -$(L_3)_{a3}$- or N.

4. The amine-based compound as claimed in claim 1, wherein:

a1, a2, a4, and a5 are each independently 0 or 1.

5. The amine-based compound as claimed in claim 1, wherein $Ar_1$ and $Ar_2$ are each independently a group represented by one of the following Formulae 5-1 to 5-3 and 5-6 to 5-13:

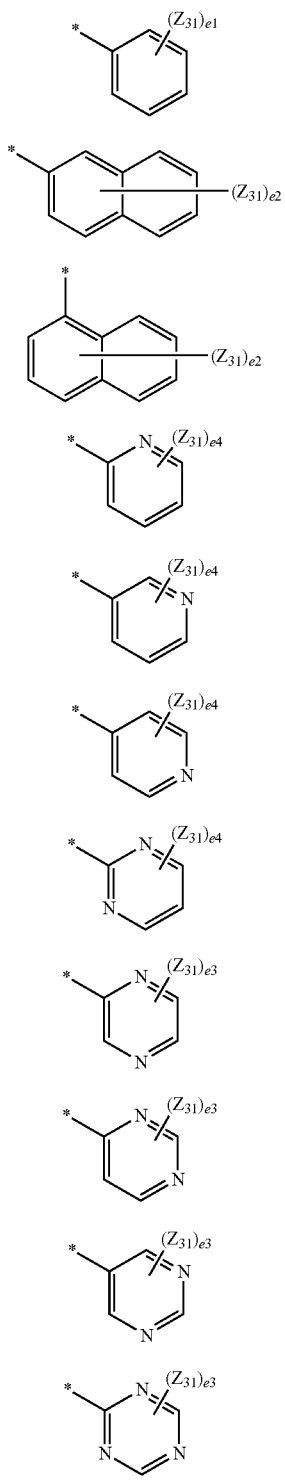

Formula 5-1
Formula 5-2
Formula 5-3
Formula 5-6
Formula 5-7
Formula 5-8
Formula 5-9
Formula 5-10
Formula 5-11
Formula 5-12
Formula 5-13 wherein, in Formulae 5-1 to 5-3 and 5-6 to 5-13,
$Z_{31}$ is selected from:
a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group;

a phenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group and a naphthyl group; and $Si(Q_{31})(Q_{32})(Q_{33})$, in which $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$ to $C_{20}$ alkyl group, a $C_1$ to $C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and e1 is an integer of 1 to 5; e2 is an integer of 1 to 7; e3 is an integer of 1 to 3; e4 is an integer of 1 to 4; e5 is 1 or 2; and * indicates a binding site to a neighboring atom.

6. The amine-based compound as claimed in claim 1, wherein $Ar_1$ and $Ar_2$ are each independently a group represented by one of the following Formulae 6-1 to 6-10 and 6-13 to 6-20:

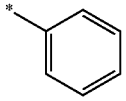

Formula 6-1

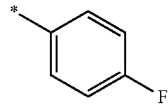

Formula 6-2

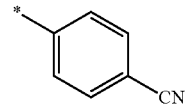

Formula 6-3

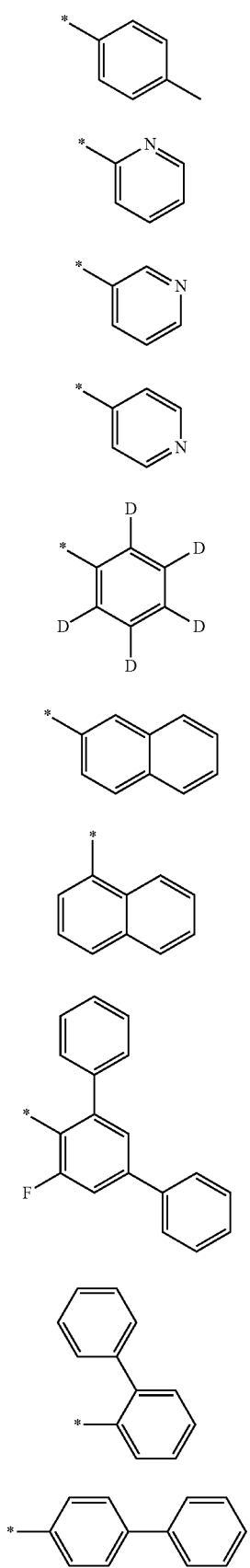
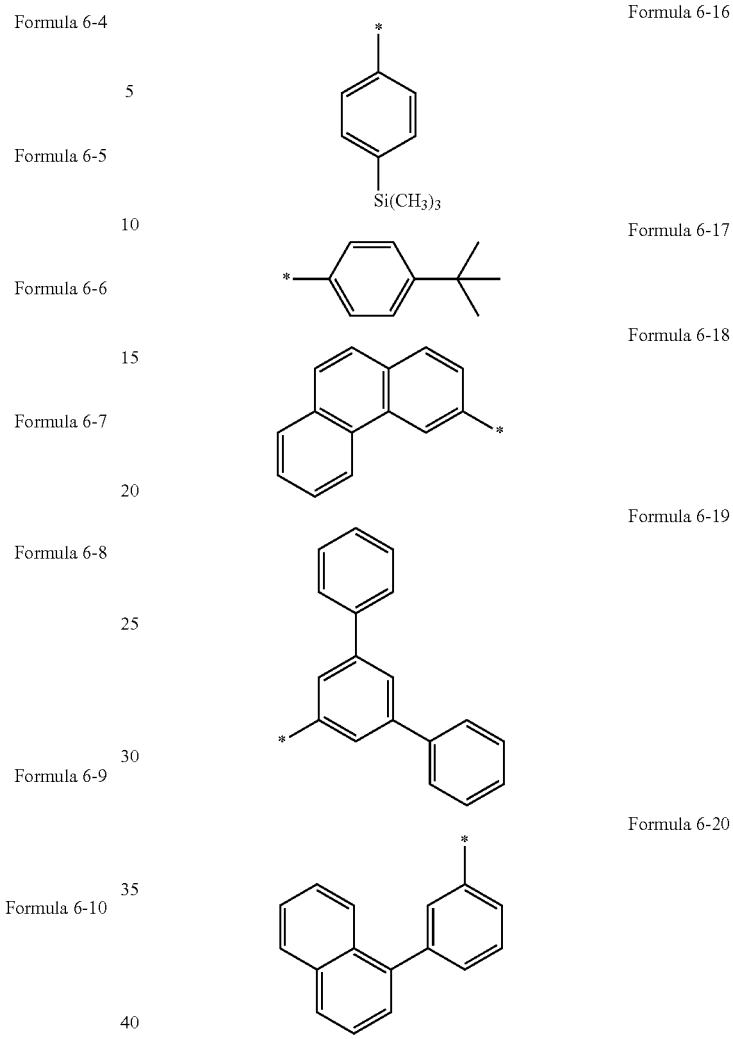

wherein, in Formulae 6-1 to 6-10 and 6-13 to 6-20, * indicates a binding site to a neighboring atom.

7. The amine-based compound as claimed in claim 1, wherein $R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, and —Si(Q$_1$)(Q$_2$)(Q$_3$).

8. The amine-based compound as claimed in claim 1, wherein $R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group and a substituted or unsubstituted $C_1$-$C_{20}$ alkoxy group.

9. The amine-based compound as claimed in claim 1, wherein the amine-based compound represented by Formula 1 is represented by one of the following Formulae 1A to 1F:

<Formula 1A>

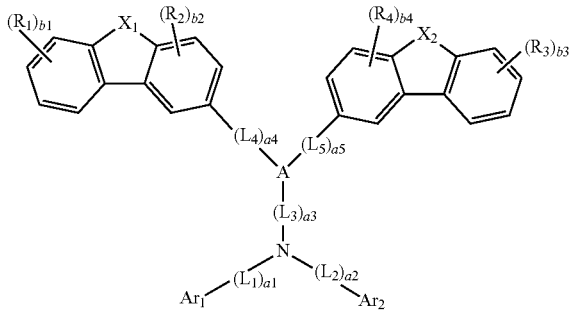

<Formula 1B>

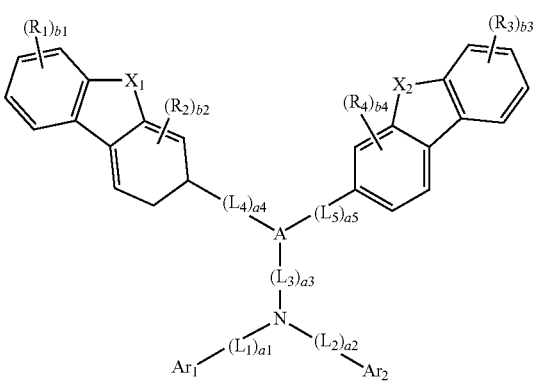

<Formula 1C>

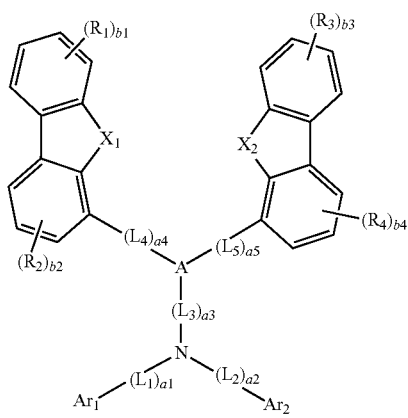

<Formula 1D>

<Formula 1E>

<Formula 1F>

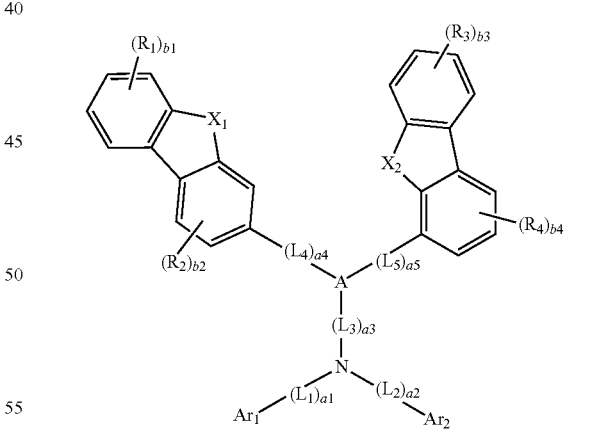

wherein $X_1$, $X_2$, A, $L_1$ to $L_5$, a1 to a5, $Ar_1$, $Ar_2$, $R_1$ to $R_4$ and b1 to b4 of Formulae 1A to 1F are defined the same as $X_1$, $X_2$, A, $L_1$ to $L_5$, a1 to a5, $Ar_1$, $Ar_2$, $R_1$ to $R_4$ and b1 to b4 of Formula 1.

10. The amine-based compound as claimed in claim 1, wherein the amine-based compound represented by Formula 1 is represented by one of the following Formulae 1A(1) to 1A(3), 1B(1) to 1B(3), 1C(1) to 1C(3), 1D(1) to 1D(3), 1E(1) to 1E(3) and 1F(1) to 1F(3):

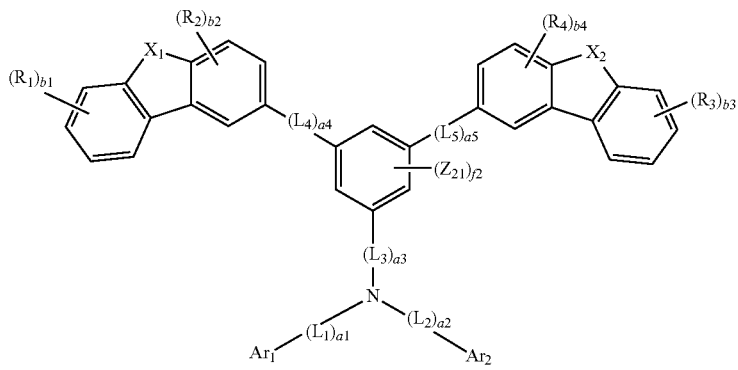
<Formula 1A(1)>
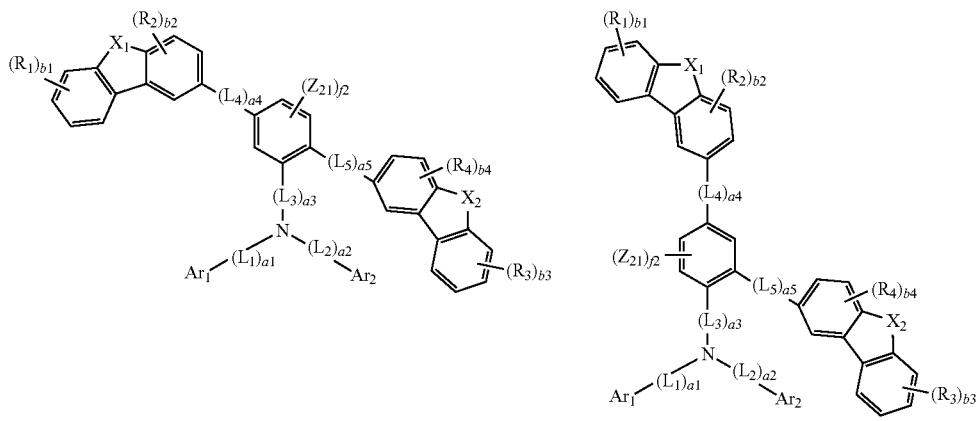
<Formula 1A(2)>
<Formula 1A(3)>
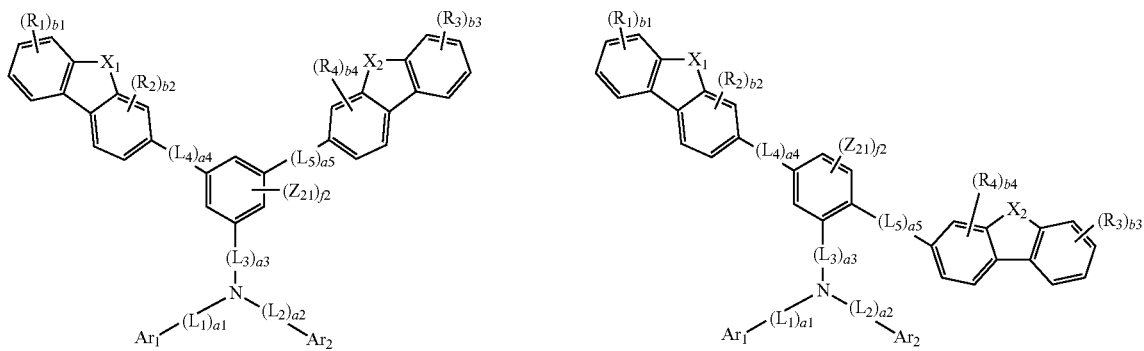
<Formula 1B(1)>
<Formula 1B(2)>

<Formula 1B(3)>
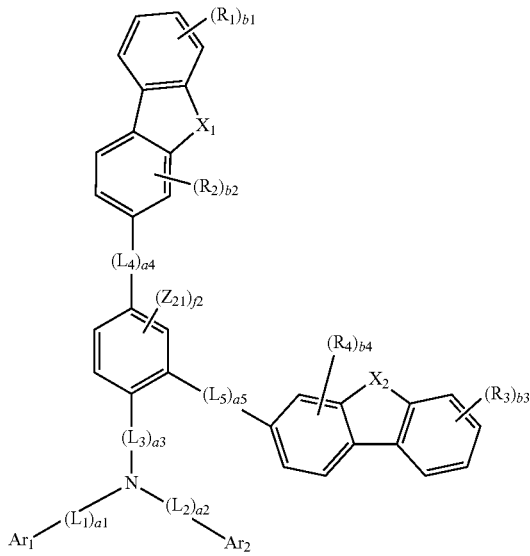
<Formula 1C(1)>
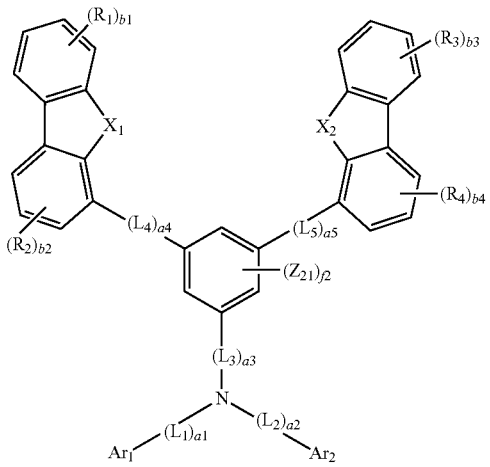
<Formula 1C(2)>
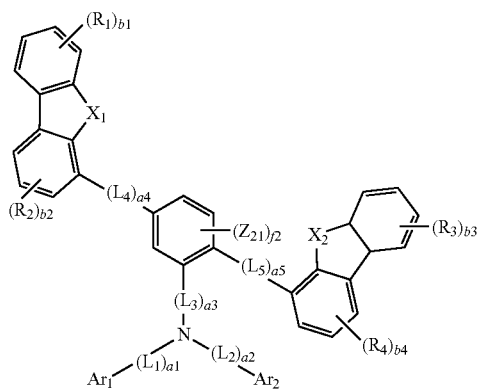
<Formula 1C(3)>
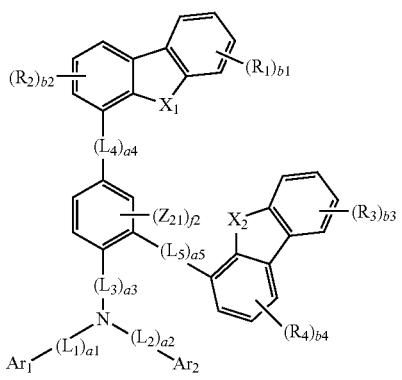
<Formula 1D(1)>
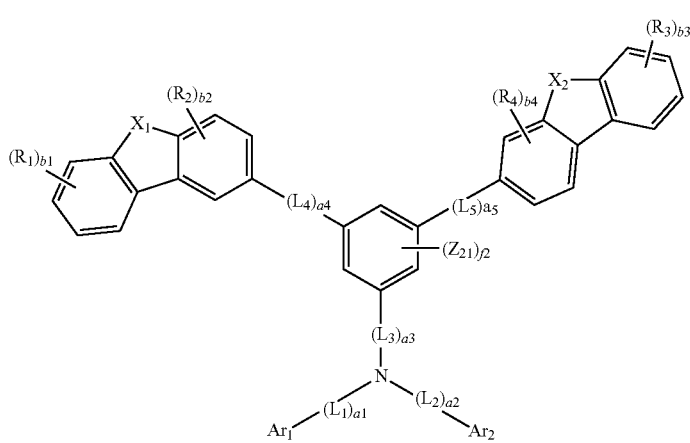

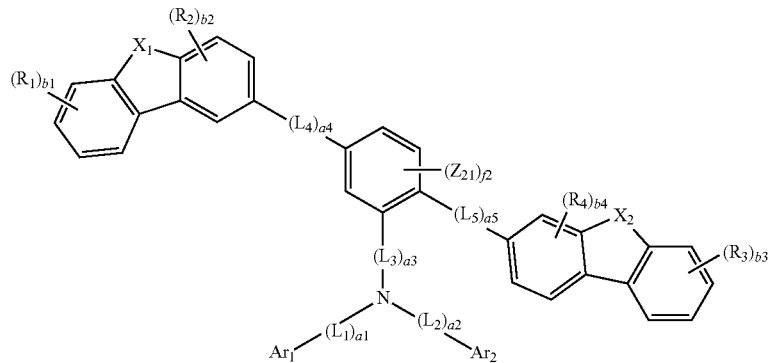
<Formula 1D(2)>
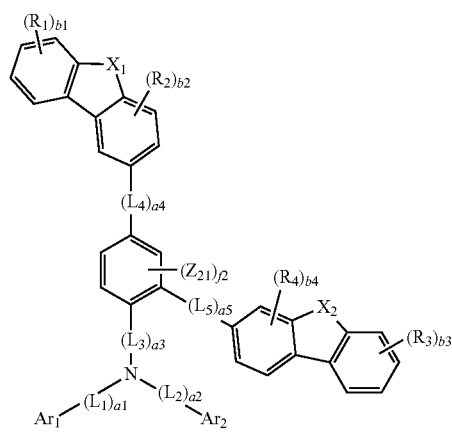
<Formula 1D(3)>
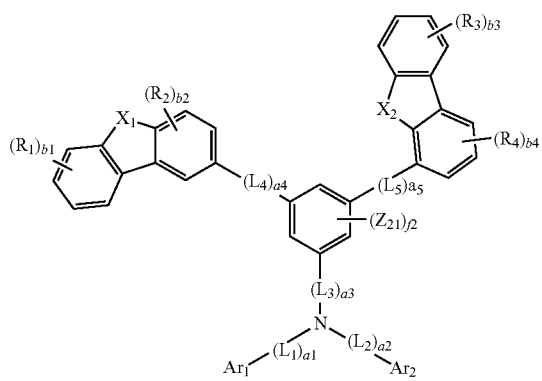
<Formula 1E(1)>
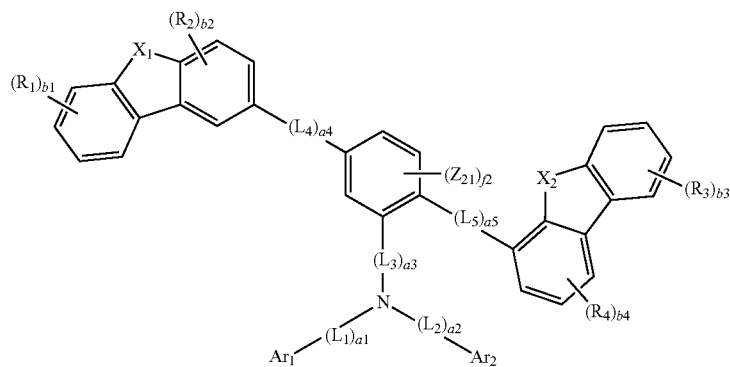
<Formula 1E(2)>

<Formula 1E(3)>
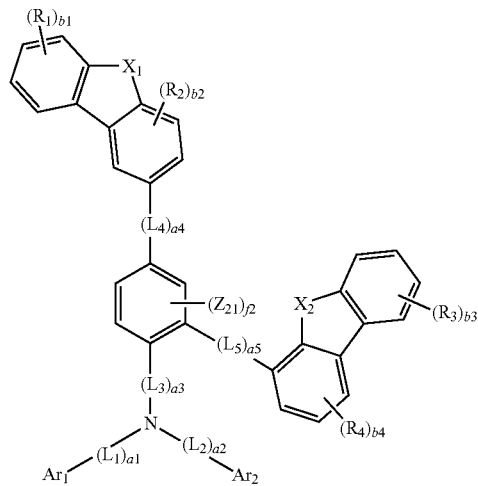
<Formula 1F(1)>
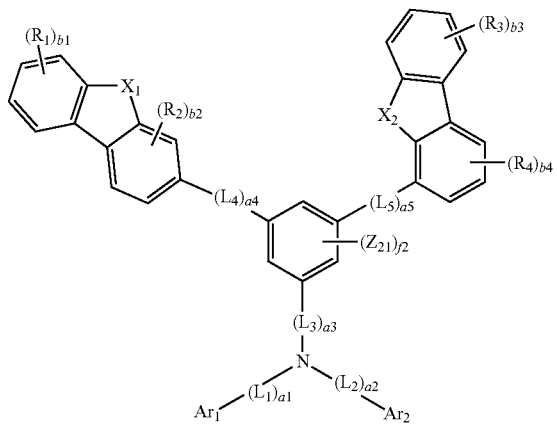
<Formula 1F(2)>
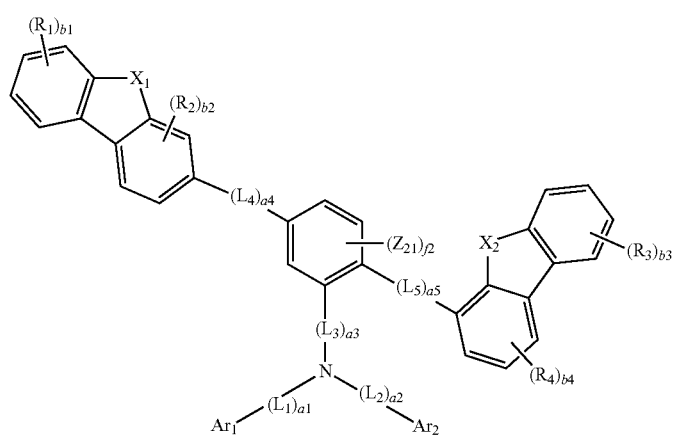
<Formula 1F(3)>
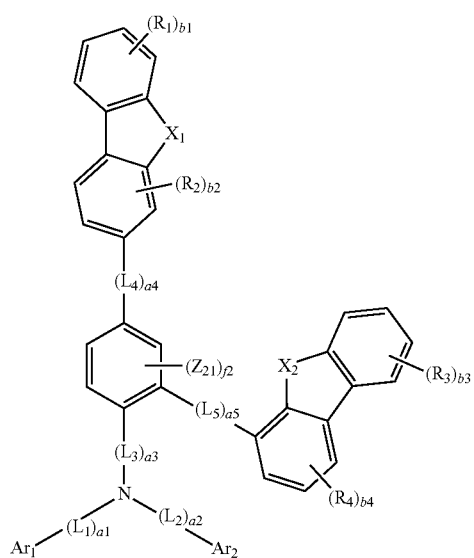

wherein $X_1$, $X_2$, $L_1$ to $L_5$, a1 to a5, $Ar_1$, $Ar_2$, $R_1$ to $R_4$ and b1 to b4 of Formulae 1A(1) to 1A(3), 1B(1) to 1B(3), 1C(1) to 1C(3), 1D(1) to 1D(3), 1E(1) to 1E(3) and 1F(1) to 1F(3) are defined the same as $X_1$, $X_2$, $L_1$ to $L_5$, a1 to a5, $Ar_1$, $Ar_2$, $R_1$ to $R_4$ and b1 to b4 of Formula 1;

$Z_{21}$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group; and f2 is an integer of 1 to 3.

11. The amine-based compound as claimed in claim 10, wherein:

a1, a2, a4, and a5 are each independently 0 or 1, $Ar_1$ and $Ar_2$ are each independently selected from:

a phenyl group, a naphthyl group, a phenanthrenyl group, an anthracenyl group, a pyrenyl group and a chrysenyl group; and a phenyl group, a naphthyl group, a phenanthrenyl group, an anthracenyl group, a pyrenyl group and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a phenanthrenyl group, an anthracenyl group, a pyrenyl group, a chrysenyl group and —Si($Q_{31}$)($Q_{32}$)($Q_{33}$), in which $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group and a chrysenyl group.

12. The amine-based compound as claimed in claim 1, wherein the amine-based compound represented by Formula 1 is one of the following Compounds 1 to 6, 13 to 18, 25 to 44, 49 to 54, 61 to 66, 73 to 92, 97 to 102, 109 to 126, and 133 to 140:

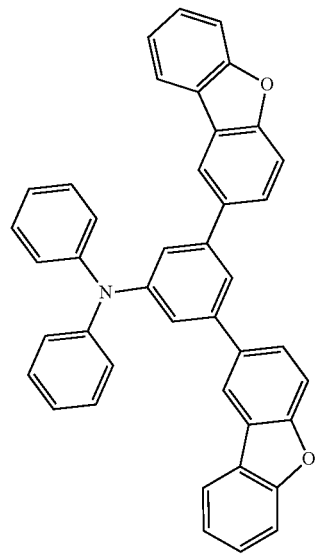

1

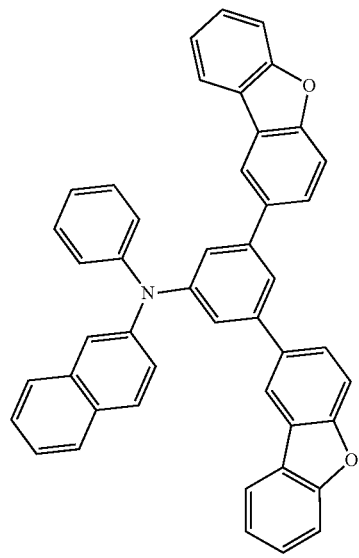

2

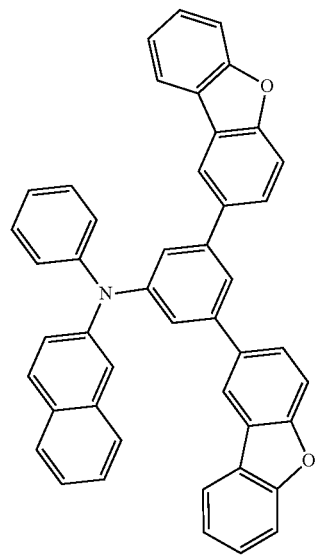

3

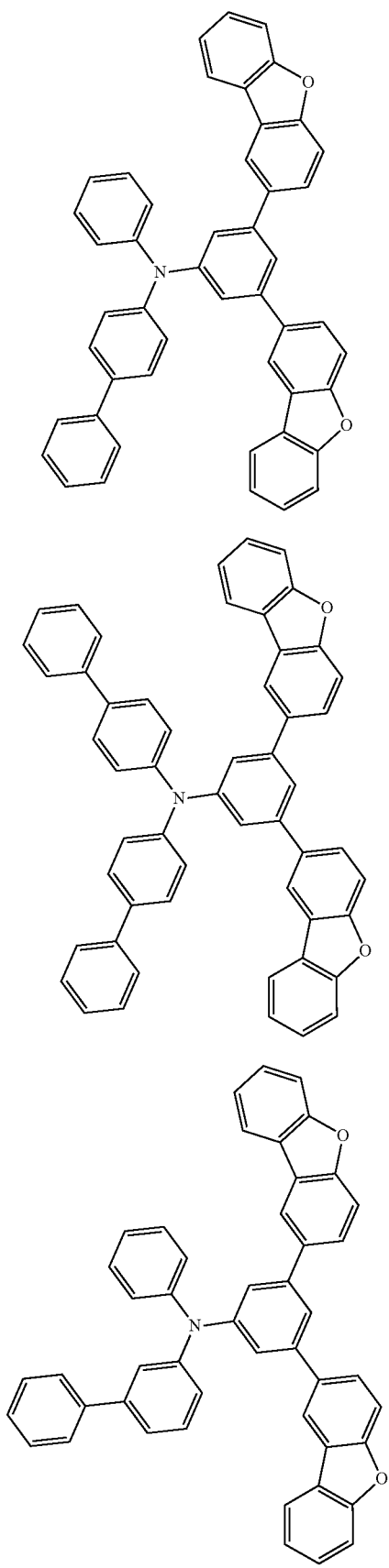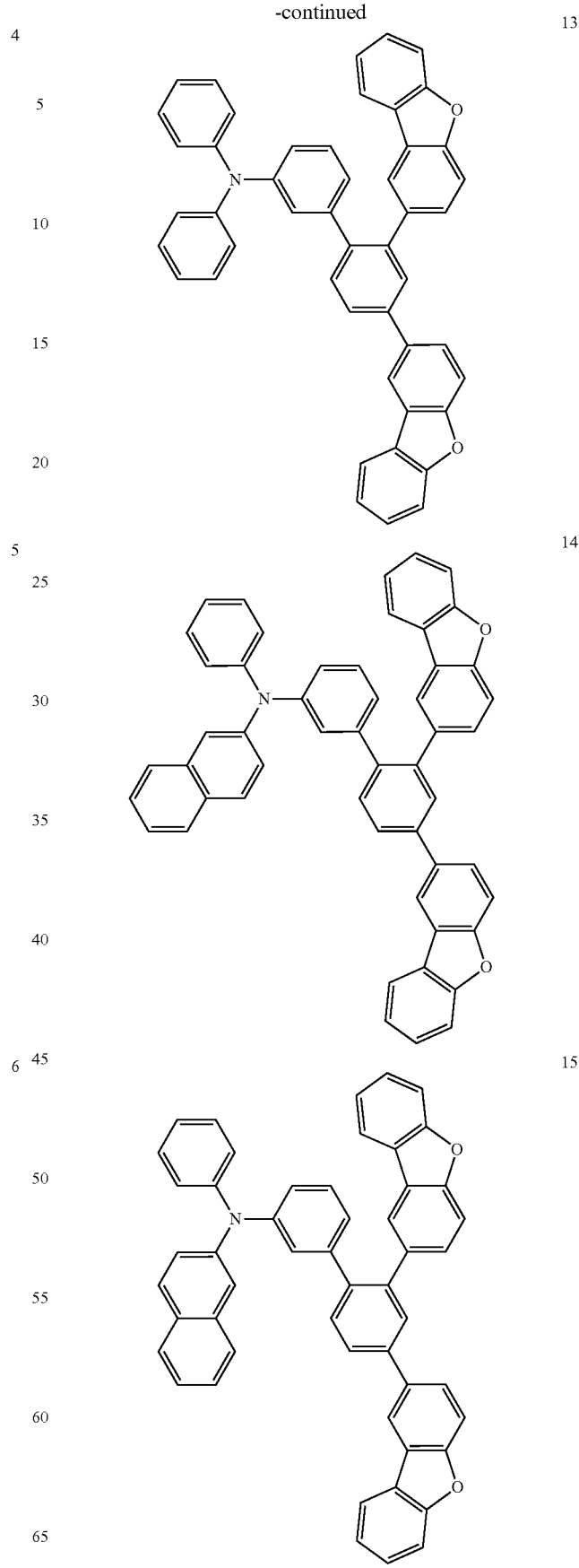

-continued
16
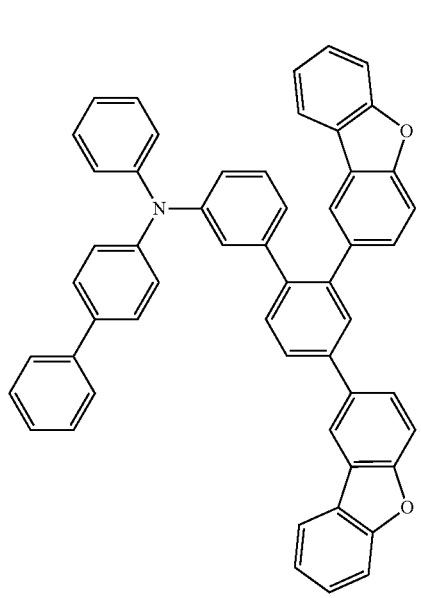
18
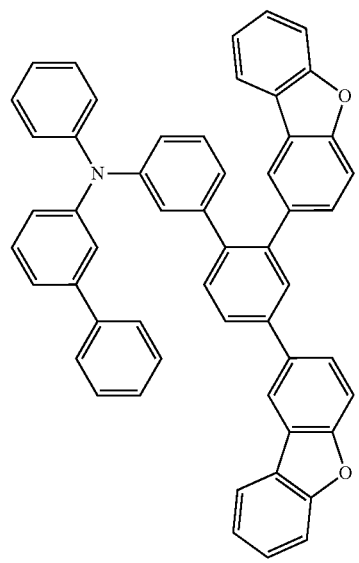
17
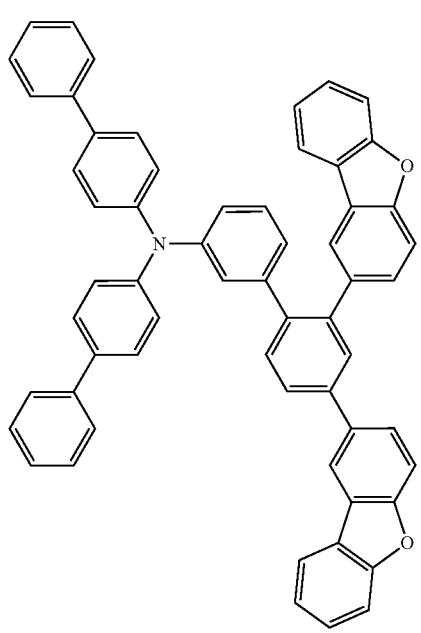
25
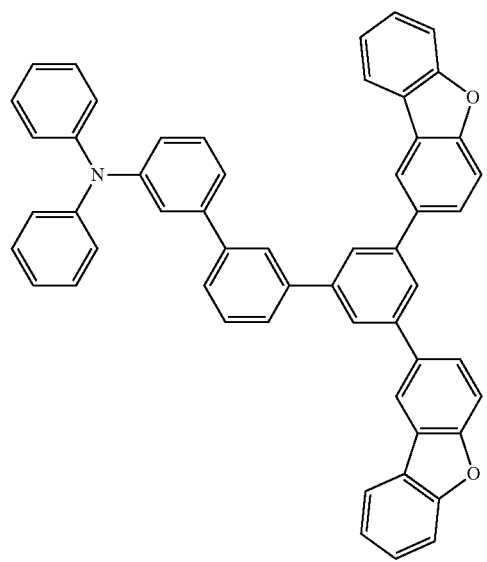

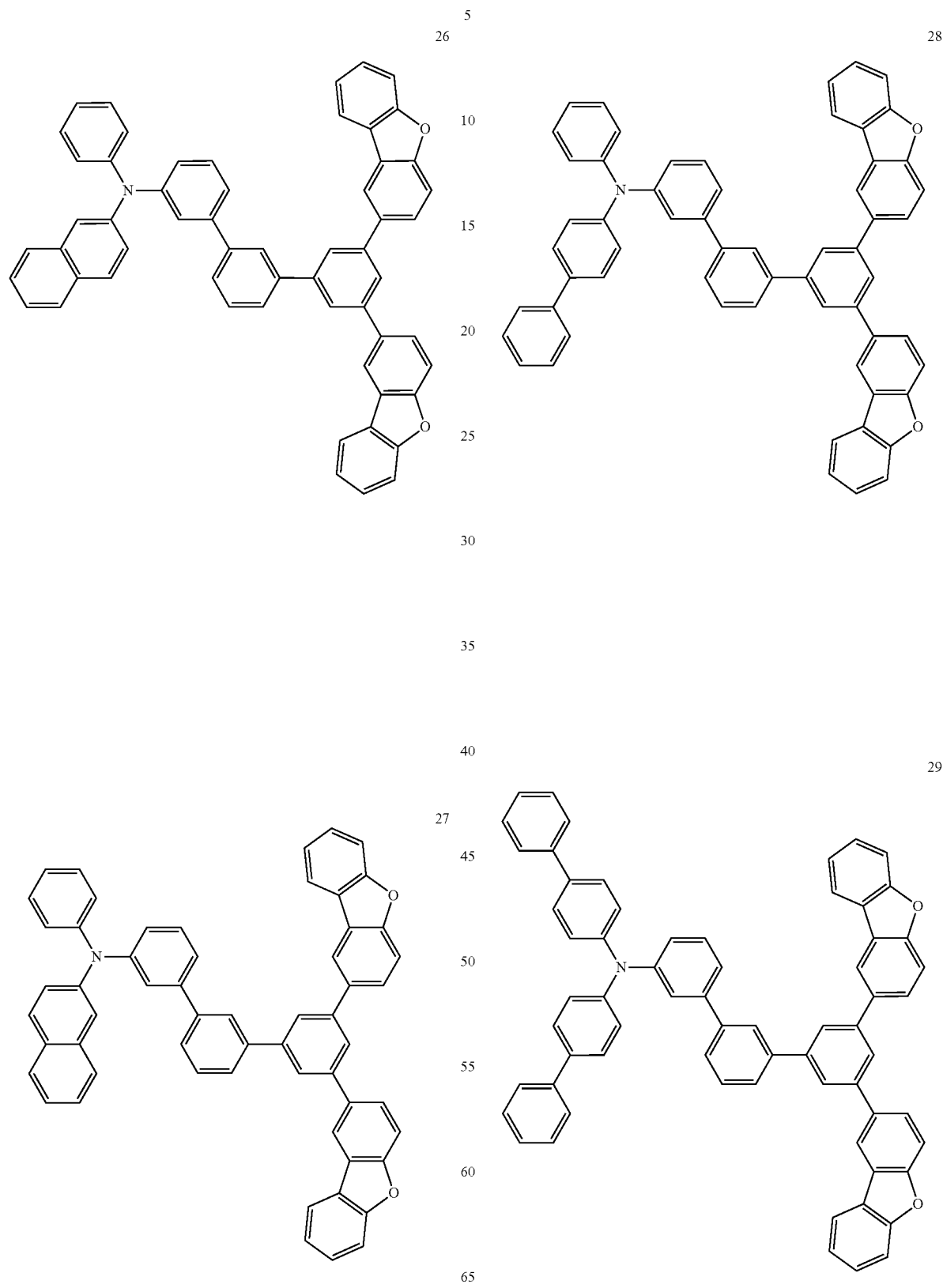

30
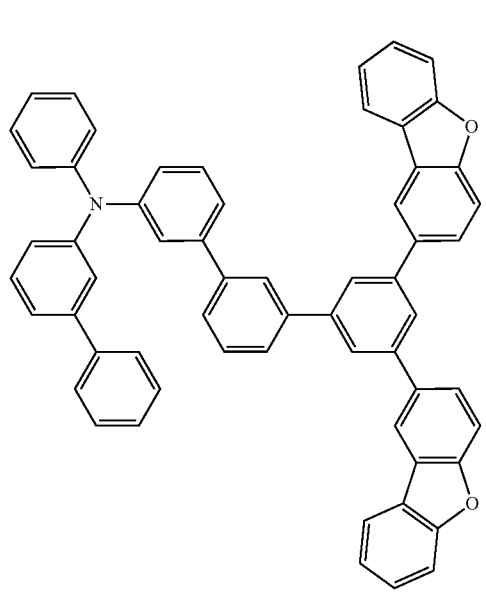
31
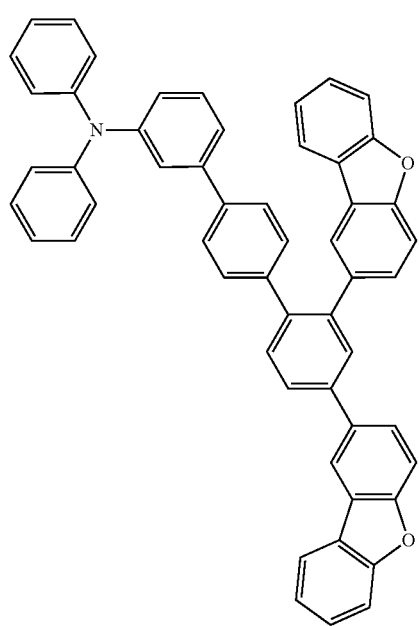
32
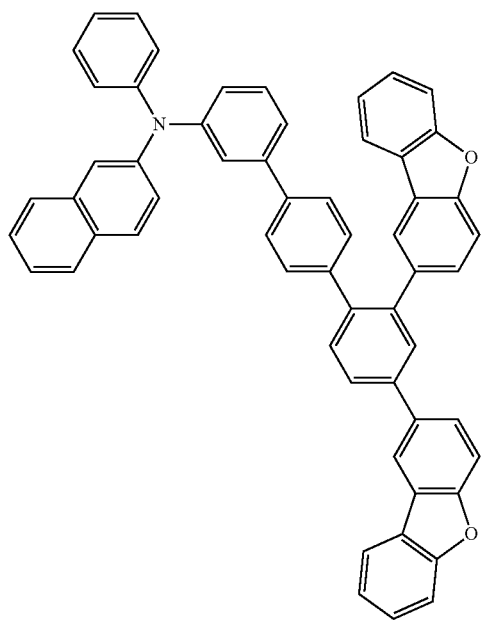
33
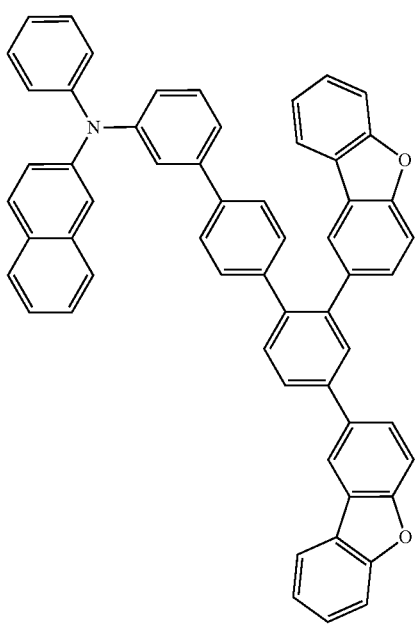

191
-continued
34
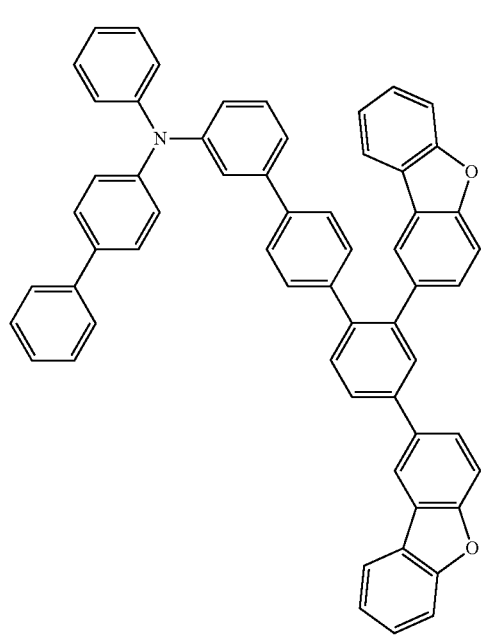
35
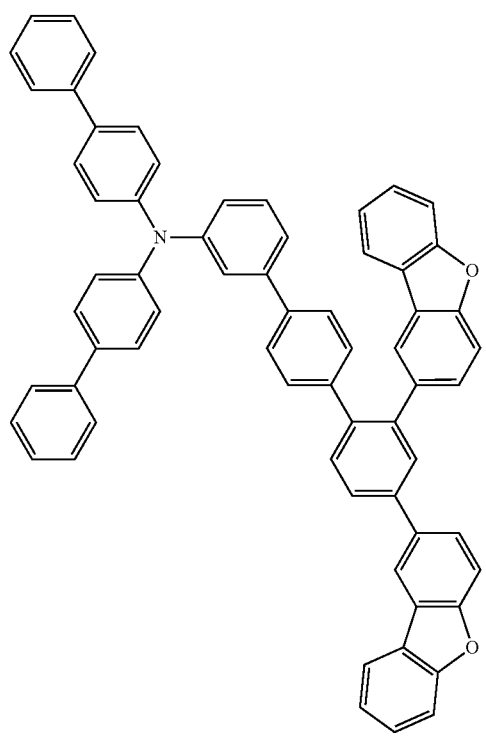
192
-continued
36
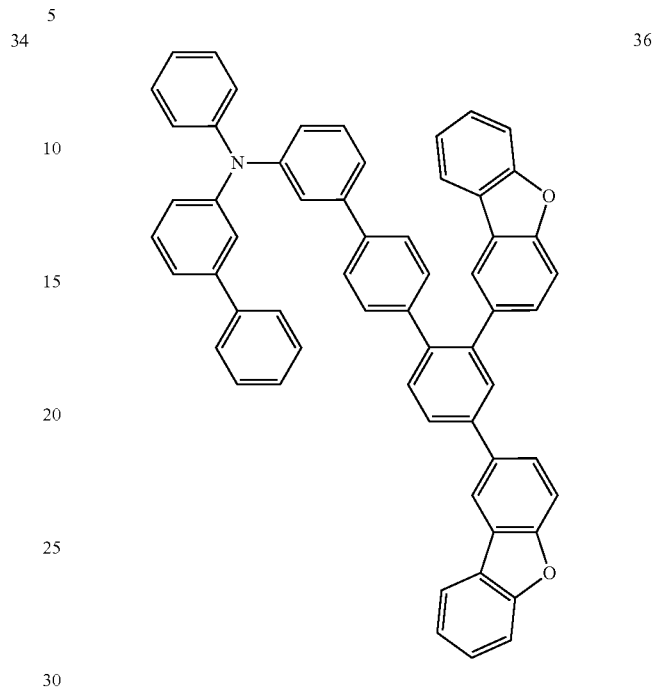
37
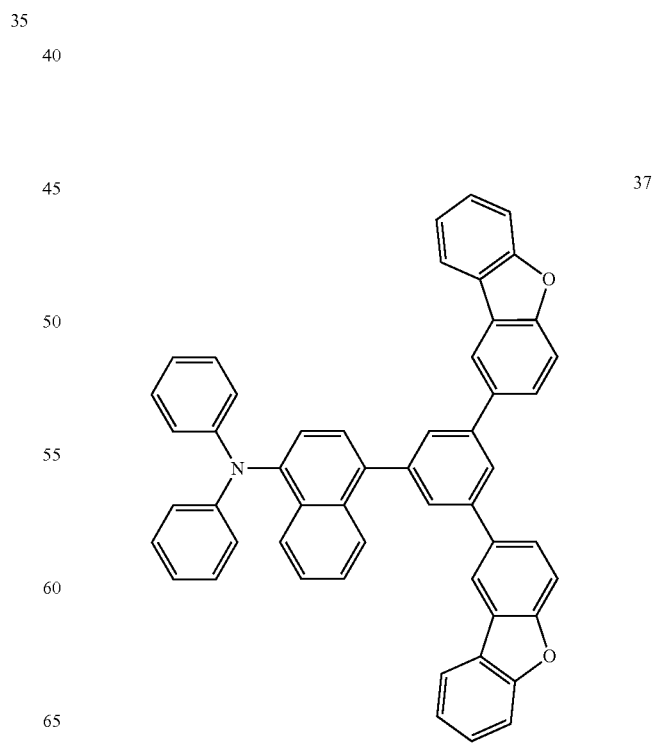

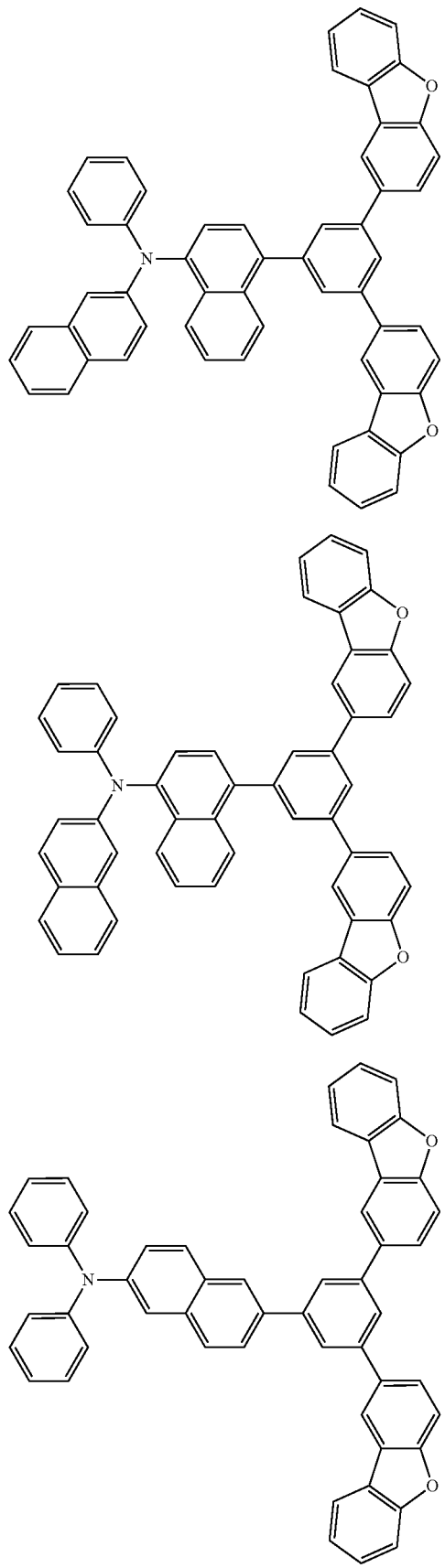
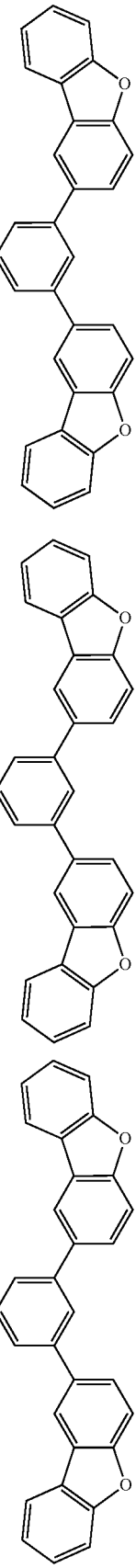

-continued

197
-continued
62
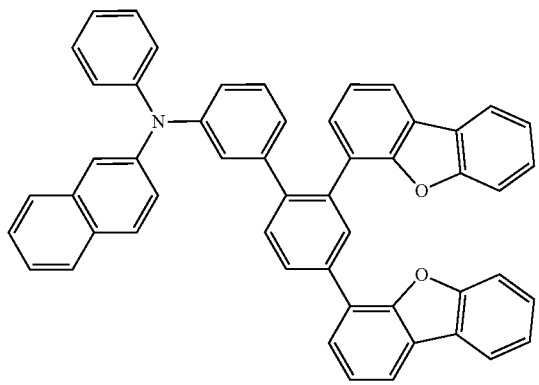
63
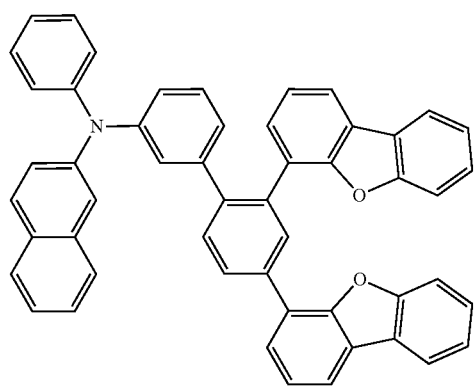
64
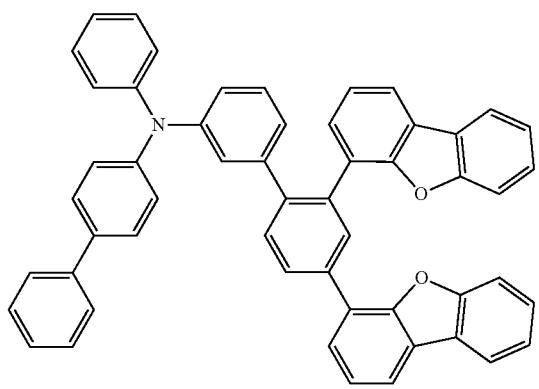
198
-continued
65
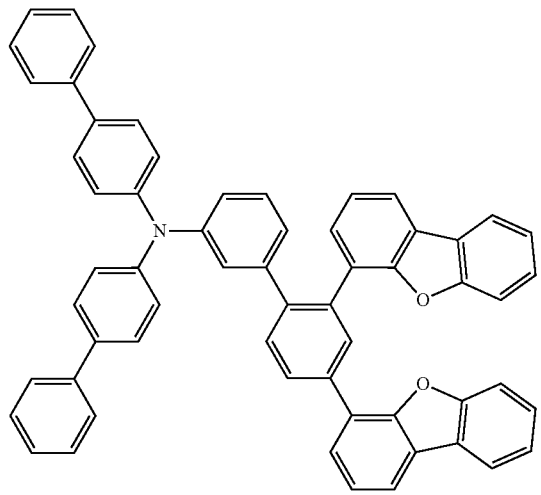
66
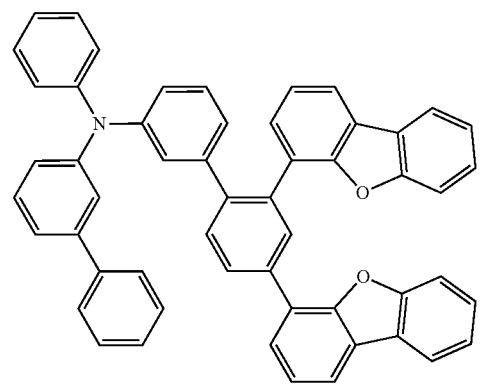
73
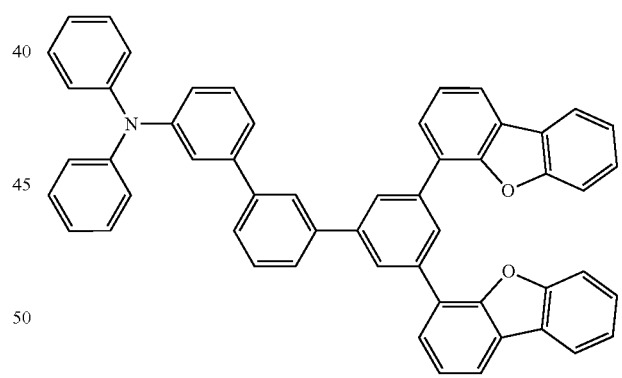
74
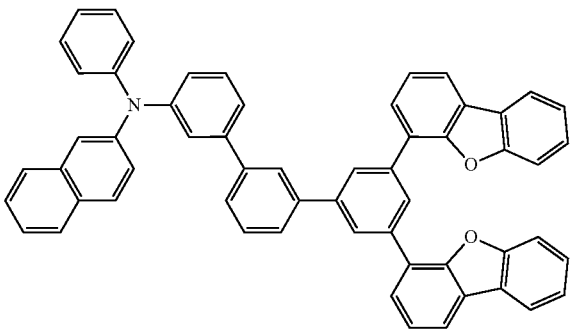

75
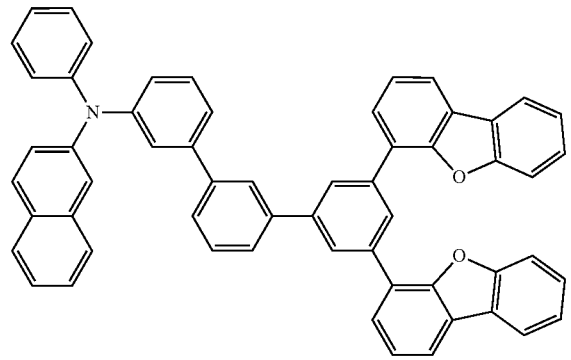
76
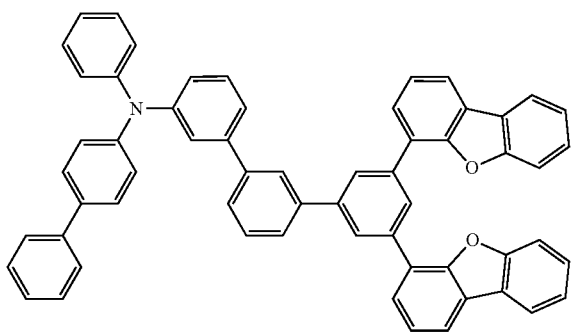
77
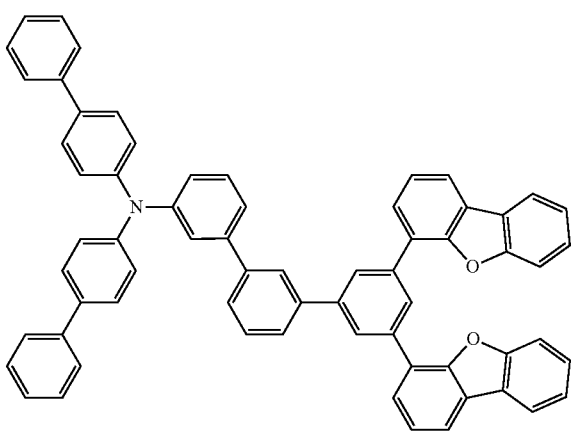
78
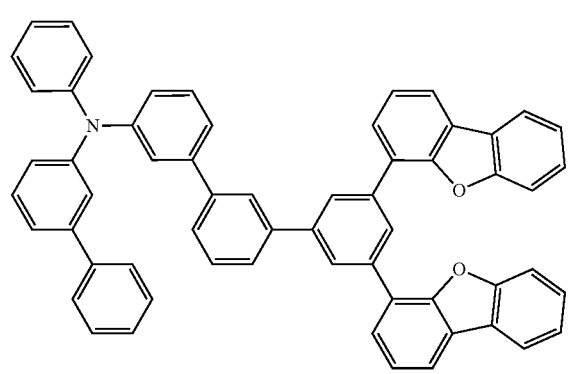
79
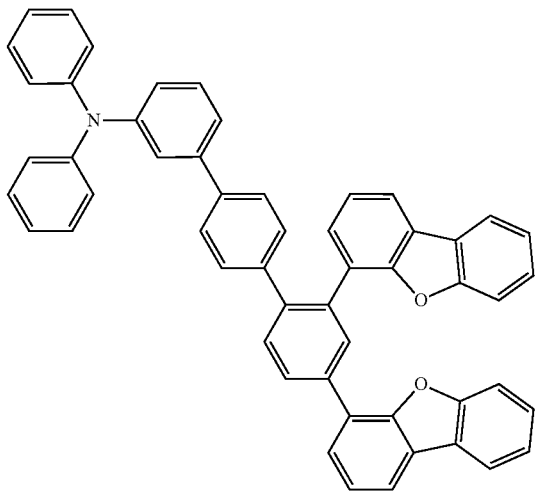
80
81
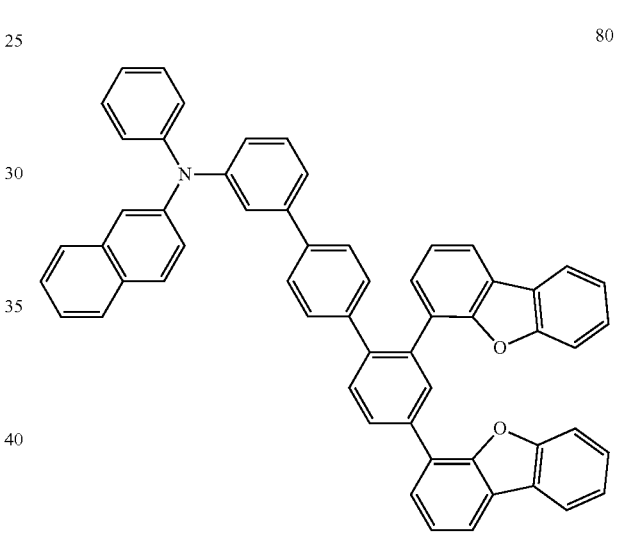

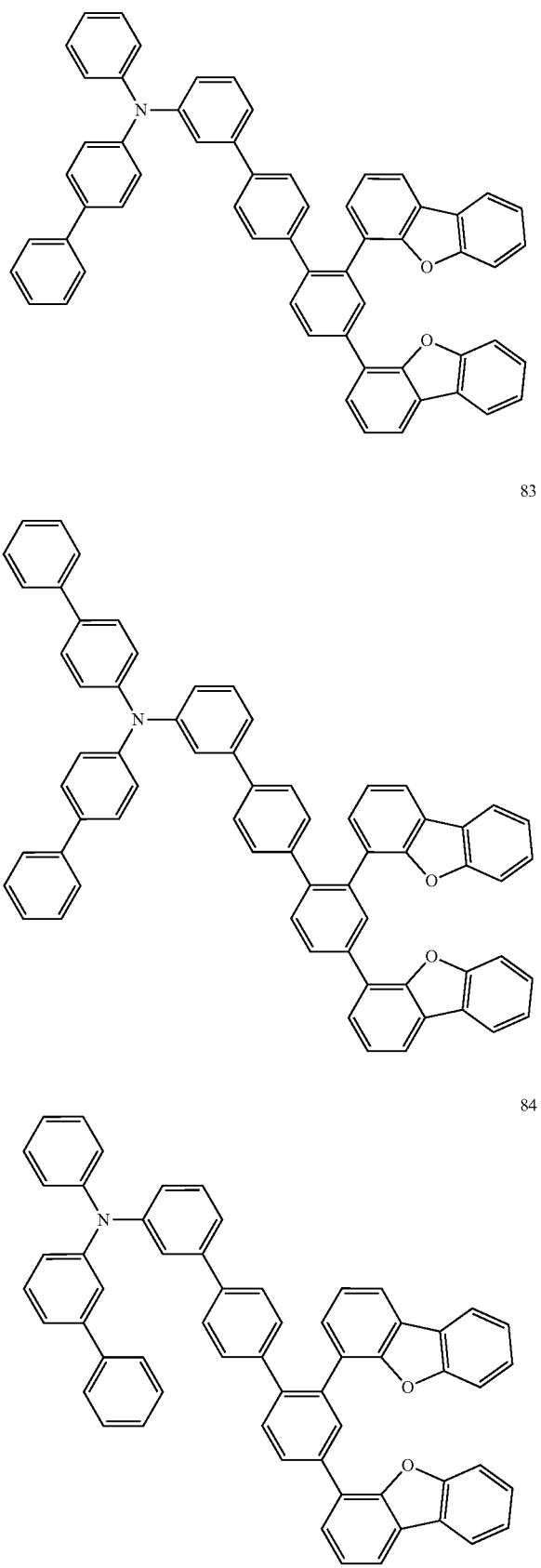
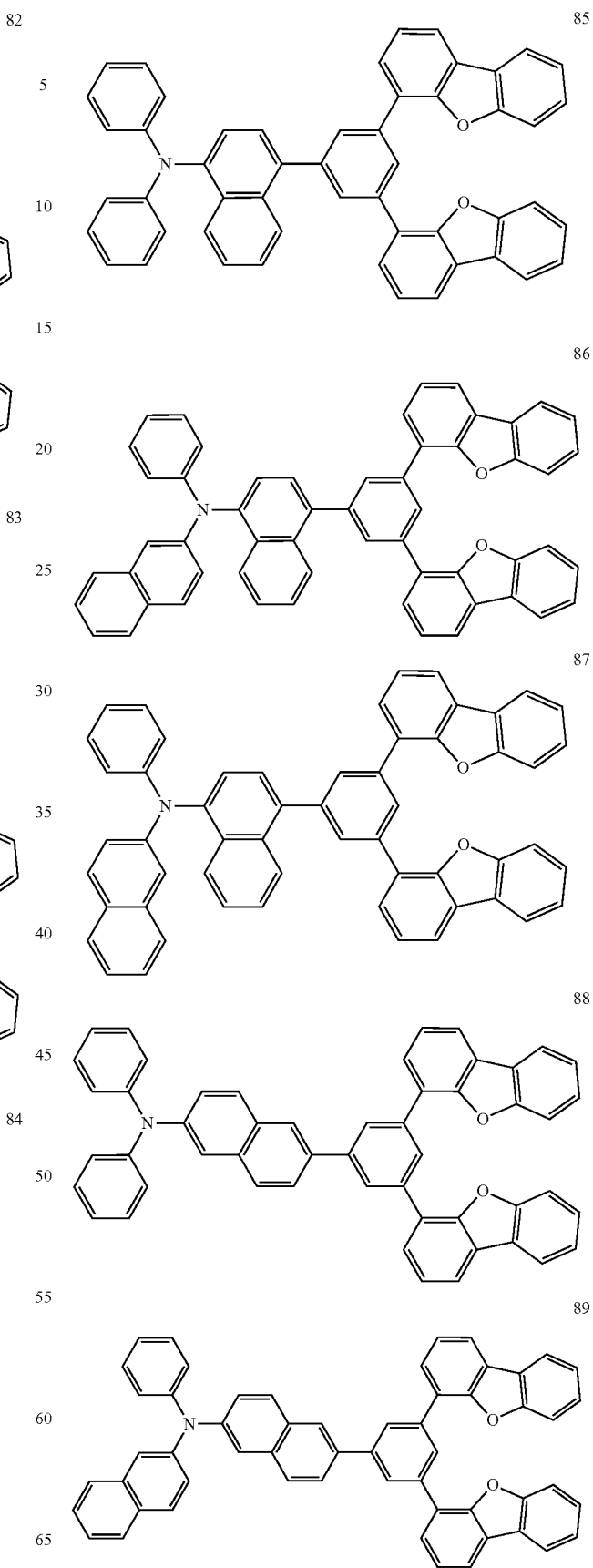

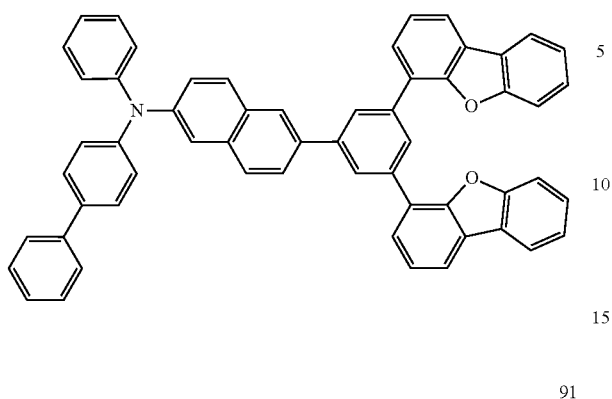
90
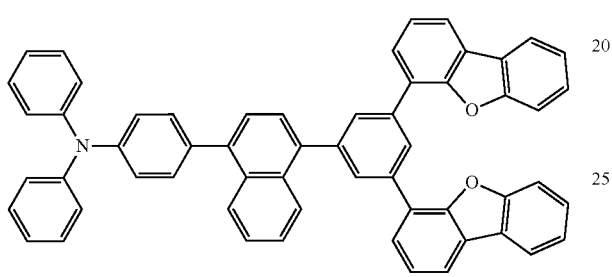
91
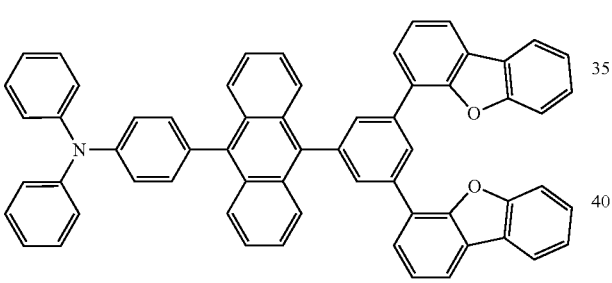
92
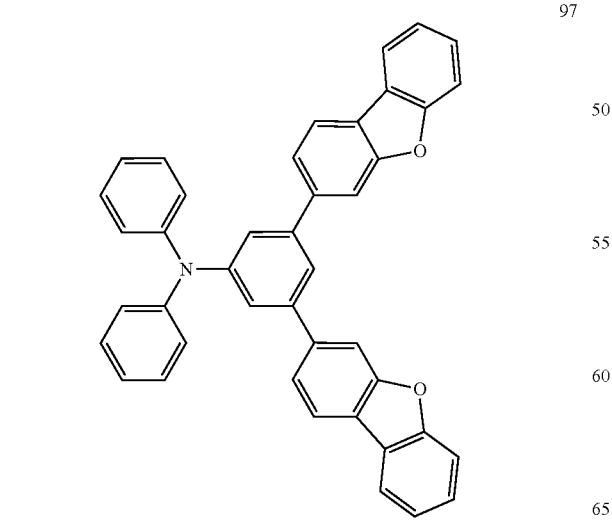
97
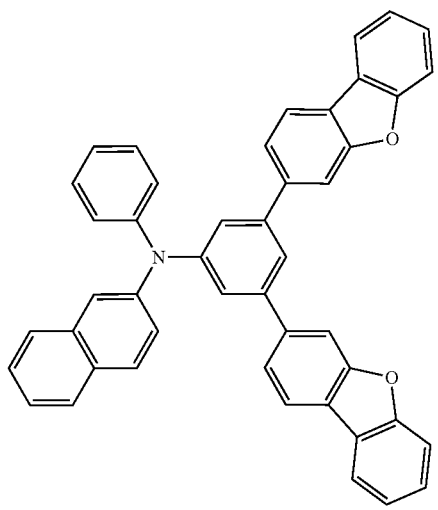
98
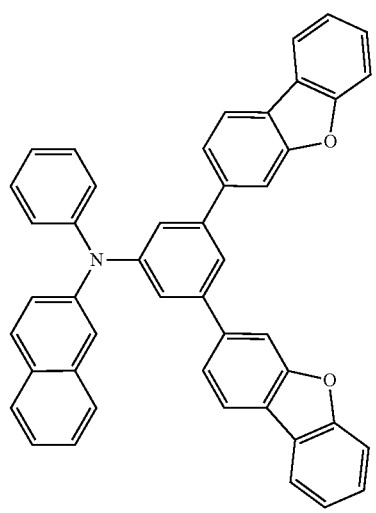
99
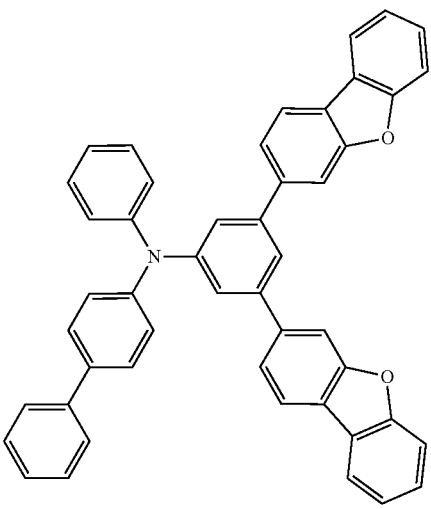
100

101
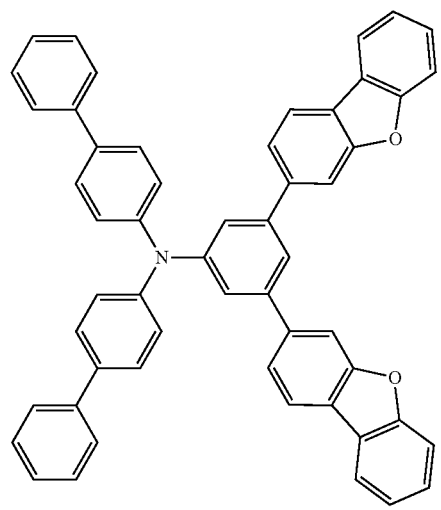
102
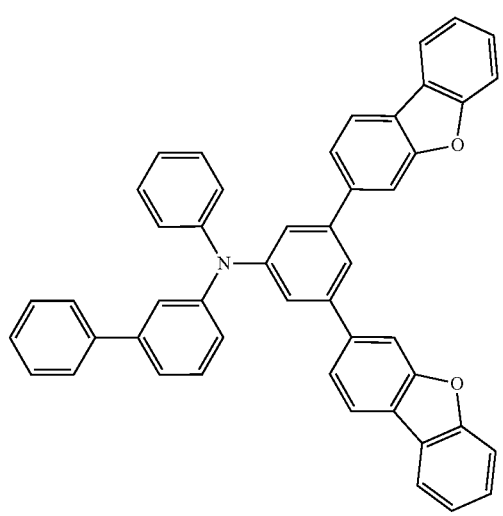
109
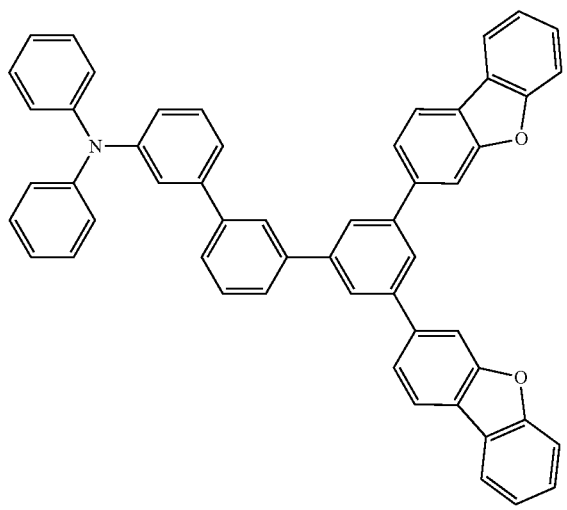
110
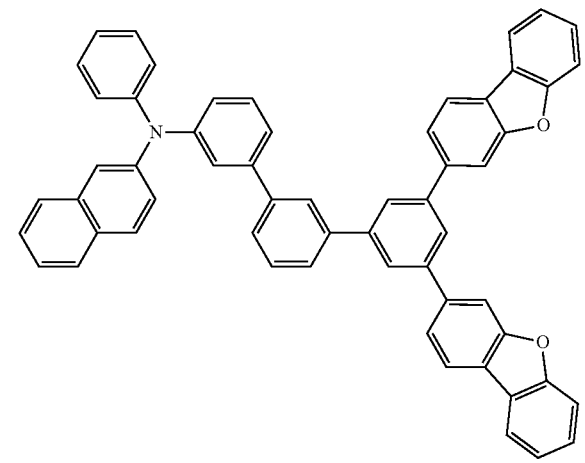
111
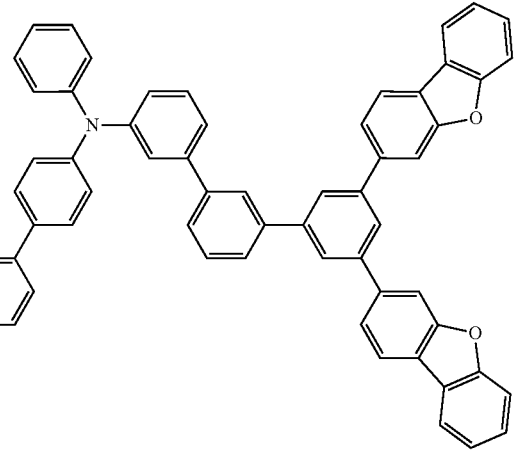
112

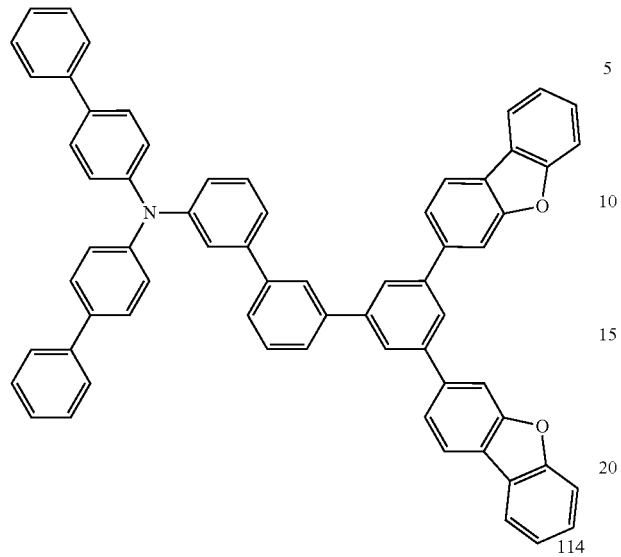
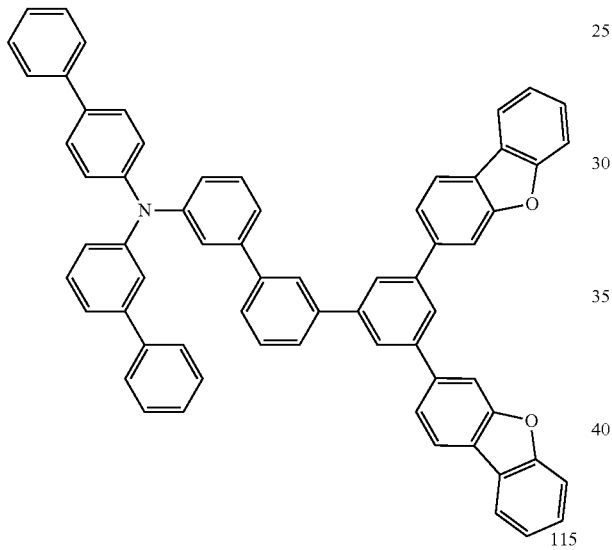
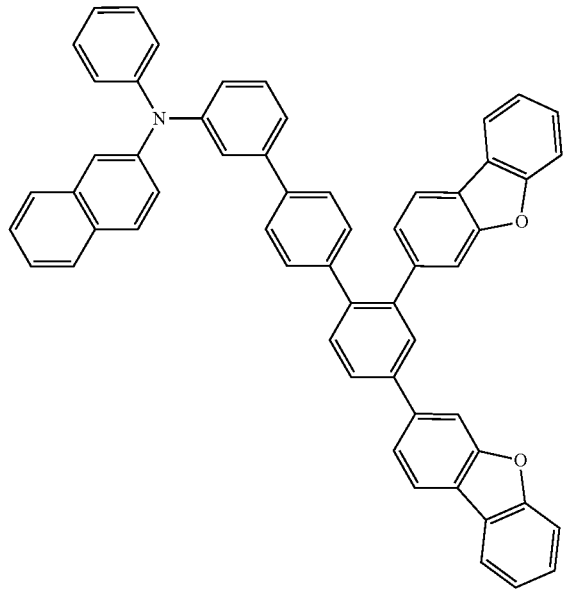
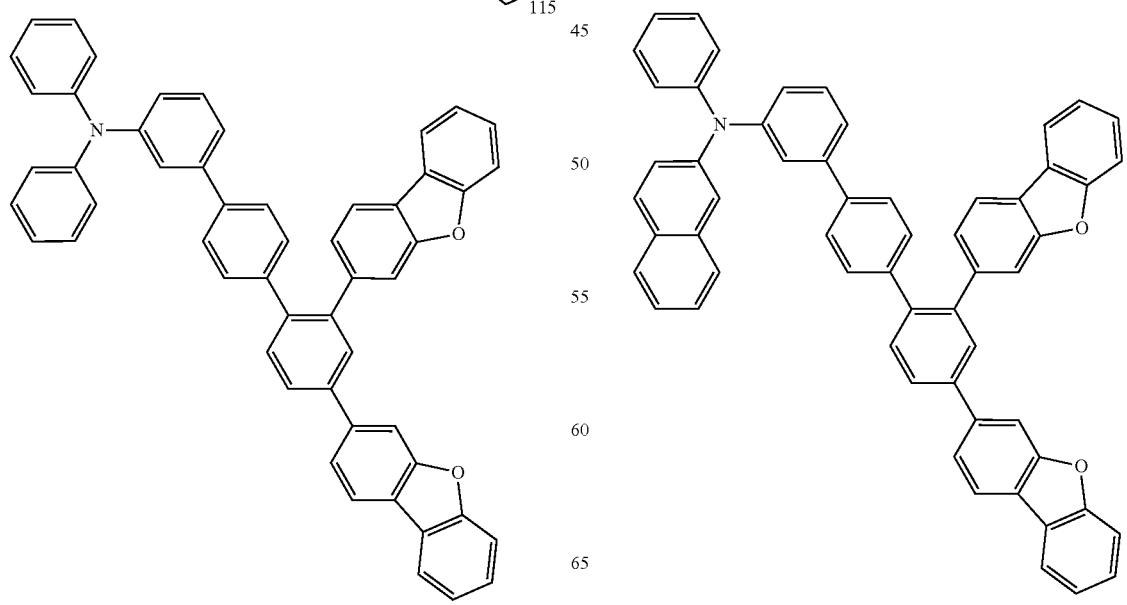

209
-continued
118
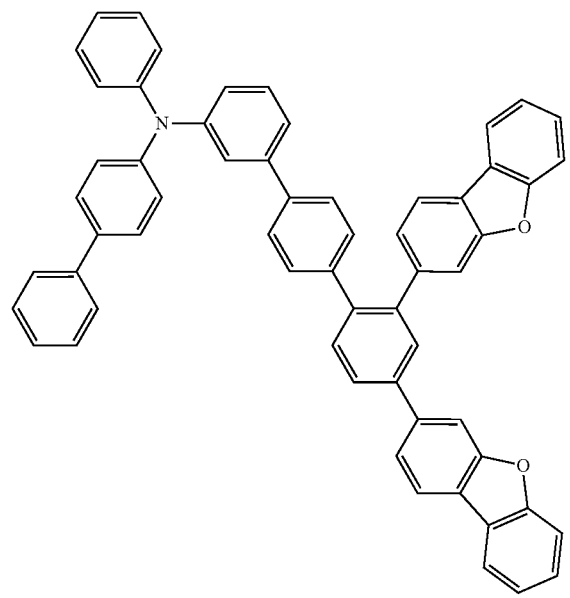
119
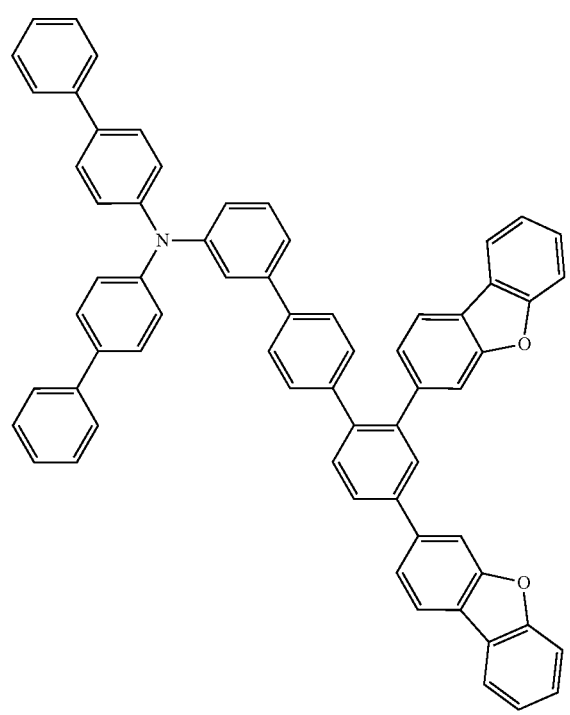
210
-continued
120
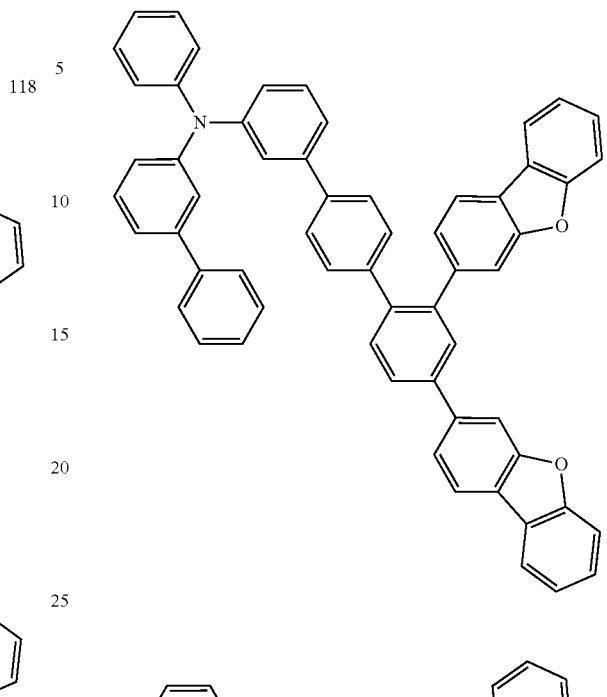
121
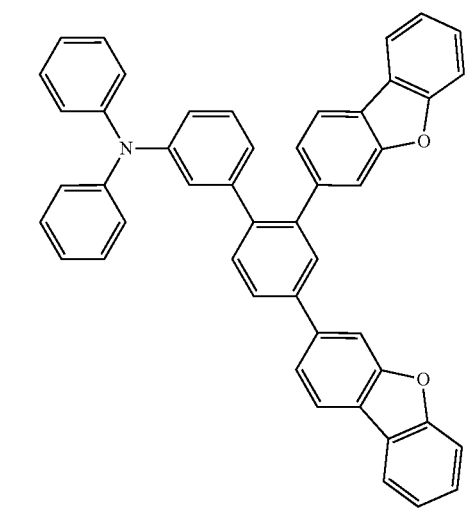
122
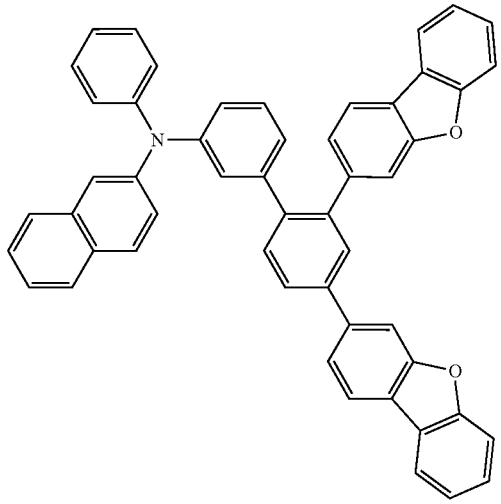

211
-continued
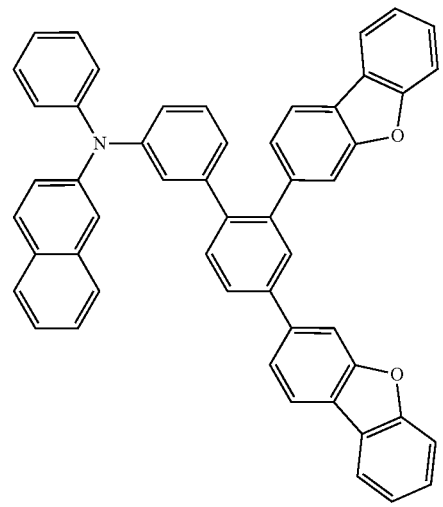
123
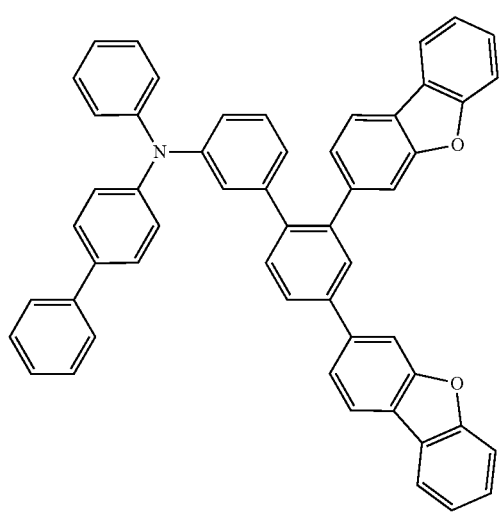
124
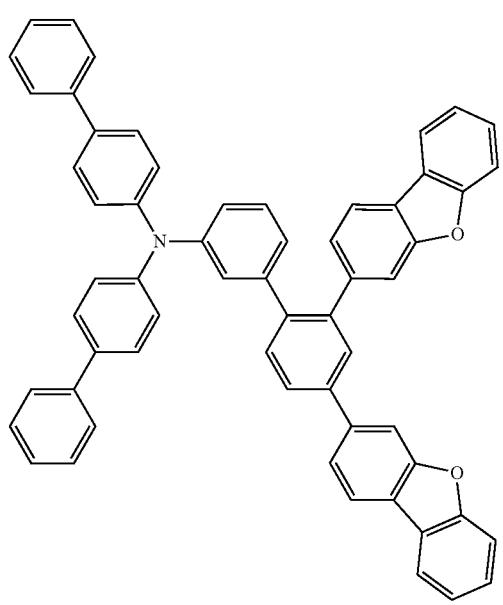
125
212
-continued
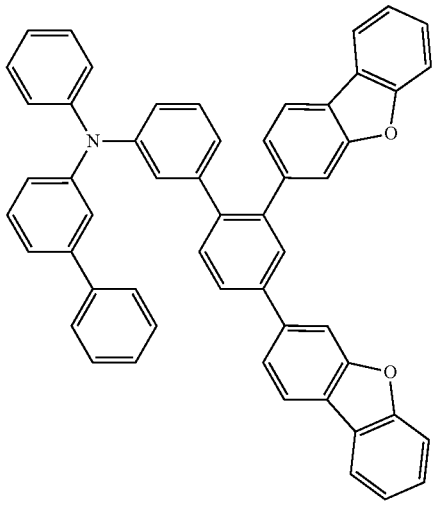
126
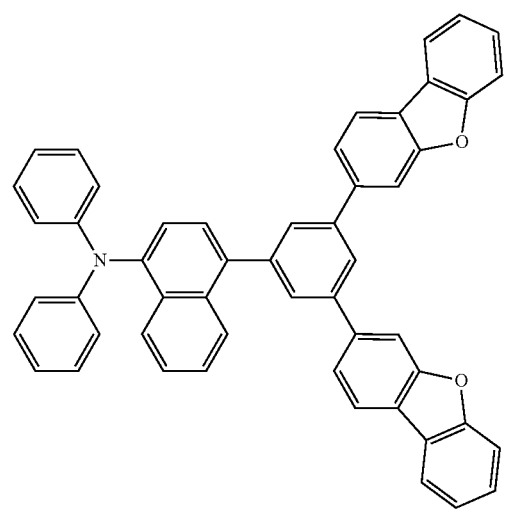
133
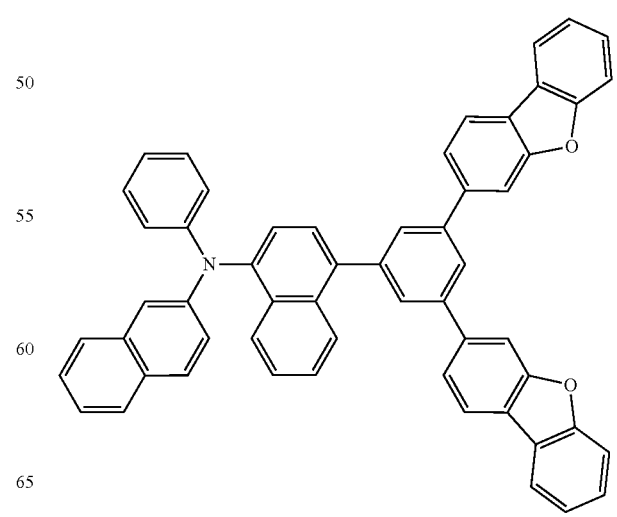
134

-continued
135
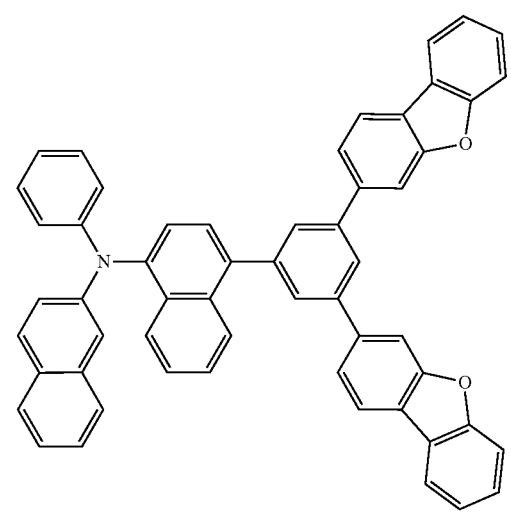
136
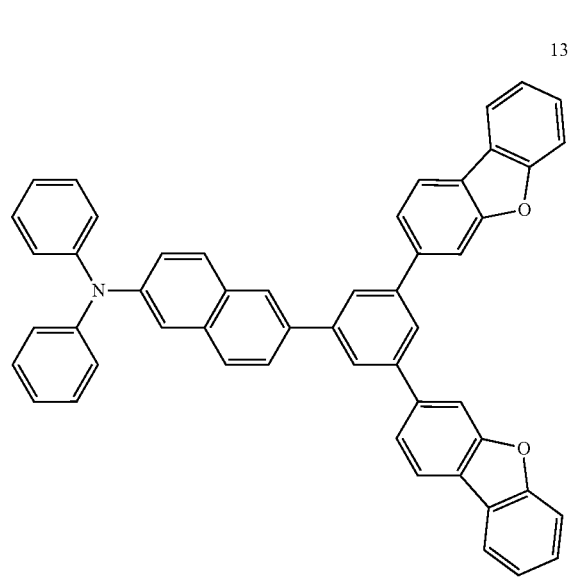
137
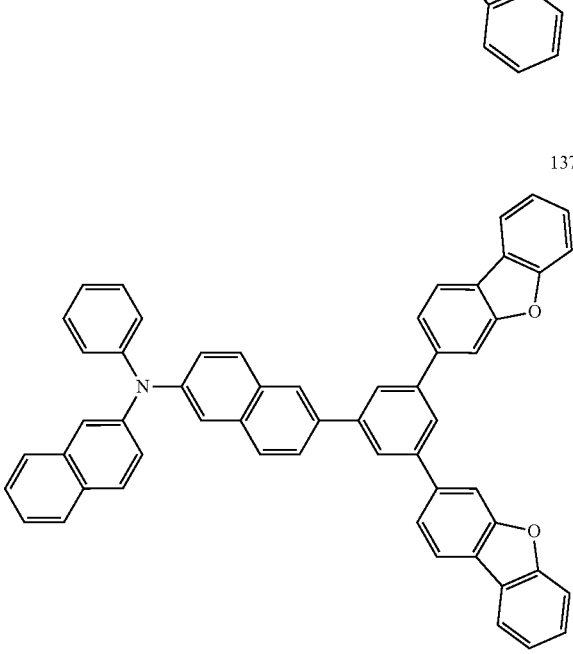
-continued
138
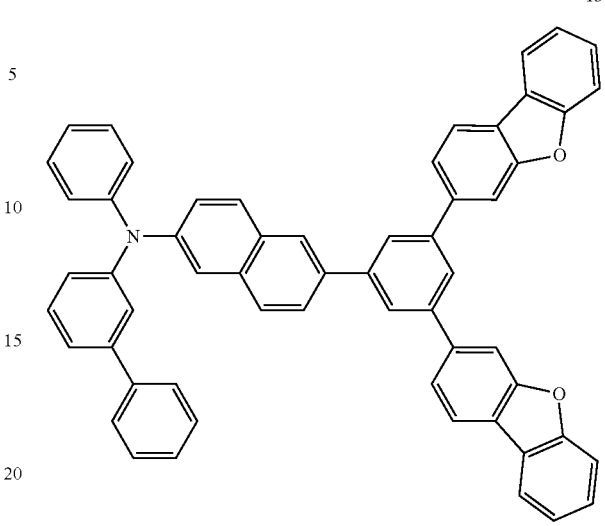
139
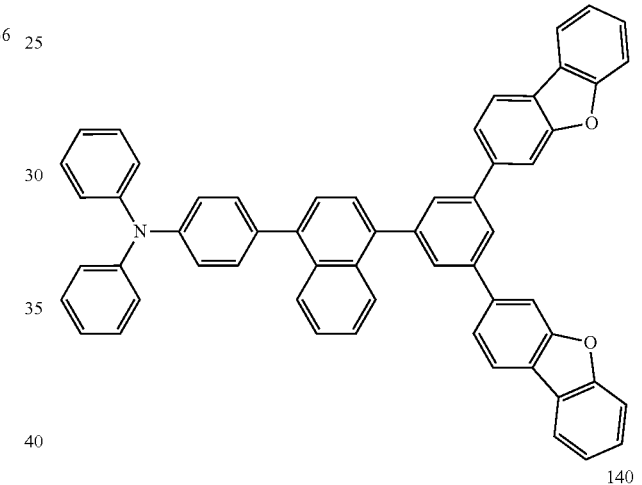
140
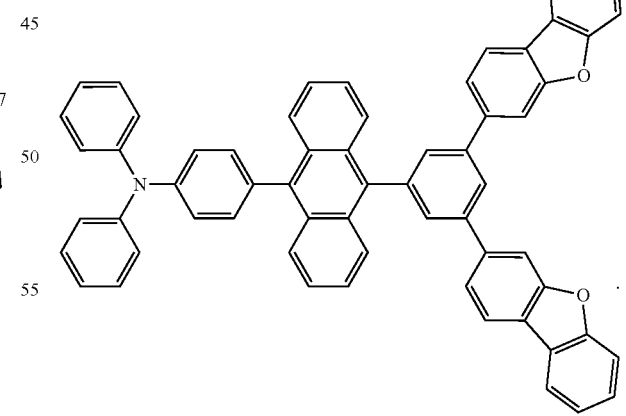
13. An organic light-emitting device, comprising:
a first electrode;
a second electrode facing the first electrode; and
an organic layer between the first electrode and the second electrode, the organic layer including an emission layer, wherein the organic layer includes the amine-based compound as claimed claim 1.

14. The organic light-emitting device as claimed in claim 13, wherein
the first electrode is an anode,
the second electrode is a cathode, and
the organic layer includes:
   a hole transport region between the first electrode and the emission layer, the hole transport region including at least one of a hole injection layer, a hole transport layer, a buffer layer, and an electron blocking layer, and
   an electron transport region between the emission layer and the second electrode, the electron transport region including at least one selected from a hole blocking layer, an electron transport layer, and an electron injection layer.

\* \* \* \* \*